(12) United States Patent
Welcher et al.

(10) Patent No.: US 6,656,707 B2
(45) Date of Patent: Dec. 2, 2003

(54) C3B/C4B COMPLEMENT RECEPTOR-LIKE MOLECULES AND USES THEREOF

(75) Inventors: Andrew A. Welcher, Ventura, CA (US); Gary S. Elliott, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/911,842

(22) Filed: Jul. 24, 2001

(65) Prior Publication Data

US 2002/0151483 A1 Oct. 17, 2002

Related U.S. Application Data

(60) Provisional application No. 60/222,438, filed on Aug. 1, 2000.

(51) Int. Cl.[7] .................. C12P 21/06; C12N 15/63; C12N 5/00; A61K 31/711
(52) U.S. Cl. ............... 435/69.1; 435/320.1; 435/325; 514/44; 536/23.5
(58) Field of Search ................ 435/69.1, 320.1, 435/325; 514/44; 536/23.5

(56) References Cited

U.S. PATENT DOCUMENTS 5,691,147 A * 11/1997 Draetta et al.

FOREIGN PATENT DOCUMENTS

| DE | 198 18 620 | 10/1999 |
|---|---|---|
| EP | 1 074 617 | 2/2001 |
| EP | 1 130 094 | 9/2001 |
| WO | WO 00/71710 | 11/2000 |

OTHER PUBLICATIONS

Genbank Accession No. AL079279, "Homo sapiens mRNA Full Length Insert cDNA Clone EURIMAGE 248114," Bassi et al., 1999.

Gilges et al., "Polydum: A Secreted Protein with Pentraxin, Complement Control Protein, Epidermal Growth Factor and von Willebrand Factor A Domains," Biochemical Journal, 352:49–59 (2000).

* cited by examiner

Primary Examiner—Gary Kunz
Assistant Examiner—Stephen Gucker
(74) Attorney, Agent, or Firm—Marshall, Gerstein & Borun LLP

(57) ABSTRACT

Novel C3b/C4b CR-like polypeptides and nucleic acid molecules encoding the same. The invention also provides vectors, host cells, selective binding agents, and methods for producing C3b/C4b CR-like polypeptides. Also provided for are methods for the treatment, diagnosis, amelioration, or prevention of diseases with C3b/C4b CR-like polypeptides.

19 Claims, 26 Drawing Sheets

FIGURE 1A

Map of Human C3b/C4b Complement Receptor Like cDNA (SEQ ID NO:1) and Amino Acid Sequences (SEQ ID NO:2)

cDNA Sequence

```
   1 GATTAGCGCG ATGTGGCCTC GCCTGGCCTT TTGTTGCTGG GGTCTGGCGC
  51 TCGTTTCGGG CTGGGCGACC TTTCAGCAGA TGTCCCCGTC GCGCAATTTC
 101 AGCTTCCGCC TCTTCCCCGA GACCGCGCCC GGGGCCCCCG GGAGTATCCC
 151 CGCGCCGCCC GCTCCTGGCG ACGAAGCGGC GGGGAGCAGA GTGGAGCGGC
 201 TGGGCCAGGC GTTCCGGCGA CGCGTGCGGC TGCTGCGGGA GCTCAGCGAG
 251 CGCCTGGAGC TTGTCTTCCT GGTGGATGAT TCGTCCAGCG TGGGCGAAGT
 301 CAACTTCCGC AGCGAGCTCA TGTTCGTCCG CAAGCTGCTG TCCGACTTCC
 351 CCGTGGTGCC CACGGCCACG CGCGTGGCCA TCGTGACCTT CTCGTCCAAG
 401 AACTACGTGG TGCCGCGCGT CGATTACATC TCCACCCGCC GCGCGCGCCA
 451 GCACAAGTGC GCGCTGCTCC TCCAAGAGAT CCCTGCCATC TCCTACCGAG
 501 GTGGCGGCAC CTACACCAAG GGCGCCTTCC AGCAAGCCGC GCAAATTCTT
 551 CTTCATGCTA GAGAAAACTC AACAAAAGTT GTATTTCTCA TCACTGATGG
 601 ATATTCCAAT GGGGGAGACC CTAGACCAAT TGCAGCGTCA CTGCGAGATT
 651 CAGGAGTGGA GATCTTCACT TTTGGCATAT GGCAAGGGAA CATTCGAGAG
 701 CTGAATGACA TGGCTTCCAC CCCAAAGGAG GAGCACTGTT ACCTGCTACA
 751 CAGTTTTGAA GAATTTGAGG CTTTAGCTCG CCGGGCATTG CATGAAGATC
 801 TACCTTCTGG GAGTTTTATT CAAGATGATA TGGTCCACTG CTCTTATCTT
 851 TGTGATGAAG GCAAGGACTG CTGTGACCGA ATGGGAAGCT GCAAATGTGG
 901 GACACACACA GGCCATTTTG AGTGCATCTG TGAAAAGGGG TATTACGGGA
 951 AAGGTCTGCA GTATGAATGC ACAGCTTGCC CATCGGGGAC ATACAAACCT
1001 GAAGGCTCAC CAGGAGGAAT CAGCAGTTGC ATTCCATGTC CTGATGAAAA
1051 TCACACCTCT CCACCTGGAA GCACATCCCC TGAAGACTGT GTCTGCAGAG
1101 AGGGATACAG GCATCTGGC CAGACCTGTG AACTTGTCCA CTGCCCTGCC
1151 CTGAAGCCTC CCGAAAATGG TTACTTTATC CAAAACACTT GCAACAACCA
1201 CTTCAATGCA GCCTGTGGGG TCCGATGTCA CCCTGGATTT GATCTTGTGG
1251 GAAGCAGCAT CATCTTATGT CTACCCAATG GTTTGTGGTC CGGTTCAGAG
```

Figure 1B

```
1301  AGCTACTGCA GAGTAAGAAC ATGTCCTCAT CTCCGCCAGC CGAAACATGG
1351  CCACATCAGC TGTTCTACAA GGGAAATGTT ATATAAGACA ACATGTTTGG
1401  TTGCCTGTGA TGAAGGGTAC AGACTAGAAG GCAGTGATAA GCTTACTTGT
1451  CAAGGAAACA GCCAGTGGGA TGGGCCAGAA CCCCGGTGTG TGGAGCGCCA
1501  CTGTTCCACC TTTCAGATGC CAAAGATAT CATCATATCC CCCCACAACT
1551  GTGGCAAGCA GCCAGCCAAA TTTGGGACGA TCTGCTATGT AAGTTGCCGC
1601  CAAGGGTTCA TTTTATCTGG AGTCAAAGAA ATGCTGAGAT GTACCACTTC
1651  TGGAAAATGG AATGTCGGAG TTCAGGCAGC TGTGTGTAAA GACGTGGAGG
1701  CTCCTCAAAT CAACTGTCCT AAGGACATAG AGGCTAAGAC TCTGGAACAG
1751  CAAGATTCTG CCAATGTTAC CTGGCAGATT CCAACAGCTA AAGACAACTC
1801  TGGTGAAAAG GTGTCAGTCC ACGTTCATCC AGCTTTCACC CCACCTTACC
1851  TTTTCCCAGT TGGAGATGTT GCTATCGTAT ACACGGCAAC TGACCTATCC
1901  GGCAACCAGG CCAGCTGCAT TTTCCATATC AAGGTTATTG ATGCAGAACC
1951  ACCTGTCATA GACTGGTGCA GATCTCCACC TCCCGTCCAG GTCTCGGAGA
2001  AGGTACATGC CGCAAGCTGG GATGAGCCTC AGTTCTCAGA CAACTCAGGG
2051  GCTGAATTGG TCATTACCAG AAGTCATACA CAAGGAGACC TTTTCCCTCA
2101  AGGGGAGACT ATAGTACAGT ATACAGCCAC TGACCCCTCA GGCAATAACA
2151  GGACATGTGA TATCCATATT GTCATAAAAG GTTCTCCCTG TGAAATTCCA
2201  TTCACACCTG TAAATGGGGA TTTTATATGC ACTCCAGATA ATACTGGAGT
2251  CAACTGTACA TTAACTTGCT TGGAGGGCTA TGATTTCACA GAAGGGTCTA
2301  CTGACAAGTA TTATTGTGCT TATGAAGATG GCGTCTGGAA ACCAACATAT
2351  ACCACTGAAT GGCCAGACTG TGCCAAAAAA CGTTTTGCTA CCACGGGTT
2401  CAAGTCCTTT GAGATGTTCT ACAAAGCAGC TCGTTGTGAT GACACAGATC
2451  TGATGAAGAA GTTTTCTGAA GCATTTGAGA CGACCCTGGG AAAAATGGTC
2501  CCATCATTTT GTAGTGATGC AGAGGACATT GACTGCAGAC TGGAGGAGAA
2551  CCTGACCAAA AAATATTGCC TAGAATATAA TTATGACTAT GAAAATGGCT
2601  TTGCAATTGG ACCAGGTGGC TGGGGTGCAG CTAATAGGCT GGATTACTCT
2651  TACGATGACT TCCTGGACAC TGTGCAAGAA ACAGCCACAA GCATCGGCAA
2701  TGCCAAGTCC TCACGGATTA AAAGAAGTGC CCCATTATCT GACTATAAAA
```

Figure 1C

```
2751  TTAAGTTAAT TTTTAACATC ACAGCTAGTG TGCCATTACC CGATGAAAGA
2801  AATGATACCC TTGAATGGGA AAATCAGCAA CGACTCCTTC AGACATTGGA
2851  AACTATCACA AATAAACTGA AAAGGACTCT CAACAAAGAC CCCATGTATT
2901  CCTTTCAGCT TGCATCAGAA ATACTTATAG CCGACAGCAA TTCATTAGAA
2951  ACAAAAAAGG CTTCCCCCTT CTGCAGACCA GGCTCAGTGC TGAGAGGGCG
3001  TATGTGTGTC AATTGCCCTT TGGGAACCTA TTATAATCTG AACATTTCA
3051  CCTGTGAAAG CTGCCGGATC GGATCCTATC AAGATGAAGA AGGGCAACTT
3101  GAGTGCAAGC TTTGCCCCTC TGGGATGTAC ACGGAATATA TCCATTCAAG
3151  AAACATCTCT GATTGTAAAG CTCAGTGTAA ACAAGGCACC TACTCATACA
3201  GTGGACTTGA GACTTGTGAA TCGTGTCCAC TGGGCACTTA TCAGCCAAAA
3251  TTTGGTTCCC GGAGCTGCCT CTCGTGTCCA GAAAACACCT CAACTGTGAA
3301  AAGAGGAGCC GTGAACATTT CTGCATGTGG AGTTCCTTGT CCAGAAGGAA
3351  AATTCTCGCG TTCTGGGTTA ATGCCCTGTC ACCCATGTCC TCGTGACTAT
3401  TACCAACCTA ATGCAGGGAA GGCCTTCTGC CTGGCCTGTC CCTTTTATGG
3451  AACTACCCCA TTCGCTGGTT CCAGATCCAT CACAGAATGT TCAAGTTTTA
3501  GTTCAACTTT CTCAGCGGCA GAGGAAAGTG TGGTGCCCCC TGCCTCTCTT
3551  GGACATATTA AAAGAGGCA TGAAATCAGC AGTCAGGTTT TCCATGAATG
3601  CTTCTTTAAC CCTTGCCACA ATAGTGGAAC CTGCCAGCAA CTTGGGCGTG
3651  GTTATGTTTG TCTCTGTCCA CTTGGATATA CAGGCTTAAA GTGTGAAACA
3701  GACATCGATG AGTGCAGCCC ACTGCCTTGC CTCAACAATG GAGTTTGTAA
3751  AGACCTAGTT GGGGAATTCA TTTGTGAGTG CCCATCAGGT TACACAGGTC
3801  AGCGGTGTGA AGAAAATATA AATGAGTGTA GCTCCAGTCC TTGTTTAAAT
3851  AAAGGAATCT GTGTTGATGG TGTGGCTGGC TATCGTTGCA CATGTGTGAA
3901  AGGATTTGTA GGCCTGCATT GTGAAACAGA AGTCAATGAA TGCCAGTCAA
3951  ACCCATGCTT AAATAATGCA GTCTGTGAAG ACCAGGTTGG GGGATTCTTG
4001  TGCAAATGCC CACCTGGATT TTTGGGTACC CGATGTGGAA AGAACGTCGA
4051  TGAGTGTCTC AGTCAGCCAT GCAAAAATGG AGCTACCTGT AAAGACGGTG
4101  CCAATAGCTT CAGATGCCTG TGTGCAGCTG GCTTCACAGG ATCACACTGT
4151  GAATTGAACA TCAATGAATG TCAGTCTAAT CCATGTAGAA ATCAGGCCAC
```

Figure 1D

```
4201   CTGTGTGGAT GAATTAAATT CATACAGTTG TAAATGTCAG CCAGGATTTT
4251   CAGGCAAAAG GTGTGAAACA GAACAGTCTA CAGGCTTTAA CCTGGATTTT
4301   GAAGTTTCTG GCATCTATGG ATATGTCATG CTAGATGGCA TGCTCCCATC
4351   TCTCCATGCT CTAACCTGTA CCTTCTGGAT GAAATCCTCT GACGACATGA
4401   ACTATGGAAC ACCAATCTCC TATGCAGTTG ATAACGGCAG CGACAATACC
4451   TTGCTCCTGA CTGATTATAA CGGCTGGGTT CTTTATGTGA ATGGCAGGGA
4501   AAAGATAACA AACTGTCCCT CGGTGAATGA TGGCAGATGG CATCATATTG
4551   CAATCACTTG GACAAGTGCC AATGGCATCT GGAAAGTCTA TATCGATGGG
4601   AAATTATCTG ACGGTGGTGC TGGCCTCTCT GTTGGTTTGC CCATACCTGG
4651   TGGTGGTGCG TTAGTTCTGG GGCAAGAGCA AGACAAAAAA GGAGAGGGAT
4701   TCAGCCCAGC TGAGTCTTTT GTGGGCTCCA TAAGCCAGCT CAACCTCTGG
4751   GACTATGTCC TGTCTCCACA GCAGGTGAAG TCACTGGCTA CCTCCTGCCC
4801   AGAGGAACTC AGTAAAGGAA ACGTGTTAGC ATGGCCTGAT TTCTTGTCAG
4851   GAATTGTGGG GAAAGTGAAG ATCGATTCTA AGAGCATATT TTGTTCTGAT
4901   TGCCCACGCT TAGGAGGGTC AGTGCCTCAT CTGAGAACTG CATCTGAAGA
4951   TTTAAAGCCA GGTTCCAAAG TCAATCTGTT CTGTGATCCA GGCTTCCAGC
5001   TGGTCGGGAA CCCTGTGCAG TACTGTCTGA ATCAAGGACA GTGGACACAA
5051   CCACTTCCTC ACTGTGAACG CATTAGCTGT GGGGTGCCAC CTCCTTTGGA
5101   GAATGGCTTC CATTCAGCCG ATGACTTCTA TGCTGGCAGC ACAGTAACCT
5151   ACCAGTGCAA CAATGGCTAC TATCTATTGG GTGACTCAAG GATGTTCTGT
5201   ACAGATAATG GGAGCTGGAA CGGCGTTTCA CCATCCTGCC TTGATGTCGA
5251   TGAGTGTGCA GTTGGATCAG ATTGTAGTGA GCATGCTTCT TGCCTGAACG
5301   TAGATGGATC CTACATATGT TCATGTGTCC CACCGTACAC AGGAGATGGG
5351   AAAAACTGTG CAGAACCTAT AAAATGTAAG GCTCCAGGAA ATCCGGAAAA
5401   TGGCCACTCC TCAGGTGAGA TTTATACAGT AGGTGCCGAA GTCACATTTT
5451   CGTGTCAGGA AGGATACCAG TTGATGGGAG TAACCAAAAT CACATGTTTG
5501   GAGTCTGGAG AATGGAATCA TCTAATACCA TATTGTAAAG CTGTTTCATG
5551   TGGTAAACCG GCTATTCCAG AAAATGGTTG CATTGAGGAG TTAGCATTTA
```

Figure 1E

```
5601  CTTTTGGCAG CAAAGTGACA TATAGGTGTA ATAAAGGATA TACTCTGGCC
5651  GGTGATAAAG AATCATCCTG TCTTGCTAAC AGTTCTTGGA GTCATTCCCC
5701  TCCTGTGTGT GAACCAGTGA AGTGTTCTAG TCCGGAAAAT ATAAATAATG
5751  GAAAATATAT TTGAGTGGG CTTACCTACC TTTCTACTGC ATCATATTCA
5801  TGCGATACAG GATACAGCTT ACAGGGCCCT TCCATTATTG AATGCACGGC
5851  TTCTGGCATC TGGGACAGAG CGCCACCTGC CTGTCACCTC GTCTTCTGTG
5901  GAGAACCACC TGCCATCAAA GATGCTGTCA TTACGGGGAA TAACTTCACT
5951  TTCAGGAACA CCGTCACTTA CACTTGCAAA GAAGGCTATA CTCTTGCTGG
6001  TCTTGACACC ATTGAATGCC TGGCCGACGG CAAGTGGAGT AGAAGTGACC
6051  AGCAGTGCCT GGCTGTCTCC TGTGATGAGC CACCCATTGT GGACCACGCC
6101  TCTCCAGAGA CTGCCCATCG GCTCTTTGGA GACATTGCAT TCTACTACTG
6151  CTCTGATGGT TACAGCCTAG CAGACAATTC CCAGCTTCTC TGCAATGCCC
6201  AGGGCAAGTG GGTACCCCCA GAAGGTCAAG ACATGCCCCG TTGTATAGCT
6251  CATTTCTGTG AAAAACCTCC ATCGGTTTCC TATAGCATCT GGAATCTGT
6301  GAGCAAAGCA AAATTTGCAG CTGGCTCAGT TGTGAGCTTT AAATGCATGG
6351  AAGGCTTTGT ACTGAACACC TCAGCAAAGA TTGAATGTAT GAGAGGTGGG
6401  CAGTGGAACC CTTCCCCCAT GTCCATCCAG TGCATCCCTG TGCGGTGTGG
6451  AGAGCCACCA AGCATCATGA ATGGCTATGC AAGTGGATCA AACTACAGTT
6501  TTGGAGCCAT GGTGGCTTAC AGCTGCAACA AGGGGTTCTA CATCAAAGGG
6551  GAAAAGAAGA GCACCTGCGA AGCCACAGGG CAGTGGAGTA GTCCTATACC
6601  GACGTGCCAC CCGGTATCTT GTGGTGAACC ACCTAAGGTT GAGAATGGCT
6651  TTCTGGAGCA TACAACTGGC AGGATCTTTG AGAGTGAAGT GAGGTATCAG
6701  TGTAACCCGG GCTATAAGTC AGTCGGAAGT CCTGTATTTG TCTGCCAAGC
6751  CAATCGCCAC TGGCACAGTG AATCCCCTCT GATGTGTGTT CCTCTCGACT
6801  GTGGAAAACC TCCCCCGATC CAGAATGGCT TCATGAAAGG AGAAAACTTT
6851  GAAGTAGGGT CCAAGGTTCA GTTTTTCTGT AATGAGGGTT ATGAGCTTGT
6901  TGGTGACAGT TCTTGGACAT GTCAGAAATC TGGCAAATGG AATAAGAAGT
6951  CAAATCCAAA GTGCATGCCT GCCAAGTGCC CAGAGCCGCC CCTCTTGGAA
7001  AACCAGCTAG TATTAAAGGA GTTGACCACC GAGGTAGGAG TTGTGACATT
```

Figure 1F

```
7051  TTCCTGTAAA GAAGGGCATG TCCTGCAAGG CCCCTCTGTC CTGAAATGCT
7101  TGCCATCCCA GCAATGGAAT GACTCTTTCC CTGTTTGTAA GATTGTTCTT
7151  TGTACCCCAC CTCCCCTAAT TTCCTTTGGT GTCCCCATTC CTTCTTCTGC
7201  TCTTCATTTT GGAAGTACTG TCAAGTATTC TTGTGTAGGT GGGTTTTTCC
7251  TAAGAGGAAA TTCTACCACC CTCTGCCAAC CTGATGGCAC CTGGAGCTCT
7301  CCACTGCCAG AATGTGTTCC AGTAGAATGT CCCCAACCTG AGGAAATCCC
7351  CAATGGAATC ATTGATGTGC AAGGCCTTGC CTATCTCAGC ACAGCTCTCT
7401  ATACCTGCAA GCCAGGCTTT GAATTGGTGG AAATACTAC CACCCTTTGT
7451  GGAGAAAATG GTCACTGGCT TGGAGGAAAA CCAACATGTA AAGCCATTGA
7501  GTGCCTGAAA CCCAAGGAGA TTTTGAATGG CAAATTCTCT TACACGGACC
7551  TACACTATGG ACAGACCGTT ACCTACTCTT GCAACCGAGG CTTTCGGCTC
7601  GAAGGTCCCA GTGCCTTGAC CTGTTTAGAG ACAGGTGATT GGGATGTAGA
7651  TGCCCCATCT TGCAATGCCA TCCACTGTGA TTCCCCACAA CCCATTGAAA
7701  ATGGTTTTGT AGAAGGTGCA GATTACAGCT ATGGTGCCAT AATCATCTAC
7751  AGTTGCTTCC CTGGGTTTCA GGTGGCTGGT CATGCCATGC AGACCTGTGA
7801  AGAGTCAGGA TGGTCAAGTT CCATCCCAAC ATGTATGCCA ATAGACTGTG
7851  GCCTCCCTCC TCATATAGAT TTTGGAGACT GTACTAAACT CAAAGATGAC
7901  CAGGGATATT TTGAGCAAGA AGACGACATG ATGGAAGTTC CATATGTGAC
7951  TCCTCACCCT CCTTATCATT TGGGAGCAGT GGCTAAAACC TGGGAAAATA
8001  CAAAGGAGTC TCCTGCTACA CATTCATCAA ACTTTCTGTA TGGTACCATG
8051  GTTTCATACA CCTGTAATCC AGGATATGAA CTTCTGGGGA ACCCTGTGCT
8101  GATCTGCCAG GAAGATGGAA CTTGGAATGG CAGTGCACCA TCCTGCATTT
8151  CAATTGAATG TGACTTGCCT ACTGCTCCTG AAAATGGCTT TTTGCGTTTT
8201  ACAGAGACTA GCATGGGAAG TGCTGTGCAG TATAGCTGTA AACCTGGACA
8251  CATTCTAGTG GGCTCTGACT TAAGGCTTTG TCTAGAGAAT AGAAAGTGGA
8301  GTGGTGCCTC CCCACGCTGT GAAGCCATTT CATGCAAAAA GCCAAATCCA
8351  GTCATGAATG GATCCATCAA AGGAAGCAAC TACACATACC TGAGCACGTT
8401  GTACTATGAG TGTGACCCCG GATATGTGCT GAATGGCACT GAGAGGAGAA
8451  CATGCCAGGA TGACAAAAAC TGGGATGAGG ATGAGCCCAT TTGCATTCCT
```

Figure 1G

```
8501  GTGGACTGCA GTTCACCCCC AGTCTCAGCC AATGGCCAGG TGAGAGGAGA
8551  CGAGTACACA TTCCAAAAAG AGATTGAATA CACTTGCAAT GAAGGGTTCT
8601  TGCTTGAGGG AGCCAGGAGT CGGGTTTGTC TTGCCAATGG AAGTTGGAGT
8651  GGAGCCACTC CCGACTGTGT GCCTGTCAGA TGTGCCACCC CGCCACAACT
8701  GGCCAATGGG GTGACGGAAG GCCTGGACTA TGGCTTCATG AAGGAAGTAA
8751  CATTCCACTG TCATGAGGGC TACATCTTGC ACGGTGCTCC AAAACTCACC
8801  TGTCAGTCAG ATGGCAACTG GGATGCAGAG ATTCCTCTCT GTAAACCAGT
8851  CAACTGTGGA CCTCCTGAAG ATCTTGCCCA TGGTTTCCCT AATGGTTTTT
8901  CCTTTATTCA TGGGGCCAT ATACAGTATC AGTGCTTTCC TGGTTATAAG
8951  CTCCATGGAA ATTCATCAAG AAGGTGCCTC TCCAATGGCT CCTGGAGTGG
9001  CAGCTCACCT TCCTGCCTGC CTTGCAGATG TTCCACACCA GTAATTGAAT
9051  ATGGAACTGT CAATGGGACA GATTTTGACT GTGGAAAGGC AGCCCGGATT
9101  CAGTGCTTCA AAGGCTTCAA GCTCCTAGGA CTTTCTGAAA TCACCTGTGA
9151  AGCCGATGGC CAGTGGAGCT CTGGGTTCCC CCACTGTGAA CACACTTCTT
9201  GTGGTTCTCT TCCAATGATA CCAAATGCGT TCATCAGTGA GACCAGCTCT
9251  TGGAAGGAAA ATGTGATAAC TTACAGCTGC AGGTCTGGAT ATGTCATACA
9301  AGGCAGTTCA GATCTGATTT GTACAGAGAA AGGGGTATGG AGCCAGCCTT
9351  ATCCAGTCTG TGAGCCCTTG TCCTGTGGGT CCCCACCGTC TGTCGCCAAT
9401  GCAGTGGCAA CTGGAGAGGC ACACACCTAT GAAAGTGAAG TGAAACTCAG
9451  ATGTCTGGAA GGTTATACGA TGGATACAGA TACAGATACA TTCACCTGTC
9501  AGAAAGATGG TCGCTGGTTC CCTGAGAGAA TCTCCTGCAG TCCTAAAAAA
9551  TGTCCTCTCC CGGAAAACAT AACACATATA CTTGTTCATG GGACGATTT
9601  CAGTGTGAAT AGGCAAGTTT CTGTGTCATG TGCAGAAGGG TATACCTTTG
9651  AGGGAGTTAA CATATCAGTA TGTCAGCTTG ATGGAACCTG GGAGCCACCA
9701  TTCTCCGATG AATCTTGCAG TCCAGTTTCT TGTGGGAAAC CTGAAAGTCC
9751  AGAACATGGA TTTGTGGTTG GCAGTAAATA CACCTTTGAA AGCACAATTA
9801  TTTATCAGTG TGAGCCTGGC TATGAACTAG AGGGAACAG GGAACGCGTC
9851  TGCCAGGAGA ACAGACAGTG GAGTGGAGGG GTGGCAATAT GCAAAGAGAC
```

Figure 1H

```
9901   CAGGTGTGAA ACTCCACTTG AATTTCTCAA TGGGAAAGCT GACATTGAAA
9951   ACAGGACGAC TGGACCCAAC GTGGTATATT CCTGCAACAG AGGCTACAGT
10001  CTTGAAGGGC ATCTGAGGC ACACTGCACA GAAAATGGAA CCTGGAGCCA
10051  CCCAGTCCCT CTCTGCAAAC CAAATCCATG CCCTGTTCCT TTTGTGATTC
10101  CCGAGAATGC TCTGCTGTCT GAAAAGGAGT TTTATGTTGA TCAGAATGTG
10151  TCCATCAAAT GTAGGGAAGG TTTTCTGCTG CAGGGCCACG GCATCATTAC
10201  CTGCAACCCC GACGAGACGT GGACACAGAC AAGCGCCAAA TGTGAAAAAA
10251  TCTCATGTGG TCCACCAGCT CACGTAGAAA ATGCAATTGC TCGAGGCGTA
10301  CATTATCAAT ATGGAGACAT GATCACCTAC TCATGTTACA GTGGATACAT
10351  GTTGGAGGGT TTCCTGAGGA GTGTTTGTTT AGAAAATGGA ACATGGACAT
10401  CACCTCCTAT TTGCAGAGCT GTCTGTCGAT TCCATGTCA GAATGGGGGC
10451  ATCTGCCAAC GCCCAAATGC TTGTTCCTGT CCAGAGGGCT GGATGGGGCG
10501  CCTCTGTGAA GAACCAATCT GCATTCTTCC CTGTCTGAAC GGAGGTCGCT
10551  GTGTGGCCCC TTACCAGTGT GACTGCCCGC CTGGCTGGAC GGGGTCTCGC
10601  TGTCATACAG CTGTTTGCCA GTCTCCCTGC TTAAATGGTG GAAAATGTGT
10651  AAGACCAAAC CGATGTCACT GTCTTTCTTC TTGGACGGGA CATAACTGTT
10701  CCAGGAAAAG GAGGACTGGG TTTTAACCAC TGCACGACCA TCTGGCTCTC
10751  CCAAAAGCAG GATCATCTCT CCTCGGTAGT GCCTGGGCAT CCTGGAACTT
10801  ATGCAAAGAA AGTCCAACAT GGTGCTGGGT CTTGTTTAGT AAACTTGTTA
10851  CTTGGGGTGA AAAAAAAAAA AAAAAAA
```

Amino Acid Sequence

```
  1   MWPRLAFCCW GLALVSGWAT FQQMSPSRNF SFRLFPETAP GAPGSIPAPP
 51   APGDEAAGSR VERLGQAFRR RVRLLRELSE RLELVFLVDD SSSVGEVNFR
101   SELMFVRKLL SDFPVVPTAT RVAIVTFSSK NYVVPRVDYI STRRARQHKC
151   ALLLQEIPAI SYRGGGTYTK GAFQQAAQIL LHARENSTKV VFLITDGYSN
201   GGDPRPIAAS LRDSGVEIFT FGIWQGNIRE LNDMASTPKE EHCYLLHSFE
251   EFEALARRAL HEDLPSGSFI QDDMVHCSYL CDEGKDCCDR MGSCKCGTHT
301   GHFECICEKG YYGKGLQYEC TACPSGTYKP EGSPGGISSC IPCPDENHTS
```

Figure 1I

```
 351  PPGSTSPEDC VCREGYRASG QTCELVHCPA LKPPENGYFI QNTCNNHFNA
 401  ACGVRCHPGF DLVGSSIILC LPNGLWSGSE SYCRVRTCPH LRQPKHGHIS
 451  CSTREMLYKT TCLVACDEGY RLEGSDKLTC QGNSQWDGPE PRCVERHCST
 501  FQMPKDIIIS PHNCGKQPAK FGTICYVSCR QGFILSGVKE MLRCTTSGKW
 551  NVGVQAAVCK DVEAPQINCP KDIEAKTLEQ QDSANVTWQI PTAKDNSGEK
 601  VSVHVHPAFT PPYLFPVGDV AIVYTATDLS GNQASCIFHI KVIDAEPPVI
 651  DWCRSPPPVQ VSEKVHAASW DEPQFSDNSG AELVITRSHT QGDLFPQGET
 701  IVQYTATDPS GNNRTCDIHI VIKGSPCEIP FTPVNGDFIC TPDNTGVNCT
 751  LTCLEGYDFT EGSTDKYYCA YEDGVWKPTY TTEWPDCAKK RFANHGFKSF
 801  EMFYKAARCD DTDLMKKFSE AFETTLGKMV PSFCSDAEDI DCRLEENLTK
 851  KYCLEYNYDY ENGFAIGPGG WGAANRLDYS YDDFLDTVQE TATSIGNAKS
 901  SRIKRSAPLS DYKIKLIFNI TASVPLPDER NDTLEWENQQ RLLQTLETIT
 951  NKLKRTLNKD PMYSFQLASE ILIADSNSLE TKKASPFCRP GSVLRGRMCV
1001  NCPLGTYYNL EHFTCESCRI GSYQDEEGQL ECKLCPSGMY TEYIHSRNIS
1051  DCKAQCKQGT YSYSGLETCE SCPLGTYQPK FGSRSCLSCP ENTSTVKRGA
1101  VNISACGVPC PEGKFSRSGL MPCHPCPRDY YQPNAGKAFC LACPFYGTTP
1151  FAGSRSITEC SSFSSTFSAA EESVVPPASL GHIKKRHEIS SQVFHECFFN
1201  PCHNSGTCQQ LGRGYVCLCP LGYIGLKCET DIDECSPLPC LNNGVCKDLV
1251  GEFICECPSG YTGQRCEENI NECSSSPCLN KGICVDGVAG YRCTCVKGFV
1301  GLHCETEVNE CQSNPCLNNA VCEDQVGGFL CKCPPGFLGT RCGKNVDECL
1351  SQPCKNGATC KDGANSFRCL CAAGFTGSHC ELNINECQSN PCRNQATCVD
1401  ELNSYSCKCQ PGFSGKRCET EQSTGFNLDF EVSGIYGYVM LDGMLPSLHA
1451  LTCTFWMKSS DDMNYGTPIS YAVDNGSDNT LLLTDYNGWV LYVNGREKIT
1501  NCPSVNDGRW HHIAITWTSA NGIWKVYIDG KLSDGGAGLS VGLPIPGGGA
1551  LVLGQEQDKK GEGFSPAESF VGSISQLNLW DYVLSPQQVK SLATSCPEEL
1601  SKGNVLAWPD FLSGIVGKVK IDSKSIFCSD CPRLGGSVPH LRTASEDLKP
1651  GSKVNLFCDP GFQLVGNPVQ YCLNQGQWTQ PLPHCERISC GVPPPLENGF
1701  HSADDFYAGS TVTYQCNNGY YLLGDSRMFC TDNGSWNGVS PSCLDVDECA
```

Figure 1J

```
1751  VGSDCSEHAS CLNVDGSYIC SCVPPYTGDG KNCAEPIKCK APGNPENGHS
1801  SGEIYTVGAE VTFSCQEGYQ LMGVTKITCL ESGEWNHLIP YCKAVSCGKP
1851  AIPENGCIEE LAFTFGSKVT YRCNKGYTLA GDKESSCLAN SSWSHSPPVC
1901  EPVKCSSPEN INNGKYILSG LTYLSTASYS CDTGYSLQGP SIIECTASGI
1951  WDRAPPACHL VFCGEPPAIK DAVITGNNFT FRNTVTYTCK EGYTLAGLDT
2001  IECLADGKWS RSDQQCLAVS CDEPPIVDHA SPETAHRLFG DIAFYYCSDG
2051  YSLADNSQLL CNAQGKWVPP EGQDMPRCIA HFCEKPPSVS YSILESVSKA
2101  KFAAGSVVSF KCMEGFVLNT SAKIECMRGG QWNPSPMSIQ CIPVRCGFPP
2151  SIMNGYASGS NYSFGAMVAY SCNKGFYIKG EKKSTCEATG QWSSPIPTCH
2201  PVSCGEPPKV ENGFLEHTTG RIFESEVRYQ CNPGYKSVGS PVFVCQANRH
2251  WHSESPLMCV PLDCGKPPPI QNGFMKGENF EVGSKVQFFC NEGYELVGDS
2301  SWTCQKSGKW NKKSNPKCMP AKCPEPPLLE NQLVLKELTT EVGVVTFSCK
2351  EGHVLQGPSV LKCLPSQQWN DSFPVCKIVL CTPPPLISFG VPIPSSALHF
2401  GSTVKYSCVG GFFLRGNSTT LCQPDGTWSS PLPECVPVEC PQPEEIPNGI
2451  IDVQGLAYLS TALYTCKPGF ELVGNTTTLC GENGHWLGGK PTCKAIECLK
2501  PKEILNGKFS YTDLHYGQTV TYSCNRGFRL EGPSALTCLE TGDWDVDAPS
2551  CNAIHCDSPQ PIENGFVEGA DYSYGAIIIY SCFPGFQVAG HAMQTCEESG
2601  WSSSIPTCMP IDCGLPPHID FGDCTKLKDD QGYFEQEDDM MEVPYVTPHP
2651  PYHLGAVAKT WENTKESPAT HSSNFLYGTM VSYTCNPGYE LLGNPVLICQ
2701  EDGTWNGSAP SCISIECDLP TAPENGFLRF TETSMGSAVQ YSCKPGHILV
2751  GSDLRLCLEN RKWSGASPRC EAISCKKPNP VMNGSIKGSN YTYLSTLYYE
2801  CDPGYVLNGT ERRTCQDDKN WDEDEPICIP VDCSSPPVSA NGQVRGDEYT
2851  FQKEIEYTCN EGFLLEGARS RVCLANGSWS GATPDCVPVR CATPPQLANG
2901  VTEGLDYGFM KEVTFHCHEG YILHGAPKLT CQSDGNWDAE IPLCKPVNCG
2951  PPEDLAHGFP NGFSFIHGGH IQYQCFPGYK LHGNSSRRCL SNGSWSGSSP
3001  SCLPCRCSTP VIEYGTVNGT DFDCGKAARI QCFKGFKLLG LSEITCEADG
3051  QWSSGFPHCE HTSCGSLPMI PNAFISETSS WKENVITYSC RSGYVIQGSS
3101  DLICTEKGVW SQPYPVCEPL SCGSPPSVAN AVATGEAHTY ESEVKLRCLE
3151  GYTMDTDTDT FTCQKDGRWF PERISCSPKK CPLPENITHI LVHGDDFSVN
```

Figure 1K

```
3201   RQVSVSCAEG  YTFEGVNISV  CQLDGTWEPP  FSDESCSPVS  CGKPESPEHG

3251   FVVGSKYTFE  STIIYQCEPG  YELEGNRERV  CQENRQWSGG  VAICKETRCE

3301   TPLEFLNGKA  DIENRTTGPN  VVYSCNRGYS  LEGPSEAHCT  ENGTWSHPVP

3351   LCKPNPCPVP  FVIPENALLS  EKEFYVDQNV  SIKCREGFLL  QGHGIITCNP

3401   DETWTQTSAK  CEKISCGPPA  HVENAIARGV  HYQYGDMITY  SCYSGYMLEG

3451   FLRSVCLENG  TWTSPPICRA  VCRFPCQNGG  ICQRPNACSC  PEGWMGRLCE

3501   EPICILPCLN  GGRCVAPYQC  DCPPGWTGSR  CHTAVCQSPC  LNGGKCVRPN

3551   RCHCLSSWTG  HNCSRKRRTG  F*
```

FIGURE 2A

Map of Mouse C3b/C4b Complement Receptor Like cDNA (SEQ ID NO:3) and Amino Acid Sequences (SEQ ID NO:4)

cDNA Sequence

```
   1  CCCCGAGCTG CCAGAGGAGT CTGGATCGTG TCCCCAGTGT CACATGCAAG
  51  GACGCTGAGG TTCGCGGTTG CTACCCCGGG TCCCCTCCGC TTAGTTCGGG
 101  AACCTTGGCG CCTCTCTGCG CGCTCGGGGA CTGTCGCCTT GCACTCCCCG
 151  GGGCCACCGC TCGGTCCCCA GCGGGATGTG GTCGCGCCTG GCCTTTTGTT
 201  GCTGGGCTCT GGCACTGGTG TCGGGCTGGA CCAACTTCCA GCCCGTGGCC
 251  CCTTCGCTCA ACTTCAGCTT CCGCCTGTTC CCCGAGGCCT CTCCGGGGGC
 301  TCTGGGCAGA CTGGCGGTAC CTCCCGCGTC CAGTGAGGAG GAGGCAGCAG
 351  GGAGCAAAGT GGAGCGCCTG GGCCGCGCGT TCCGGAGCCG CGTGCGGCGA
 401  CTGCGGGAGC TCAGCGGCAG CCTGGAGCTC GTCTTCCTGG TGGACGAGTC
 451  GTCCAGCGTG GGCCAAACCA ACTTCCTCAA CGAGCTCAAG TTCGTGCGCA
 501  AGCTGCTGTC CGACTTCCCC GTGGTGTCCA CGGCCACGCG TGTGGCCATC
 551  GTCACCTTCT CATCCAAGAA CAACGTGGTG GCGCGCGTGG ATTACATCTC
 601  CACCAGCCGC GCGCACCAAC ACAAGTGCGC GCTGCTCAGC CGCGAGATCC
 651  CGGCCATCAC CTACCGCGGT GGTGGCACCT ATACCAAGGG CGCCTTCCAG
 701  CAAGCCGCGC AAATCCTTCG TCACTCTAGA GAAAACTCCA CCAAAGTCAT
 751  ATTTCTCATC ACCGACGGCT ATTCCAATGG CGGAGACCCC AGACCTATTG
 801  CAGCATCGCT TCGGGATTTC GGAGTGGAGA TCTTCACGTT CGGGATTTGG
 851  CAGGGGAATA TCCGGGAACT GAATGACATG GCTTCCACCC GAAGGAAGA
 901  ACATTGTTAC CTGCTCCACA GTTTTGAAGA ATTTGAGGCT TTAGCTCGCA
 951  GGGCGTTGCA TGAAGATCTA CCTTCTGGGA GTTTTATCCA AGAGGATATG
1001  GCCCACTGCT CTTATCTCTG TGAGGCTGGG AAAGACTGCT GTGACAGAAT
1051  GGCCAGCTGC AAATGTGGGA CACACACGGG TCAATTTGAA TGCATCTGTG
1101  AGAAGGGCTA TTACGGGAAA GGTCTGCAGC ATGAGTGCAC AGCTTGCCCA
1151  TCAGGGACAT ATAAGCCGGA AGCTTCTCCA GGAGGAATCA GCACCTGCAT
1201  CCCATGTCCT GACGTAAGCC ACACCTCCCC ACCTGGAAGC ACTTCCCCTG
1251  AAGACTGCGT GTGCCGAGAG GGATACCAGA GATCTGGCCA GACCTGTGAG
```

Figure 2B

```
1301  GTTGTCCACT GTCCTGCCCT GAAGCCTCCT GAAAATGGTT TTTTTATACA
1351  AAACACTTGC AAAAACTACT TCAATGCCGC CTGTGGGGTC CGATGTCGCC
1401  CGGGCTTTGA CCTTGTGGGA AGCAGCATCC ATTTGTGTCA ACCCAATGGT
1451  TTGTGGTCTG GGACAGAAAG CTTCTGCAGA GTGAGAACGT GCCCCCACCT
1501  CCGACAGCCC AAACACGGCC ACATCAGCTG CTCCACTGCG GAAATGTCCT
1551  ACAACACCCT GTGTTTGGTT ACCTGCAATG AAGGATACAG ATTAGAAGGC
1601  AGCACTAGGC TTACCTGTCA AGGAAATGCC CAGTGGGATG GCCCAGAGCC
1651  CCGGTGTGTA GAACGCCATT GTGCCACCTT CCAGAAGCCC AAAGGCGTCA
1701  TCATTTCTCC ACCCAGCTGC GGCAAGCAGC CCGCCAGGCC TGGGATGACC
1751  TGTCAGCTAA GCTGCCGCCA GGGATACATT TTATCCGGGG TCAGAGAAGT
1801  GAGATGTGCC ACATCTGGGA AGTGGAGTGC CAAAGTTCAG ACAGCTGTGT
1851  GCAAAGATGT GGAGGCTCCA CAAATCAGCT GTCCAAATGA CATTGAGGCA
1901  AAGACTGGGG AGCAGCAGGA CTCTGCTAAT GCCACCTGGC AAGTCCCAAC
1951  AGCTAAAGAC AACTCTGGTG AAAAGGTGTC AGTCCACGTC CACCCAGCCT
2001  TTACCCCACC TTACCTCTTC CCAATTGGAG ACGTGGCCAT CACCTACACG
2051  GCAACCGACT CATCCGGTAA CCAAGCCAGC TGCACTTTCT ACATTAAGGT
2101  CATTGATGTG GAACCGCCTG TCATAGATTG GTGCCGATCT CCACCTCCAA
2151  TCCAGGTCGT AGAGAAGGAG CACCCTGCAA GCTGGGATGA GCCTCAGTTC
2201  TCAGACAACT CCGGGGCTGA ATTGGTCATT ACCAGCAGTC ACACACAAGG
2251  CGACATGTTT CCTCATGGGG AAACGGTGGT GTGGTACACA GCCACTGACC
2301  CCTCAGGCAA CAACAGGACC TGTGACATCC ACATTGTCAT AAAAGGTTCT
2351  CCCTGTGAGG TCCCCTTCAC CCCTGTAAAC GGGGACTTTA TCTGTGCCCA
2401  GGATAGTGCT GGAGTTAACT GTAGCCTGAG CTGCAAGGAG GGCTATGATT
2451  TCACAGAAGG GTCACCTGAG AAGTACTACT GTGCTTTTGA AGATGGTATC
2501  TGGAGACCAC CATACTCTAC AGAATGGCCA GACTGTGCTA TAAAACGTTT
2551  TGCAAACCAT GGTTTCAAGT CCTTTGAAAT GCTATACAAA ACCACTCGCT
2601  GTGATGACAT GGATCTGTTT AAGAAGTTTT CTGCAGCATT TGAGACTACC
2651  CTGGGGAACA TGGTCCCGTC CTTTTGTAAC GATGCTGATG ACATTGACTG
```

Figure 2C

```
2701   CAGACTGGAG GACCTGACCA AAAAATACTG CATCGAGTAT AATTACAACT
2751   ATGAAAATGG CTTTGCAATT GGACCAGGAG GCTGGGGTGC AGGCAACAGG
2801   CTGGATTATT CCTACGATCA CTTCCTGGAT GTTGTACAGG AAACACCCAC
2851   CGATGTGGGC AAGGCCAGAT CGTCACGGAT TAAAAGAACT GTCCCATTGT
2901   CTGACCCCAA AATTCAGCTA ATTTTTAACA TCACAGCTAG CGTGCCACTC
2951   CCAGAGGAAA GAAACGATAC CCTTGAATTG GAGAATCAGC AGCGACTCAT
3001   TAAGACATTG GAAACAATCA CCAATCGCCT GAAAAGCACC TTGAATAAAG
3051   AGCCCATGTA TTCTTTCCAG CTCGCCTCGG AAACAGTGGT GGCTGACAGC
3101   AATTCCCTCG AAACAGAAAA GGCTTTTCTC TTCTGCAGAC CAGGCTCTGT
3151   GCTGAGGGGG CGCATGTGTG TCAACTGCCC CCTGGGAACC TCTTACTCTC
3201   TGGAGCATTC CACCTGTGAA AGCTGCCTCA TGGGATCCTA CCAAGATGAA
3251   GAAGGGCAGC TGGAATGCAA GCTCTGTCCC CCAAGGACTC ACGCGGAATA
3301   CCTCCATTCA AGAAGCGTCT CTGAATGCAA AGCTCAGTGT AAGCAAGGCA
3351   CCTACTCTTC CAGTGGGCTG GAGACCTGCG AATCGTGTCC GCTGGGTACT
3401   TATCAACCGG AATTTGGATC CCGGAGCTGC CTCCTATGCC CAGAAACCAC
3451   CACAACGGTG AAAAGAGGAG CCGTGGACAT CTCTGCTTGT GGAGTGCCCT
3501   GCCCAGTAGG AGAATTCTCC CGTTCTGGGC TAACACCCTG CTACCCTTGC
3551   CCTCGAGACT ATTACCAACC CAATGCAGGG AAGTCCTTCT GCCTCGCTTG
3601   TCCCTTTTAT GGAACTACAA CCATCACTGG CGCCACGTCC ATCACAGACT
3651   GCTCAAGTTT TAGCTCTACT TTCTCAGCAG CAGAAGAAAG CATAGTGCCC
3701   CTCGTGGCCC CTGGACATTC CAGAACAAG TACGAAGTCA GCAGTCAGGT
3751   CTTTCACGAA TGCTTCTTAA ACCCCTGCCA CAACAGTGGA ACCTGCCAAC
3801   AGCTTGGGCG TGGTTATGTC TGTCTCTGCC CACCTGGATA CACAGGCTTA
3851   AAGTGTGAAA CAGATATTGA TGAATGCAGC TCTCTGCCTT GCCTCAATGG
3901   TGGAATTTGT AGAGACCAAG TTGGGGGATT CACGTGCGAA TGTTCATTGG
3951   GCTATTCAGG TCAAATATGT GAAGAAAATA TAAATGAGTG TATCTCCAGC
4001   CCTTGCTTAA ATAAAGGAAC CTGCACTGAC GGCTTGGCAA GCTACCGCTG
4051   TACCTGTGTG AAAGGATACA TGGGTGTGCA CTGTGAAACA GACGTCAATG
4101   AATGCCAGTC AAGCCCCTGC TTAAACAACG CAGTTTGTAA AGACCAAGTT
```

Figure 2D

```
4151    GGGGGGGTTCT CGTGCAAATG CCCACCCGGA TTTTTGGGTA CTCGGTGTGA
4201    AAAAAATGTG GATGAGTGTC TCAGTCAGCC ATGCCAAAAT GGAGCCACTT
4251    GTAAGGATGG TGCCAACAGC TTCAGGTGTC AATGTCCAGC AGGCTTCACA
4301    GGGACACACT GTGAACTGAA CATCAACGAG TGTCAGTCCA ACCCGTGTAG
4351    GAACCAGGCC ACCTGTGTGG ATGAACTAAA CTCATACAGT TGTAAATGTC
4401    AGCCAGGATT TTCAGGCCAC AGGTGTGAGA CAGAACAGCC TTCCGGTTTT
4451    AACCTGGATT TTGAAGTTTC TGGCATCTAC GGGTACGTCC TGCTAGATGG
4501    AGTGCTGCCA ACCCTCCATG CCGTAACCTG CGCATTCTGG ATGAAATCCT
4551    CTGATGTCAT CAACTACGGG ACGCCCATCT CCTATGCACT TGAGGATGAC
4601    AAAGACAACA CCTTCCTCCT GACTGATTAC AACGGCTGGG TTCTTTATGT
4651    GAATGGAAAG GAAAAGATCA CCAACTGCCC CTCCGTAAAT GATGGCATTT
4701    GGCATCATAT TGCAATCACA TGGACAAGTA TTGGTGGAGC CTGGAGGGTC
4751    TATATAGATG GGGAATTATC TGACGGTGGT ACTGGCCTCT CCATTGGCAA
4801    AGCCATACCT GGTGGCGGTG CATTAGTTCT TGGCAAGAG CAAGACAAAA
4851    AAGGAGAGGG GTTCAACCCG GCTGAGTCTT TTGTGGGCTC CATAAGCCAG
4901    CTCAACCTCT GGGACTATGT CCTGTCTCCA CAGCAGGTGA AGTTGCTGGC
4951    CAGCTCCTGC CCAGAGGAAC TGAGTCGGGG AAACGTGTTA GCATGGCCCG
5001    ATTTCCTGTC GGGAATCACG GGGAAGGTGA AGGTTGATTC CAGCAGCATG
5051    TTCTGCTCTG ATTGTCCGTC TTTAGAAGGA TCCGTGCCTC ACCTGAGACC
5101    TGCATCAGGA AATCGAAAGC CAGGCTCCAA AGTCAGTCTG TTCTGTGATC
5151    CGGGCTTCCA GATGGTTGGG AATCCTGTGC AGTATTGTCT GAACCAAGGG
5201    CAGTGGACAC AACCACTCCC CCACTGTGAA CGCATTCGCT GTGGGCTGCC
5251    TCCCGCCTTG GAGAATGGCT TCTACTCAGC CGAGGACTTC CATGCGGGCA
5301    GCACGGTGAC CTATCAGTGC ACCAGTGGCT ACTACCTGCT GGGTGATTCC
5351    CGAATGTTCT GCRCAGACAA CGGGAGCTGG AACGGCATTT CACCATCCTG
5401    TCTCGATGTC GATGAGTGTG CAGTCGGCTC GGACTGTAGT GAGCACGCCT
5451    CCTGCCTGAA CACCAACGGA TCCTACGTAT GCTCCTGTAA CCCACCATAC
5501    ACGGGAGATG GGAAAAACTG TGCAGAACCT GTAAAATGTA AGGCTCCAGA
```

Figure 2E

```
5551  AAATCCAGAA AATGGCCGCT CTTCTGGCGA GATTTACACC GTGGGTACTG
5601  CAGTCACATT TTCCTGTGAC GAAGGGCACG AGCTGGTGGG AGTGAGCACC
5651  ATCACGTGTT TGGAGACTGG CGAGTGGGAT CGCCTCAGGC CGTCCTGTGA
5701  AGCCATTTCC TGTGGTGTCC CACCTGTTCC TGAAAATGGT GGTGTTGACG
5751  GGTCGGCATT CACATATGGC AGTAAGGTGG TGTACAGGTG TGATAAAGGA
5801  TATACTTTGT CTGGGGATGA AGAGTCAGCA TGCCTTGCTA GTGGTTCCTG
5851  GAGTCATTCC TCTCCTGTGT GCGGGCTAGT GAAGTGTTCC CAGCCTGAGG
5901  ACATAAATAA CGGCAAATAC ATCTTAAGTG GCTCACCTA CCTTTCTATT
5951  GCATCGTACT CCTGTGAGAA CGGATACAGT TTACAGGGCC CATCCCTCCT
6001  TGAATGCACA GCTTCCGGCA GCTGGGACAG AGCGCCACCT AGCTGTCAAC
6051  TTGTCTCCTG CGGAGAGCCT CCAATCGTCA AGATGCTGT CATCACTGGG
6101  AGCAACTTCA CTTTTGGGAA CACAGTTGCT TACACATGCA AAGAGGGCTA
6151  CACCCTTGCT GGGCCTGACA CCATCATATG CCAGGCCAAC GGCAAATGGA
6201  ATTCAAGTAA CCACCAGTGC CTGGCTGTCT CCTGTGACGA GCCCCCCAAT
6251  GTGGACCACG CCTCTCCAGA GACTGCTCAC AGGCTCTTTG GAGACACCGC
6301  GTTTTACTAC TGTGCGGATG GCTACAGCCT GGCTGATAAT TCCCAGCTCA
6351  TCTGCAATGC CCAGGGGAAC TGGGTTCCCC CCGCGGGCCA GGCTGTGCCG
6401  CGCTGCATAG CTCACTTCTG TGAAAAACCC CCATCTGTTT CCTACAGCAT
6451  CTTGGAATCT GTGAGCAAAG CAAAGTTTGC AGCTGGCTCG GTAGTGAGCT
6501  TCAAGTGCAT GGAGGGTTTT GTGCTGAACA CCTCAGCGAA GATTGAATGC
6551  CTGAGAGGTG GAGAGTGGAG CCCTTCTCCC CTCTCGGTCC AGTGCATCCC
6601  GGTGCGATGC GGAGAGCCTC CAAGCATCGC AAATGGCTAC CCGAGTGGGA
6651  CAAACTACAG TTTTGGGGCC GTGGTGGCCT ACAGCTGCCA CAAGGGATTC
6701  TATATCAAGG GGGAGAAGAA GAGCACGTGT GAGGCCACAG ACAGTGGAG
6751  TAAACCCACG CCCACCTGCC ATCCTGTGTC CTGTAACGAG CCACCTAAGG
6801  TTGAGAACGG CTTCCTGGAG CACACCACTG GCAGGACCTT TGAGAGCGAA
6851  GCAAGGTTCC AGTGCAACCC AGGCTATAAG GCAGCCGGAA GTCCTGTGTT
6901  TGTTTGCCAA GCCAATCGCC ACTGGCACAG CGACGCCCCT CTGTCCTGCA
6951  CCCCTCTCAA CTGTGGGAAA CCCCCTCCCA TTCAGAATGG CTTTTTGAAA
```

Figure 2F

```
7001  GGAGAAAGCT TTGAAGTAGG GTCCAAGGTT CAGTTTGTCT GTAATGAGGG
7051  ATATGAGCTC GTTGGTGATA ATTCTTGGAC TTGCCAGAAA TCTGGCAAAT
7101  GGAGTAAGAA GCCAAGCCCG AAGTGTGTCC CCACCAAGTG TGCAGAGCCT
7151  CCTCTCTTAG AAAACCAGCT CGTATTGAAG GAATTAGCTT CCGAGGTAGG
7201  AGTGATGACC ATTTCCTGTA AAGAGGGCA TGCCTTGCAA GGCCCCTCTG
7251  TCCTGAAGTG CTTGCCATCC GGGCAATGGA ATGGTTCCTT TCCTATTTGT
7301  AAGATGGTCC TTTGTCCCTC GCCTCCCTTG ATTCCCTTCG GCGTCCCTGC
7351  GTCTTCCGGT GCTCTTCATT TTGGCAGTAC TGTCAAGTAT CTGTGTGTCG
7401  ACGGGTTTTT CTTAAGAGGC AGTCCAACCA TCCTCTGCCA GGCTGATAGC
7451  ACCTGGAGTT CTCCATTGCC CGAATGCGTT CCGGTAGAAT GTCCCCAACC
7501  TGAGGAGATC CTCAACGGTA TCATCCACGT ACAAGGGCTT GCCTATCTCA
7551  GCACCACGCT CTACACCTGC AAGCCAGGCT TTGAGTTAGT GGGCAATGCT
7601  ACCACCCTCT GTGGGGAAAA TGGCCAGTGG CTCGGAGGAA AACCAATGTG
7651  CAAACCCATT GAATGCCCAG AGCCCAAGGA GATTTTAAAT GGCCAATTCT
7701  CTTCCGTGAG CTTTCAGTAT GGACAAACCA TCACATACTT TTGTGACCGG
7751  GGCTTCCGGC TCGAAGGTCC CAAATCCCTG ACCTGTTTAG AGACAGGTGA
7801  CTGGGATATG GATCCCCCCT CTTGTGATGC CATCCACTGC AGTGACCCAC
7851  AGCCCATTGA AAATGGTTTC GTAGAAGGTG CGGATTACAG ATACGGTGCC
7901  ATGATCATCT ATAGCTGCTT CCCTGGGTTT CAGGTGCTTG GTCATGCCAT
7951  GCAGACCTGT GAAGAGTCGG GATGGTCAAG CTCCAGCCCA ACCTGTGTAC
8001  CCATAGACTG CGGTCTCCCT CCTCACATAG ACTTTGGTGA CTGTACTAAA
8051  GTCAGAGATG GCCAGGGACA TTTTGATCAA GAAGATGACA TGATGGAAGT
8101  CCCATATCTG GCTCACCCTC AACATTTGGA AGCAACAGCT AAGGCCTTGG
8151  AAAATACAAA GGAGTCGCCT GCCTCACATG CATCCCACTT CCTCTATGGC
8201  ACGATGGTTT CCTACAGCTG CGAGCCTGGT TATGAACTGC TGGGAATCCC
8251  TGTGCTGATC TGCCAGGAAG ATGGTACGTG GAATGGTACC GCACCCTCTT
8301  GCATTTCCAT TGAATGTGAT TTGCCTGTTG CTCCCGAAAA TGGCTTTTTA
8351  CATTTCACAC AGACGACTAT GGGCAGTGCT GCACAATATA GCTGCAAGCC
```

Figure 2G

```
8401  GGGGCACATT CTAGAAGGCT CCCACTTAAG ACTCTGTCTG CAGAATAAGC
8451  AGTGGAGTGG CACTGTTCCA CGCTGTGAAG CCATCTCATG CAGTAAGCCA
8501  AACCCACTCT GGAATGGATC CATCAAAGGA GATGACTACT CCTACCTGGG
8551  TGTGTTATAC TACGAGTGTG ACTCTGGCTA TATTCTCAAT GGCTCTAAGA
8601  AGAGGACATG CCAAGAAAAT AGAGATTGGG ATGGGCATGA GCCCATGTGT
8651  ATTCCTGTAG ACTGTGGCTC ACCCCAGTC CCCACCAATG GCCGAGTGAA
8701  GGGAGAAGAA TACACATTCC AAAAGGAGAT TACATACTCT TGCCGTGAAG
8751  GGTTCATACT GGAAGGAGCC AGGAGTCGTA TCTGTCTTAC CAATGGAAGT
8801  TGGAGTGGTG CCACTCCCAG CTGCATGCCT GTTAGATGTC CTGCCCCACC
8851  ACAGGTGCCA AATGGGGTGG CAGATGGCCT AGACTATGGG TTCAAGAAGG
8901  AAGTAGCGTT CCACTGTCTA GAGGGCTATG TGCTGCAGGG GGCTCCAAGA
8951  CTCACCTGTC AGTCCAATGG GACTTGGGAT GCAGAAGTCC CTGTCTGTAA
9001  ACCAGCTACC TGTGGTCCTC CTGCCGACCT TCCCCAGGGC TTCCCTAATG
9051  GCTTTTCTTT TTATCATGGG GGCCACATAC AGTATCAGTG TTTTACTGGT
9101  TATAAGCTTC ATGGAAACCC ATCAAGAAGA TGCCTTCCCA ATGGTCCTG
9151  GAGCGGCAGC TCGCCATCCT GCCTACCTTG CAGGTGTTCC ACACCCATCA
9201  TTCAACAGGG AACCATCAAC GCAACTGATT TGGGATGTGG AAAGACGGTC
9251  CAGATTGAGT GCTTCAAAGG CTTCAAGCTG CTTGGACTTT CTGAAATCAC
9301  CTGTGATGCC AATGGCCAAT GGTCTGACGT CCCACTGTGT GAGCACGCTC
9351  AGTGCGGGCC TCTCCCAACC ATACCCAACG CAATTGTCCT TGAGGGCAGC
9401  CTTTCGGAGG ACAATGTGGT AACTTACAGC TGCAGACCTG GCTACACCAT
9451  GCAAGGTAGT TCAGATCTGA TTTGTACGGA AAAAGCGATA TGGAGCCAGC
9501  CTTACCCAAC GTGTGAACCC CTGTCCTGTG GACCCCCACC AACTGTAGCC
9551  AATGCAGTGG CAACAGGAGA GGCTCATACC TATGAAAGCA AGTGAAACT
9601  CAGGTGTCTG GAAGGGTATG TGATGGATTC GGATACAGAT ACATTCACCT
9651  GCCAGCAAGA TGGCCATTGG GTCCCTGAAA GAATCACCTG CAGTCCTAAA
9701  AAATGCCCTG TGCCATCCAA CATGACACGC ATACGTTTTC ACGGAGATGA
9751  CTTCCAGGTG AACAGACAAG TTTCTGTGTC ATGTGCAGAA GGGTTTACCC
9801  ACGAAGGAGT GAACTGGTCA ACATGCCAGC CGACGGTAC ATGGGAGCCA
```

Figure 2H

```
 9851  CCATTTTCTG ATGAATCCTG TATCCCAGTT GTTTGTGGGC ATCCTGAAAG
 9901  CCCAGCGCAT GGCTCCGTGG TTGGCAATAA GCACAGCTTT GGAAGCACCA
 9951  TTGTTTACCA GTGTGACCCT GGCTACAAAT TAGAGGGAA CAGGGAACGA
10001  ATCTGCCAGG AGAACAGACA GTGGAGTGGA GAGGTGGCAG TGTGCAGAGA
10051  GAACAGATGT GAGACTCCAG CTGAGTTTCC AATGGGAAG GCTGTCTTGG
10101  AAAACACCAC ATCTGGACCC AGCCTTCTGT TTTCCTGTCA CAGAGGCTAC
10151  ACCCTGGAAG GGTCCCCCGA GGCACACTGC ACTGCAAATG GAACCTGGAA
10201  TCACCTGACT CCCCTCTGCA AACCAAATCC ATGCCCTGTC CCTTTTGTGA
10251  TTCCTGAGAA CGCCGTCCTT TCTGAAAAAG AGTTTTATGT CGACCAGAAT
10301  GTATCTATCA AGTGCAGGGA AGGCTTCCTG CTCAAAGGCA ATGGTGTCAT
10351  CACGTGCAGC CCTGACGAGA CATGGACGCA CACCAATGCC AGATGTGAAA
10401  AAATCTCCTG TGGTCCTCCA AGTCACGTAG AGAATGCAAT TGCTCGAGGA
10451  GTGTATTACC AGTATGGGGA CATGATCACC TACTCCTGTT ACAGTGGCTA
10501  CATGCTAGAA GGTTCCCTCC GGAGTGTTTG CCTAGAAAAT GGAACATGGA
10551  CACCATCTCC TGTTTGCAGA GCTGTCTGTC GGTCCCATG TCAGAATGGA
10601  GGTGTCTGTC AACGTCCAAA TGCTTGCTCA TGCCCAGACG GCTGGATGGG
10651  ACGTCTCTGT GAAGAGCCAA TATGCATACT CCCCTGTTTG AATGGTGGGC
10701  GCTGTGTGGC CCCTTATCAG TGTGACTGCC CCACAGGCTG GACTGGGTCC
10751  CGCTGTCATA CAGCTACTTG TCAGTCCCCC TGCTTAAATG GCGGGAAATG
10801  CATAAGACCA AACCGATGCC ATTGTCTCTC AGCCTGGACA GGACATGATT
10851  GTTCCAGGAA AAGGAGAGCC GGGCTTTGAT CTCATGCCCC ACCCCCTCTC
10901  CCTAAGCAGC ATCATCTCCT TCCGGTAGCT CCTGGGACTC CCACCAAGAA
10951  AGACCAACGC GGTGCTGGGG CTTGTTTGGT TTTATAAGCT TGAGGTTGAC
11001  TTTTTAATTT TGTGATCTAT TTTGTTAAAT TTTTTTGTGA CGTCCTTTCT
11051  TACATGTGTG CGTTGTTTAA ATATGCTTGC ATTTTCTATA TAAAATTTAT
11101  ATTAAACGGA CGCACTTCAT CCTCACCAGA TGTACATACT CTGCTGTCTG
11151  CTGGGAAAGC CCCTGGAATA CATTTTTATT CAATTACTTA AAGATGACTT
11201  TCCATTAAAA TATATTTTGC TACTAAAAAA
```

Figure 21

Amino Acid Sequence

```
   1  *FGNLGASLR  ARGLSPCTPR  GHRSVPSGMW  SRLAFCCWAL  ALVSGWTNFQ
  51  PVAPSLNFSF  RLFPEASPGA  LGRLAVPPAS  SEEEAAGSKV  ERLGRAFRSR
 101  VRRLRELSGS  LELVFLVDES  SSVGQTNFLN  ELKFVRKLLS  DFPVVSTATR
 151  VAIVTFSSKN  NVVARVDYIS  TSRAHQHKCA  LLSREIPAIT  YRGGGTYTKG
 201  AFQQAAQILR  HSRENSTKVI  FLITDGYSNG  GDPRPIAASL  RDFGVEIFTF
 251  GIWQGNIREL  NDMASTPKEE  HCYLLHSFEE  FEALARRALH  EDLPSGSFIQ
 301  EDMAHCSYLC  EAGKDCCDRM  ASCKCGTHTG  QFECICEKGY  YGKGLQHECT
 351  ACPSGTYKPE  ASPGGISTCI  PCPDVSHTSP  PGSTSPEDCV  CREGYQRSGQ
 401  TCEVVHCPAL  KPPENGFFIQ  NTCKNYFNAA  CGVRCRPGFD  LVGSSIHLCQ
 451  PNGLWSGTES  FCRVRTCPHL  RQPKHGHISC  STAEMSYNTL  CLVTCNEGYR
 501  LEGSTRLTCQ  GNAQWDGPEP  RCVERHCATF  QKPKGVIISP  PSCGKQPARP
 551  GMTCQLSCRQ  GYILSGVREV  RCATSGKWSA  KVQTAVCKDV  EAPQISCPND
 601  IEAKTGEQQD  SANATWQVPT  AKDNSGEKVS  VHVHPAFTPP  YLFPIGDVAI
 651  TYTATDSSGN  QASCTFYIKV  IDVEPPVIDW  CRSPPPIQVV  EKEHPASWDE
 701  PQFSDNSGAE  LVITSSHTQG  DMFPHGETVV  WYTATDPSGN  NRTCDIHIVI
 751  KGSPCEVPFT  PVNGDFICAQ  DSAGVNCSLS  CKEGYDFTEG  SPEKYYCAFE
 801  DGIWRPPYST  EWPDCAIKRF  ANHGFKSFEM  LYKTTRCDDM  DLFKKFSAAF
 851  ETTLGNMVPS  FCNDADDIDC  RLEDLTKKYC  IEYNYNYENG  FAIGPGGWGA
 901  GNRLDYSYDH  FLDVVQETPT  DVGKARSSRI  KRTVPLSDPK  IQLIFNITAS
 951  VPLPEERNDT  LELENQQRLI  KTLETITNRL  KSTLNKEPMY  SFQLASETVV
1001  ADSNSLETEK  AFLFCRPGSV  LRGRMCVNCP  LGTSYSLEHS  TCESCLMGSY
1051  QDEEGQLECK  LCPPRTHAEY  LHSRSVSECK  AQCKQGTYSS  SGLETCESCP
1101  LGTYQPEFGS  RSCLLCPETT  TTVKRGAVDI  SACGVPCPVG  EFSRSGLTPC
1151  YPCPRDYYQP  NAGKSFCLAC  PFYGTTTITG  ATSITDCSSF  SSTFSAAEES
1201  IVPLVAPGHS  QNKYEVSSQV  FHECFLNPCH  NSGTCQQLGR  GYVCLCPPGY
1251  TGLKCETDID  ECSSLPCLNG  GICRDQVGGF  TCECSLGYSG  QICEENINEC
1301  ISSPCLNKGT  CTDGLASYRC  TCVKGYMGVH  CETDVNECQS  SPCLNNAVCK
1351  DQVGGFSCKC  PPGFLGTRCE  KNVDECLSQP  CQNGATCKDG  ANSFRCQCPA
```

Figure 2J

```
1401    GFTGTHCELN  INECQSNPCR  NQATCVDELN  SYSCKCQPGF  SGHRCETEQP

1451    SGFNLDFEVS  GIYGYVLLDG  VLPTLHAVTC  AFWMKSSDVI  NYGTPISYAL

1501    EDDKDNTFLL  TDYNGWVLYV  NGKEKITNCP  SVNDGIWHHI  AITWTSIGGA

1551    WRVYIDGELS  DGGTGLSIGK  AIPGGGALVL  GQEQDKKGEG  FNPAESFVGS

1601    ISQLNLWDYV  LSPQQVKLLA  SSCPEELSRG  NVLAWPDFLS  GITGKVKVDS

1651    SSMFCSDCPS  LEGSVPHLRP  ASGNRKPGSK  VSLFCDPGFQ  MVGNPVQYCL

1701    NQGQWTQPLP  HCERIRCGLP  PALENGFYSA  EDFHAGSTVT  YQCTSGYYLL

1751    GDSRMFCXDN  GSWNGISPSC  LDVDECAVGS  DCSEHASCLN  TNGSYVCSCN

1801    PPYTGDGKNC  AEPVKCKAPE  NPENGRSSGE  IYTVGTAVTF  SCDEGHELVG

1851    VSTITCLETG  EWDRLRPSCE  AISCGVPPVP  ENGGVDGSAF  TYGSKVVYRC

1901    DKGYTLSGDE  ESACLASGSW  SHSSPVCGLV  KCSQPEDINN  GKYILSGLTY

1951    LSIASYSCEN  GYSLQGPSLL  ECTASGSWDR  APPSCQLVSC  GEPPIVKDAV

2001    ITGSNFTFGN  TVAYTCKEGY  TLACPDTIIC  QANGKWNSSN  HQCLAVSCDE

2051    PPNVDHASPE  TAHRLFGDTA  FYYCADGYSL  ADNSQLICNA  QGNWVPPAGQ

2101    AVPRCIAHFC  EKPPSVSYSI  LESVSKAKFA  AGSVVSFKCM  EGFVLNTSAK

2151    IECLRGGEWS  PSPLSVQCIP  VRCGEPPSIA  NGYPSGTNYS  FGAVVAYSCH

2201    KGFYIKGEKK  STCEATGQWS  KPTPTCHPVS  CNEPPKVENG  FLEHTTGRTF

2251    ESEARFQCNP  GYKAAGSPVF  VCQANRHWHS  DAPLSCTPLN  CGKPPPIQNG

2301    FLKGESFEVG  SKVQFVCNEG  YELVGDNSWT  CQKSGKWSKK  PSPKCVPTKC

2351    AEPPLLENQL  VLKELASEVG  VMTISCKEGH  ALQGPSVLKC  LPSGQWNGSF

2401    PICKMVLCPS  PPLIPFGVPA  SSGALHFGST  VKYLCVDGFF  LRGSPTILCQ

2451    ADSTWSSPLP  ECVPVECPQP  EEILNGIIHV  QGLAYLSTTL  YTCKPGFELV

2501    GNATTLCGEN  GQWLGGKPMC  KPIECPEPKE  ILNGQFSSVS  FQYGQTITYF

2551    CDRGFRLEGP  KSLTCLETGD  WDMDPPSCDA  IHCSDPQPIE  NGFVEGADYR

2601    YGAMIIYSCF  PGFQVLGHAM  QTCEESGWSS  SSPTCVPIDC  GLPPHIDFGD

2651    CTKVRDGQGH  FDQEDDMMEV  PYLAHPQHLE  ATAKALENTK  ESPASHASHF

2701    LYGTMVSYSC  EPGYELLGIP  VLICQEDGTW  NGTAPSCISI  ECDLPVAPEN

2751    GFLHFTQTTM  GSAAQYSCKP  GHILEGSHLR  LCLQNKQWSG  TVPRCEAISC

2801    SKPNPLWNGS  IKGDDYSYLG  VLYYECDSGY  ILNGSKKRTC  QENRDWDGHE
```

Figure 2K

```
2851  PMCIPVDCGS PPVPTNGRVK GEEYTFQKEI TYSCREGFIL EGARSRICLT

2901  NGSWSGATPS CMPVRCPAPP QVPNGVADGL DYGFKKEVAF HCLEGYVLQG

2951  APRLTCQSNG TWDAEVPVCK PATCGPPADL PQGFPNGFSF YHGGHIQYQC

3001  FTGYKLHGNP SRRCLPNGSW SGSSPSCLPC RCSTPIIQQG TINATDLGCG

3051  KTVQIECFKG FKLLGLSEIT CDANGQWSDV PLCEHAQCGP LPTIPNAIVL

3101  EGSLSEDNVV TYSCRPGYTM QGSSDLICTE KAIWSQPYPT CEPLSCGPPP

3151  TVANAVATGE AHTYESKVKL RCLEGYVMDS DTDTFTCQQD GHWVPERITC

3201  SPKKCPVPSN MTRIRFHGDD FQVNRQVSVS CAEGFTHEGV NWSTCQPDGT

3251  WEPPFSDESC IPVVCGHPES PAHGSVVGNK HSFGSTIVYQ CDPGYKLEGN

3301  RERICQENRQ WSGEVAVCRE NRCETPAEFP NGKAVLENTT SGPSLLFSCH

3351  RGYTLEGSPE AHCTANGTWN HLTPLCKPNP CPVPFVIPEN AVLSEKEFYV

3401  DQNVSIKCRE GFLLKGNGVI TCSPDETWTH TNARCEKISC GPPSHVENAI

3451  ARGVYYQYGD MITYSCYSGY MLEGSLRSVC LENGTWTPSP VCRAVCRFPC

3501  QNGGVCQRPN ACSCPDGWMG RLCEEPICIL PCLNGGRCVA PYQCDCPTGW

3551  TGSRCHTATC QSPCLNGGKC IRPNRCHCLS AWTGHDCSRK RRAGL*
```

FIGURE 3A
Comparison of Human AGP-03144-a1 (top; amino acids 1251-1372 of SEQ ID
NO:2) and Human C3b/C4b Complement Receptor (Bottom; SEQ ID NO: 5)
Amino Acid Sequence

```
1251 GEFICECPSGYTGQRCEENINECSSSPCLNKGICVDGVAGYRCTCVKGFV 1300
                                                   |  |
   1 .........................................MGASSPRSPEPV  12

1301 GLHCETEVNECQSNPCLNNAVCEDQVGGFLCKCPPGFLGTRCGKNVDE..  1348
      |         |   .        |   |   |      |    ||
  13 GPPAPGLPFCCGGSLLAVVVLLALPVAWGQCNAPEWLPFARPTNLTDEFE  62

1349 .....CLSQPCKNGATCKDGANSFRCLCAAGFTGSHCELNINECQSNPCR 1393
          |. |: |. :   |  ||  .||.    .|.    ||
  63 FPIGTYLNYECRPGYSGR..PFSIICLKNSVWTGAK.....DRCRRKSCR 105

1394 NQATCVDELNSYSCKCQPGFSGKRCETEQSTGFNLDFEVSG...IYG.YV 1439
      |    | .|    .  |..   .|:|    |   ||| |
 106 NPP...DPVNGMVHVIKGIQFGSQIKYSCTKGYRLIGSSSATCIISGDTV 152

1440 MLDGMLPSLHALTC.........TFWMKSSDDMNYGTPISYAVDNGSDNT 1480
      . |   | :  |           | .:..||. :.|   . ||
 153 IWDNETPICDRIPCGLPPTITNGDFISTNRENFHYGSVVTYRCNPGSGGR 202

1481 LLLTDYNGWVLYVNGREKITNCPSVND..GRWHHIAITWTSANGIWKVYI 1528
        | . |   | | | .| | |    |              :
 203 K........VFELVGEPSI.YCTSNDDQVGIWSGPAPQCIIPNKCTPPNV 243

1529 DGKL..SDGGAGLSVG..LPIPGGGALVLGQEQDKKGEGFSPAESFVGSI 1574
      :  :  ||  .|.       |:   .|   :   | .|
 244 ENGILVSDNRSLFSLNEVVEFRCQPGFVMKGPRRVKCQALNKWEPELPSC 293

1575 SQLNLWDYVLSPQQVKSLATSCPEE.LSKGNVLAW...PDF.LSGIV... 1616
      |..      |  .   |  .: |  |  .:    |:|  |
 294 SRV....CQPPPDVLHAERTQRDKDNFSPGQEVFYSCEPGYDLRGAASMR 339

1617 ....GKVKIDSKSIFCSDCPRLGGSVPHLRTA.SEDLKPGSKVNLFCDPG 1661
         |        ..   |    |..|    .|. |.||. |||
 340 CTPQGDWSPAAPTCEVKSCDDFMGQLLNGRVLFPVNLQLGAKVDFVCDEG 389

1662 FQLVGNPVQYCLNQGQ...WTQPLPHCERISCGVPPPLENGFHSA...DD 1705
     |||  |.  ||.  |  |   .| ||.| ||  || | .| |.      :
 390 FQLKGSSASYCVLAGMESLWNSSVPVCEQIFCPSPPVIPNGRHTGKPLEV 439

1706 FYAGSTVTYQCN......NGYYLLGDSRMFCTD....NGSWNGVSPSCLD 1745
     |  | | |.       : |:|:|  .|| ||    || |. .|  |
 440 FPFGKAVNYTCDPHPDRGTSFDLIGESTIRCTSDPQGNGVWSSPAPRCGI 489

1746 VDECAVGS.......DCSEHASCLNVDGSYICSCVPPYTG.......... 1778
      . |        .||  :  |   ||||
 490 LGHCQAPDHFLFAKLKTQTNASDFPIGTSLKYECRPEYYGRPFSITCLDN 539

1779 ....DGKNCAEPIKCKAPGNPENG..HSSGEIYTVGAEVTFSCQEGYQLM 1822
     |..  ||| .||  |   :| ||. : :|| |:.|.
 540 LVWSSPKDVCKRKSCKTPPDPVNGMVHVITDI.QVGSRINYSCTTGHRLI 588
```

Figure 3B

```
1823 GVTKITCLESG...EWNHLIPYCKAVSCGKPAIPENG...CIEELAFTFG 1866
     | .   |:  ||   |.   | |. : ||  |    ||         | :|
 589 GHSSAECILSGNAAHWSTKPPICQRIPCGLPPTIANGDFISTNRENFHYG 638

1867 SKVTYRCNKG......YTLAGDKESSCLANSS....WSHSPPVC.EPVKC 1905
     | ||||||  |       : | |:   | .|     ||   | |  | ||
 639 SVVTYRCNPGSGGRKVFELVGEPSIYCTSNDDQVGIWSGPAPQCIIPNKC 688

1906 SSPENINNGKYILSGLTYLS...TASYSCDTGYSLQGPSIIECTASGIWD 1952
     .| |: ||  :   . |      : |  |: :.|| :.| |    |:
 689 .TPPNVENGILVSDNRSLFSLNEVVEFRCQPGFVMKGPRRVKCQALNKWE 737

1953 RAPPACHLVFCGEPPAIKDAVIT...GNNFTFRNTVTYTCKEGYTLAGLD 1999
     |.|  | |  ||  :  |  |    .||.   | |.|. || | |
 738 PELPSCSRV.CQPPPDVLHAERTQRDKDNFSPGQEVFYSCEPGYDLRGAA 786

2000 TIECLADGKWSRSDQQCLAVSCDE..PPIVDHASPETAHRLFGDIAFYYC 2047
     .. |   | ||  .  |   |||:    :..   .   |    : |
 787 SMRCTPQGDWSPAAPTCEVKSCDDFMGQLLNGRVLFPVNLQLGAKVDFVC 836

2048 SDGYSLADNSQLLCNAQGKWVPPEGQDMPRCIAHFCEKPPSVSYSILESV 2097
     :|: |  .|   | |     .| |   ||  || ||  :
 837 DEGFQLKGSSASYCVLAG.MESLWNSSVPVCEQIFCPSPPVIPNGRHTGK 885

2098 SKAKFAAGSVVSFKC......MEGFVLNTSAKIECMRGGQWN...PSPMS 2138
     | |   | .: |          | |   . | |    ||       ||
 886 PLEVFPFGKTVNYTCDPHPDRGTSFDLIGESTIRCTSDPQGNGVWSSPAP 935

2139 IQCIPVRCGEPPSI....MNGYASGSNYSFGAMVAYSCNKGFYIKGEKKS 2184
     | |       :      .|.: |  |   ||  :|   |
 936 RCGILGHCQAPDHFLFAKLKTQTNASDFPIGTSLKYECRPEYY..GRPFS 983

2185 .TCEATGQWSSPIPTCHPVSCGEPPKVENGFLEHTTGRIFESEVRYQCNP 2233
     ||    ||||  |   ||  ||  ||.   |     |:||
 984 ITCLDNLVWSSPKDVCKRKSCKTPPDPVNGMVHVITDIQVGSRINYSCTT 1033

2234 GYKSVG..SPVFVCQAN.RHWHSESPLMCVPLDCGKPPPIQNG.FM..KG 2277
     |:: :|   |    :   |  ||  .. |: |  : || ||  | ||.
1034 GHRLIGHSSAECILSGNAAHWSTKPPI.CQRIPCGLPPTIANGDFISTNR 1082

2278 ENFEVGSKVQFFCNEG......YELVGDSSWTCQKS....GKWNKKSNPK 2317
     |||  || | | ||         :||||: | |   .    | |. . |.
1083 ENFHYGSVVTYRCNPGSGGRKVFELVGEPSIYCTSNDDQVGIWSGPA.PQ 1131

2318 C.MPAKCPEPPLLENQLVL...KELTTEVGVVTFSCKEGHVLQGPSVLKC 2363
     | .| ||  || .||  :..    : |.  || | |. | |:.|| .||
1132 CIIPNKC.TPPNVENGILVSDNRSLFSLNEVVEFRCQPGFVMKGPRRVKC 1180

2364 LPSQQWNDSFPVCKIVLCTPPPLISFGVPIPSSALHF..GSTVKYSCVGG 2411
      .|   |  | | |||:         .|  | | |||  |
1181 QALNKWEPELPSCSRV.CQPPPDVLHAERTQRDKDNFSPGQEVFYSCEPG 1229

2412 FFLRGNSTTLCQPDGTWSSPLPECVPVECPQ.PEEIPNG.IIDVQGLAYL 2459
     : ||| ..  |  ||  | |  |    :: ||  ::         |
1230 YDLRGAASMRCTPQGDWSPAAPTCEVKSCDDFMGQLLNGRVLFPVNLQLG 1279
```

Figure 3C

```
2460 STALYTCKPGFELVGNTTTLC...GENGHWLGGKPTCKAIECLKPKEILN 2506
       : |  ||:| |.. . |   |    |   ||.| ||   | ||
1280 AKVDFVCDEGFQLKGSSASYCVLAGMESLWNSSVPVCEQIFCPSPPVIPN 1329

2507 GKFSYTDLH...YGQTVTYSC....NRG..FRLEGPSALTCLE....TGD 2543
     |:  .  |    :|. | |.|    .|| | | | | :  |         |
1330 GRHTGKPLEVFPFGKAVNYTCDPHPDRGTSFDLIGESTIRCTSDPQGNGV 1379

2544 WDVDAPSCNAI.HCDSPQPIENGFVE....GADYSYGAIIIYSCFPGFQV 2588
     |  || |   : || .|      ..     .|: |   : | | | :
1380 WSSPAPRCGILGHCQAPDHFLFAKLKTQTNASDFPIGTSLKYECRPEYYG 1429

2589 AGHAMQTCEESGWSSSIPTCMPIDCGLPP.......H....IDFG..... 2622
     .. ·     |||    |   | ||        |    | |
1430 RPFSITCLDNLVWSSPKDVCKRKSCKTPPDPVNGMVHVITDIQVGSRINY 1479

2623 DCTKLKDDQGYFEQEDDMM.EVPYVTPHPP..YHLGAVAKTWENTKESPA 2669
     ||       |:  |  :    :  . ||         :        :  .
1480 SCTTGHRLIGHSSAECILSGNTAHWSTKPPICQRIPCGLPPTIANGDFIS 1529

2670 THSSNFLYGTMVSYTCNPG......YELLGNPVLIC..QED..GTWNGSA 2709
     |.  || ||..|.| || |       :||.| |  :  |   :| | |.| |
1530 TNRENFHYGSVVTYRCNLGSRGRKVFELVGEPSIYCTSNDDQVGIWSGPA 1579

2710 PSCISIECDLPTAPENGFLRFTETSMGS...AVQYSCKPGHILVGSDLRL 2756
     | ||      |    ||| |     |: |      |:: |.|| :: |
1580 PQCIIPNKCTPPNVENGILVSDNRSLFSLNEVVEFRCQPGFVMKGPRRVK 1629

2757 CLENRKWSGASPRCEAISCKKPNPVMNGSIKGS...NYTYLSTLYYECDP 2803
     |   ||   | |    : |. |    ::.|    |   |:.    .:| |:|
1630 CQALNKWEPELPSCSRV.CQPPPEILHGEHTPSHQDNFSPGQEVFYSCEP 1678

2804 GYVLNGTERRTCQDDKNWDEDEPICIPVDCSS.PPVSANGQVRGD EYTF 2851
     ||| |    |    .| : ||   |         .|.|
1679 GYDLRGAASLHCTPQGDWSPEAPRCAVKSCDDFLGQLPHGRVLFPLNLQL 1728

2852 QKEIEYTCNEGFLLEGARSRVCLANGS...WSGATPDCVPVRCATPPQLA 2898
     .: :  |.||| |.|.    |.  |   |. . |  :  |   || :
1729 GAKVSFVCDEGFRLKGSSVSHCVLVGMRSLWNNSVPVCEHIFCPNPPAIL 1778

2899 NGVTEGL...DYGFMKEVTFHC..H..EG..YILHGAPKLTCQSD..GN. 2936
     ||   |    |  : ||:.: | |    |   :| |    : ||   ||
1779 NGRHTGTPSGDIPYGKEISYTCDPHPDRGMTFNLIGESTIRCTSDPHGNG 1828

2937 .WDAEIPLC....KPVNCGPPEDLAHGFP....NGFSIHGGHIQYQCFP 2977
     |. ||   :  .| ||        |   | | | | :|:| |
1829 VWSSPAPRCELSVRAGHCKTPEQFPFASPTIPINDFEFPVGTSLNYECRP 1878

2978 GYKLHGNSSRRCLSNGSWSGSSPSCLPCRCSTPVIEY.GTVN.GTDFDCG 3025
     ||     |  || | ||    .|   | |   : | |. ||     |
1879 GY.FGKMFSISCLENLVWSSVEDNCRRKSCGPPPEPFNGMVHINTDTQFG 1927

3026 KAARIQCFKGFKLLGLSEITCEADGQ...WSSGFPHCEHTSCGSLPMIPN 3072
     | .||:|:| ||    |    | |  ||  ||    ||| |
1928 STVNYSCNEGFRLIGSPSTTCLVSGNNVTWDKKAPICEIISCEPPPTISN 1977
```

Figure 3D

```
3073 A.FIS..ETSSWKENVITYSCRSG......YVIQGSSDLICTEK....GV 3109
     | |   ||     |:|| | .|      : :  |  : || |    ||
1978 GDFYSNNRTSFHNGTVVTYQCHTGPDGEQLFELVGERSIYCTSKDDQVGV 2027

3110 WSQPYPVCEPLSCGSPPSVANAVATGEAHTYES...EVKLRCLEGYTMDT 3156
     || | |   .  . | ||:       .: |    |: || |: |
2028 WSSPPPRCISTNKCTAPEVENAIRVPGNRSFFSLTEIVRFRCQPGFVM.V 2076

3157 DTDTFTCQKDGRWFPERISCSPKKCPLPENI..THILVHGDDFSVNRQVS 3204
     . |  || .||| |.  ||    | || :   | | | |.||  .:|
2077 GSHTVQCQTNGRWGPKLPHCSRVCQPPPEILHGEHTLSHQDNFSPGQEVF 2126

3205 VSCAEGYTFEGVNISVCQLDGTWEPPFSDESCSPVSCGK..PESPEHGFV 3252
     ||    |    |   | |  |    |.  ||       :  |    .
2127 YSCEPSYDLRGAASLHCTPQGDWSP..EAPRCTVKSCDDFLGQLPHGRVL 2174

3253 VGSKYTFESTIIYQCEPGYELEGNRERVC...QENRQWSGGVAICKETRC 3299
     .       . : |: |.|     |     |. |  |:|.:  |
2175 LPLNLQLGAKVSFVCDEGFRLKGRSASHCVLAGMKALWNSSVPVCEQIFC 2224

3300 ETPLEFLNGK...ADIENRTTGPNVVYSC....NRG..YSLEGPSEAHCT 3340
     |  |||:      | : |.|   .|| :.| | |    ||
2225 PNPPAILNGRHTGTPFGDIPYGKEISYACDTHPDRGMTFNLIGESSIRCT 2274

3341 E....NGTWSHPVPLCK...PNPCPVPFVIPENALL.SEKEFYV.DQNVS 3381
     ||  || | | | |.   |  || | |       :     |.    :|
2275 SDRQGNGVWSSPAPRCELSVPAACPDPPKIQNGHYIGGHVSLYLPGMTIS 2324

3382 IKCREGFLLQGHGIITCNPDETWTQTSAKCEKISCGPPAHVENAIARGVH 3431
     |  |:|| | | | |    |.|   |..:.|  | . | |.:  .
2325 YICDPGYLLVGKGFIFCTDQGIWSQLDHYCKEVNCSFPLFM.NGISKELE 2373

3432 ....YQYGDMITYSCYSGYMLEGFLRSVCLENGTWTSPPICRAVCRFPCQ 3477
     | ||| :|   | || |||   | |  .   |  ||:   | |
2374 MKKVYHYGDYVTLKCEDGYTLEGSPWSQCQADDRW.DPPL...AKCTSRAH 2420

3478 NGGICQRPNACSCPEGWMGRLCEEPICILPCLNGGRC VAPYQCDCP.PG 3525
     . |         |   ..  :       ||        |           | :
2421 DALIV...GTLSGTIFFILLIIFLSWIILKHRKGNNAHENPKEVAIHLHS 2467

3526 WTGSRCHTAVCQSPCLNGGKCVRPNRCHCLSSWTGHNCSRKRRTGF* 3572
     ||  |  |. |  | |
2468 QGGSSVHPRTLQTNEENSR..VLP................... 2489
```

C3B/C4B COMPLEMENT RECEPTOR-LIKE MOLECULES AND USES THEREOF

RELATED APPLICATION

The present application claims priority benefit of U.S. provisional application No. 60/222,438 filed Aug. 1, 2000 which is incorporated herein by reference in its entirety.

FIELD OF THE INVENTION

The present invention relates to novel C3b/C4b Complement Receptor-like polypeptides and nucleic acid molecules encoding the same. The invention also relates to vectors, host cells, pharmaceutical compositions, selective binding agents and methods for producing C3b/C4b Complement Receptor-like polypeptides. Also provided for are methods for the diagnosis, treatment, amelioration, and/or prevention of diseases associated with C3b/C4b Complement Receptor-like polypeptides.

BACKGROUND OF THE INVENTION

Technical advances in the identification, cloning, expression and manipulation of nucleic acid molecules and the deciphering of the human genome have greatly accelerated the discovery of novel therapeutics. Rapid nucleic acid sequencing techniques can now generate sequence information at unprecedented rates and, coupled with computational analyses, allow the assembly of overlapping sequences into partial and entire genomes and the identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides may confer advantageous properties on a product for use as a therapeutic.

In spite of the significant technical advances in genome research over the past decade, the potential for the development of novel therapeutics based on the human genome is still largely unrealized. Many genes encoding potentially beneficial polypeptide therapeutics, or those encoding polypeptides, which may act as "targets" for therapeutic molecules, have still not been identified.

Accordingly, it is an object of the invention to identify novel polypeptides and nucleic acid molecules encoding the same, which have diagnostic or therapeutic benefit.

SUMMARY OF THE INVENTION

The present invention relates to novel C3b/C4b Complement Receptor-like nucleic acid molecules and encoded polypeptides.

The invention provides for an isolated nucleic acid molecule comprising a nucleotide sequence selected from the group consisting of:
 (a) the nucleotide sequence as set forth in SEQ ID NO:1 or SEQ ID NO:3;
 (b) a nucleotide sequence encoding the polypeptide as set forth in SEQ ID NO:2 or SEQ ID NO:4;
 (c) a nucleotide sequence which hybridizes under moderately or highly stringent conditions to the complement of (a) or (b), wherein the encoded polypeptide has an activity of the polypeptide as set forth in SEQ ID NO:2 or SEQ ID NO:4; and
 (d) a nucleotide sequence complementary to any of (a)–(c).

The invention also provides for an isolated nucleic acid molecule comprising a nucleotide sequence selected from the group consisting of:
 (a) a nucleotide sequence encoding a polypeptide that is at least about 70, 75, 80, 85, 90, 95, 96, 97, 98, or 99 percent identical to the polypeptide as set forth in SEQ ID NO:2 or SEQ ID NO:4, wherein the polypeptide has an activity of the polypeptide as set forth in SEQ ID NO:2 or SEQ ID NO:4;
 (b) a nucleotide sequence encoding an allelic variant or splice variant of the nucleotide sequence as set forth in SEQ ID NO:1 or SEQ ID NO:3, wherein the encoded polypeptide has an activity of the polypeptide as set forth in SEQ ID NO:2 or SEQ ID NO:4;
 (c) a nucleotide sequence of SEQ ID NO:1 or SEQ ID NO:3, (a), or (b) encoding a polypeptide fragment of at least about 25 amino acid residues, wherein the polypeptide has an activity of the polypeptide as set forth in SEQ ID NO:2 or SEQ ID NO:4;
 (d) a nucleotide sequence of SEQ ID NO:1 or SEQ ID NO:3, or (a)–(c) comprising a fragment of at least about 16 nucleotides;
 (e) a nucleotide sequence which hybridizes under moderately or highly stringent conditions to the complement of any of (a)–(d), wherein the polypeptide has an activity of the polypeptide as set forth in SEQ ID NO:2 or SEQ ID NO:4; and
 (f) a nucleotide sequence complementary to any of (a)–(e).

The invention further provides for an isolated nucleic acid molecule comprising a nucleotide sequence selected from the group consisting of:
 (a) a nucleotide sequence encoding a polypeptide as set forth in SEQ ID NO:2 or SEQ ID NO:4 with at least one conservative amino acid substitution, wherein the polypeptide has an activity of the polypeptide as set forth in SEQ ID NO:2 or SEQ ID NO:4;
 (b) a nucleotide sequence encoding a polypeptide as set forth in SEQ ID NO:2 or SEQ ID NO:4 with at least one amino acid insertion, wherein the polypeptide has an activity of the polypeptide as set forth in SEQ ID NO:2 or SEQ ID NO:4;
 (c) a nucleotide sequence encoding a polypeptide as set forth in SEQ ID NO:2 or SEQ ID NO:4 with at least one amino acid deletion, wherein the polypeptide has an activity of the polypeptide as set forth in SEQ ID NO:2 or SEQ ID NO:4;
 (d) a nucleotide sequence encoding a polypeptide as set forth in SEQ ID NO:2 or SEQ ID NO:4 which has a C- and/or N-terminal truncation, wherein the polypeptide has an activity of the polypeptide as set forth in SEQ ID NO:2 or SEQ ID NO:4;
 (e) a nucleotide sequence encoding a polypeptide as set forth in SEQ ID NO:2 or SEQ ID NO:4 with at least one modification selected from the group consisting of amino acid substitutions, amino acid insertions, amino acid deletions, C-terminal truncation, and N-terminal truncation, wherein the polypeptide has an activity of the polypeptide as set forth in SEQ ID NO:2 or SEQ ID NO:4;
 (f) a nucleotide sequence of (a)–(e) comprising a fragment of at least about 16 nucleotides;
 (g) a nucleotide sequence which hybridizes under moderately or highly stringent conditions to the complement of any of (a)–(f), wherein the polypeptide has an activity of the polypeptide as set forth in SEQ ID NO:2 or SEQ ID NO:4; and (h) a nucleotide sequence complementary to any of (a)–(e).

The invention also provides for an isolated polypeptide comprising the amino acid sequence selected from the group consisting of:

(a) an amino acid sequence of the mature C3b/C4b Complement Receptor-like polypeptide wherein the polypeptide comprises the amino acid sequence as set forth in SEQ ID NO:2 or SEQ ID NO:4, and optionally further comprises an amino-terminal methionine;

(b) an amino acid sequence for an ortholog of SEQ ID NO:2 or SEQ ID NO:4, wherein the encoded polypeptide has an activity of the polypeptide as set forth in SEQ ID NO:2 or SEQ ID NO:4;

(c) an amino acid sequence that is at least about 70, 80, 85, 90, 95, 96, 97, 98, or 99 percent identical to the amino acid sequence of SEQ ID NO:2 or SEQ ID NO:4, wherein the polypeptide has an activity of the polypeptide as set forth in SEQ ID NO:2 or SEQ ID NO:4;

(d) a fragment of the amino acid sequence set forth in SEQ ID NO:2 or SEQ ID NO:4 comprising at least about 25 amino acid residues, wherein the polypeptide has an activity of the polypeptide as set forth in SEQ ID NO:2 or SEQ ID NO:4;

(e) an amino acid sequence for an allelic variant or splice variant of either the amino acid sequence as set forth in SEQ ID NO:2 or SEQ ID NO:4, or at least one of (a)–(c) wherein the polypeptide has an activity of the polypeptide as set forth in SEQ ID NO:2 or SEQ ID NO:4.

The invention further provides for an isolated polypeptide comprising the amino acid sequence selected from the group consisting of:

(a) the amino acid sequence as set forth in SEQ ID NO:2 or SEQ ID NO:4 with at least one conservative amino acid substitution, wherein the polypeptide has an activity of the polypeptide as set forth in SEQ ID NO:2 or SEQ ID NO:4;

(b) the amino acid sequence as set forth in SEQ ID NO:2 or SEQ ID NO:4 with at least one amino acid insertion, wherein the polypeptide has an activity of the polypeptide as set forth in SEQ ID NO:2 or SEQ ID NO:4;

(c) the amino acid sequence as set forth in SEQ ID NO:2 or SEQ ID NO:4 with at least one amino acid deletion, wherein the polypeptide has an activity of the polypeptide as set forth in SEQ ID NO:2 or SEQ ID NO:4;

(d) the amino acid sequence as set forth in SEQ ID NO:2 or SEQ ID NO:4 which has a C- and/or N-terminal truncation, wherein the polypeptide has an activity of the polypeptide as set forth in SEQ ID NO:2 or SEQ ID NO:4; and (e) the amino acid sequence as set forth in SEQ ID NO:2 or SEQ ID NO:4, with at least one modification selected from the group consisting of amino acid substitutions, amino acid insertions, amino acid deletions, C-terminal truncation, and N-terminal truncation, wherein the polypeptide has an activity of the polypeptide as set forth in SEQ ID NO:2 or SEQ ID NO:4.

Also provided are fusion polypeptides comprising the amino acid sequences of (a)–(e) above.

The present invention also provides for an expression vector comprising the isolated nucleic acid molecules as set forth herein, recombinant host cells comprising recombinant nucleic acid molecules as set forth herein, and a method of producing an C3b/C4b Complement Receptor-like polypeptide comprising culturing the host cells and optionally isolating the polypeptide so produced.

A transgenic non-human animal comprising a nucleic acid molecule encoding an C3b/C4b Complement Receptor-like polypeptide is also encompassed by the invention. The C3b/C4b Complement Receptor-like nucleic acid molecules are introduced into the animal in a manner that allows expression and increased levels of the C3b/C4b Complement Receptor-like polypeptide, which may include increased circulating levels. The transgenic non-human animal is preferably a mammal.

Also provided are derivatives of the C3b/C4b Complement Receptor-like polypeptides of the present invention.

Additionally provided are selective binding agents such as antibodies and peptides capable of specifically binding the C3b/C4b Complement Receptor-like polypeptides of the invention. Such antibodies and peptides may be agonistic or antagonistic.

Pharmaceutical compositions comprising the nucleotides, polypeptides, or selective binding agents of the present invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents.

The C3b/C4b Complement Receptor-like polypeptides and nucleic acid molecules of the present invention may be used to treat, prevent, ameliorate, and/or detect diseases and disorders, including those recited herein.

The present invention also provides a method of assaying test molecules to identify a test molecule which binds to an C3b/C4b Complement Receptor-like polypeptide. The method comprises contacting an C3b/C4b Complement Receptor-like polypeptide with a test molecule and determining the extent of binding of the test molecule to the polypeptide. The method further comprises determining whether such test molecules are agonists or antagonists of an C3b/C4b Complement Receptor-like polypeptide. The present invention further provides a method of testing the impact of molecules on the expression of C3b/C4b Complement Receptor-like polypeptide or on the activity of C3b/C4b Complement Receptor-like polypeptide.

Methods of regulating expression and modulating (i.e., increasing or decreasing) levels of an C3b/C4b Complement Receptor-like polypeptide are also encompassed by the invention. One method comprises administering to an animal a nucleic acid molecule encoding an C3b/C4b Complement Receptor-like polypeptide. In another method, a nucleic acid molecule comprising elements that regulate or modulate the expression of an C3b/C4b Complement Receptor-like polypeptide may be administered. Examples of these methods include gene therapy, cell therapy, and anti-sense therapy as further described herein.

The C3b/C4b Complement Receptor-like polypeptide can be used for identifying ligands thereof. Various forms of "expression cloning" have been used for cloning ligands for receptors. See e.g., Davis et al., *Cell,* 87:1161–1169 (1996). These and other C3b/C4b Complement Receptor-like ligand cloning experiments are described in greater detail herein. Isolation of the C3b/C4b Complement Receptor-like ligand (s) allows for the identification or development of novel agonists and/or antagonists of the C3b/C4b Complement Receptor-like signaling pathway. Such agonists and antagonists include C3b/C4b Complement Receptor-like ligand(s), anti-C3b/C4b Complement Receptor-like ligand antibodies and derivatives thereof, small molecules, or antisense oligonucleotides, any of which can be used for potentially treating one or more diseases or disorders, including those recited herein.

BRIEF DESCRIPTION OF THE FIGURES

FIG. 1A–1K depicts a nucleic acid sequence (SEQ ID NO:1) encoding human C3b/C4b Complement Receptor-like Protein. Also depicted is the amino acid sequence (SEQ ID NO:2) of human C3B/C4b Complement Receptor-like Protein.

FIG. 2A–2K depicts a nucleic acid sequence (SEQ ID NO:3) encoding mouse C3b/C4b Complement Receptor-like Protein. Also depicted is the amino acid sequence of mouse C3b/C4b Complement Receptor-like protein (SEQ ID NO:4).

FIG. 3A–3D depicts an amino acid comparison of human C3b/C4b Complement Receptor (SEQ ID NO:2) and human AGP-03144 (SEQ ID NO:5).

DETAILED DESCRIPTION OF THE INVENTION

The section headings used herein are for organizational purposes only and are not to be construed as limiting the subject matter described. All references cited in this application are expressly incorporated by reference herein.

Definitions

The term "C3b/C4b Complement Receptor-like" is abbreviated herein as "C3b/C4b CR-like" and is also referred to as "AGP-03144". The terms "C3b/C4b CR-like gene" or "C3b/C4b CR-like nucleic acid molecule" or "polynucleotide" refers to a nucleic acid molecule comprising or consisting of a nucleotide sequence as set forth in SEQ ID NO:1 or SEQ ID NO:3, a nucleotide sequence encoding the polypeptide as set forth in SEQ ID NO:2 or SEQ ID NO:4, and nucleic acid molecules as defined herein.

The term "C3b/C4b CR-like polypeptide" refers to a polypeptide comprising the amino acid sequence of SEQ ID NO:2 or SEQ ID NO:4, and related polypeptides. Related polypeptides include: C3b/C4b CR-like polypeptide allelic variants, C3b/C4b CR-like polypeptide orthologs, C3b/C4b CR-like polypeptide splice variants, C3b/C4b CR-like polypeptide variants and C3b/C4b CR-like polypeptide derivatives. C3b/C4b CR-like polypeptides may be mature polypeptides, as defined herein, and may or may not have an amino terminal methionine residue, depending on the method by which they are prepared.

The term "C3b/C4b CR-like polypeptide allelic variant" refers to one of several possible naturally occurring alternate forms of a gene occupying a given locus on a chromosome of an organism or a population of organisms.

The term "C3b/C4b CR-like polypeptide derivatives" refers to the polypeptide as set forth in SEQ ID NO:2 or SEQ ID NO:4, C3b/C4b CR-like polypeptide allelic variants, C3b/C4b CR-like polypeptide orthologs, C3b/C4b CR-like polypeptide splice variants, or C3b/C4b CR-like polypeptide variants, as defined herein, that have been chemically modified.

The term "C3b/C4b CR-like polypeptide fragment" refers to a polypeptide that comprises a truncation at the amino terminus (with or without a leader sequence) and/or a truncation at the carboxy terminus of the polypeptide as set forth in SEQ ID NO:2 or SEQ ID NO:4, C3b/C4b CR-like polypeptide allelic variants, C3b/C4b CR-like polypeptide orthologs, C3b/C4b CR-like polypeptide splice variants and/or an C3b/C4b CR-like polypeptide variant having one or more amino acid additions or substitutions or internal deletions (wherein the resulting polypeptide is at least 6 amino acids or more in length) as compared to the C3b/C4b CR-like polypeptide amino acid sequence set forth in SEQ ID NO:2 or SEQ ID NO:4. C3b/C4b CR-like polypeptide fragments may result from alternative RNA splicing or from in vivo protease activity. For transmembrane or membrane-bound forms of an C3b/C4b CR-like polypeptide, preferred fragments include soluble forms such as those lacking a transmembrane or membrane-binding domain. In preferred embodiments, truncations comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such C3b/C4b CR-like polypeptide fragments may optionally comprise an amino terminal methionine residue. It will be appreciated that such fragments can be used, for example, to generate antibodies to C3b/C4b CR-like polypeptides.

The term "C3b/C4b CR-like fusion polypeptide" refers to a fusion of one or more amino acids (such as a heterologous peptide or polypeptide) at the amino or carboxy terminus of the polypeptide as set forth in SEQ ID NO:2 or SEQ ID NO:4, C3b/C4b CR-like polypeptide allelic variants, C3b/C4b CR-like polypeptide orthologs, C3b/C4b CR-like polypeptide splice variants, or C3b/C4b CR-like polypeptide variants having one or more amino acid deletions, substitutions or internal additions as compared to the C3b/C4b CR-like polypeptide amino acid sequence set forth in SEQ ID NO:2 or SEQ ID NO:4.

The term "C3b/C4b CR-like polypeptide ortholog" refers to a polypeptide from another species that corresponds to C3b/C4b CR-like polypeptide amino acid sequence as set forth in SEQ ID NO:2 or SEQ ID NO:4. For example, mouse and human C3b/C4b CR-like polypeptides are considered orthologs of each other.

The term "C3b/C4b CR-like polypeptide splice variant" refers to a nucleic acid molecule, usually RNA, which is generated by alternative processing of intron sequences in an RNA transcript of C3b/C4b CR-like polypeptide amino acid sequence as set forth in SEQ ID NO:2 or SEQ ID NO:4.

The term "C3b/C4b CR-like polypeptide variants" refers to C3b/C4b CR-like polypeptides comprising amino acid sequences having one or more amino acid sequence substitutions, deletions (such as internal deletions and/or C3b/C4b CR-like polypeptide fragments), and/or additions (such as internal additions and/or C3b/C4b CR-like fusion polypeptides) as compared to the C3b/C4b CR-like polypeptide amino acid sequence set forth in SEQ ID NO:2 or SEQ ID NO:4 (with or without a leader sequence). Variants may be naturally occurring (e.g., C3b/C4b CR-like polypeptide allelic variants, C3b/C4b CR-like polypeptide orthologs and C3b/C4b CR-like polypeptide splice variants) or artificially constructed. Such C3b/C4b CR-like polypeptide variants may be prepared from the corresponding nucleic acid molecules having a DNA sequence that varies accordingly from the DNA sequence as set forth in SEQ ID NO:1 or SEQ ID NO:3. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "biologically active C3b/C4b CR-like polypeptides" refers to C3b/C4b CR-like polypeptides having at least one activity characteristic of the polypeptide comprising the amino acid sequence of SEQ ID NO:2 or SEQ ID NO:4.

The terms "effective amount" and "therapeutically effective amount" each refer to the amount of a C3b/C4b CR-like polypeptide or C3b/C4b CR-like nucleic acid molecule used to support an observable level of one or more biological activities of the C3b/C4b CR-like polypeptides as set forth herein.

The term "expression vector" refers to a vector which is suitable for use in a host cell and contains nucleic acid sequences which direct and/or control the expression of heterologous nucleic acid sequences. Expression includes, but is not limited to, processes such as transcription, translation, and RNA splicing, if introns are present.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "identity" as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity", refers to a measure of similarity which includes both identical matches and conservative substitution matches. If two polypeptide sequences have, for example, 10/20 identical amino acids, and the remainder are all non-conservative substitutions, then the percent identity and similarity would both be 50%. If in the same example, there are 5 more positions where there are conservative substitutions, then the percent identity remains 50%, but the percent similarity would be 75% (15/20). Therefore, in cases where there are conservative substitutions, the degree of similarity between two polypeptides will be higher than the percent identity between those two polypeptides.

The term "isolated nucleic acid molecule" refers to a nucleic acid molecule of the invention that (1) has been separated from at least about 50 percent of proteins, lipids, carbohydrates or other materials with which it is naturally found when total DNA is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "isolated polypeptide" refers to a polypeptide of the present invention that (1) has been separated from at least about 50 percent of polynucleotides, lipids, carbohydrates or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "mature C3b/C4b CR-like polypeptide" refers to an C3b/C4b CR-like polypeptide lacking a leader sequence. A mature C3b/C4b CR-like polypeptide may also include other modifications such as proteolytic processing of the amino terminus (with or without a leader sequence) and/or the carboxy terminus, cleavage of a smaller polypeptide from a larger precursor, N-linked and/or O-linked glycosylation, and the like.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "pharmaceutically acceptable carrier" or "physiologically acceptable carrier" as used herein refers to one or more formulation materials suitable for accomplishing or enhancing the delivery of the C3b/C4b CR-like polypeptide, C3b/C4b CR-like nucleic acid molecule or C3b/C4b CR-like selective binding agent as a pharmaceutical composition.

The term "selective binding agent" refers to a molecule or molecules having specificity for an C3B/C4B CR-like polypeptide. As used herein, the terms, "specific" and "specificity" refer to the ability of the selective binding agents to bind to human C3b/C4b CR-like polypeptides and not to bind to human non-C3b/C4b CR-like polypeptides. It will be appreciated, however, that the selective binding agents may also bind orthologs of the polypeptide as set forth in SEQ ID NO:2 or SEQ ID NO:4, that is, interspecies versions thereof, such as mouse and mouse polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, for example, Graham et al., *Virology*, 52:456 (1973); Sambrook et al., *Molecular Cloning, a laboratory Manual*, Cold Spring Harbor Laboratories (New York, 1989); Davis et al., *Basic Methods in Molecular Biology*, Elsevier, 1986; and Chu et al., *Gene*, 13:197 (1981). Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

The term "vector" is used to refer to any molecule (e.g., nucleic acid, plasmid, or virus) used to transfer coding information to a host cell.

Relatedness of Nucleic Acid Molecules and/or Polypeptides

It is understood that related nucleic acid molecules include allelic or splice variants of the nucleic acid molecule of SEQ ID NO:1 or SEQ ID NO:3, and include sequences which are complementary to any of the above nucleotide sequences. Related nucleic acid molecules also include a nucleotide sequence encoding a polypeptide comprising or consisting essentially of a substitution, modification, addition and/or a deletion of one or more amino acid residues compared to the polypeptide in SEQ ID NO:2 or SEQ ID NO:4.

Fragments include molecules which encode a polypeptide of at least about 25 amino acid residues, or about 50, or about 75, or about 100, or greater than about 100 amino acid residues of the polypeptide of SEQ ID NO:2 or SEQ ID NO:4.

In addition, related C3b/C4b CR-like nucleic acid molecules include those molecules which comprise nucleotide sequences which hybridize under moderately or highly stringent conditions as defined herein with the fully complementary sequence of the nucleic acid molecule of SEQ ID NO:1 or SEQ ID NO:3, or of a molecule encoding a polypeptide, which polypeptide comprises the amino acid sequence as shown in SEQ ID NO:2 or SEQ ID NO:4, or of a nucleic acid fragment as defined herein, or of a nucleic acid fragment encoding a polypeptide as defined herein. Hybridization probes may be prepared using the C3b/C4b CR-like sequences provided herein to screen cDNA, genomic or synthetic DNA libraries for related sequences. Regions of the DNA and/or amino acid sequence of C3b/C4b CR-like polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015M sodium chloride, 0.0015M sodium citrate at 65–68° C. or 0.015M sodium chloride, 0.0015M sodium citrate, and 50% formamide at 42° C. See Sambrook, Fritsch & Maniatis, Molecular Cloning: A Laboratory Manual, $2^{nd}$ Ed., Cold Spring Harbor Laboratory, (Cold Spring Harbor, N.Y. 1989); Anderson et al., Nucleic Acid Hybridisation: a practical approach, Ch. 4, IRL Press Limited (Oxford, England).

More stringent conditions (such as higher temperature, lower ionic strength, higher formamide, or other denaturing agent) may also be used, however, the rate of hybridization will be affected. Other agents may be included in the hybridization and washing buffers for the purpose of reducing non-specific and/or background hybridization. Examples are 0.1% bovine serum albumin, 0.1% polyvinylpyrrolidone, 0.1% sodium pyrophosphate, 0.1% sodium dodecylsulfate ($NaDodSO_4$ or SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8–7.4, however, at typical ionic strength conditions, the rate of hybridization is nearly independent of pH. See Anderson et al., Nucleic Acid Hybridisation: a Practical Approach, Ch. 4, IRL Press Limited (Oxford, England).

Factors affecting the stability of a DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(° C.)=81.5+16.6(\log[Na+])+0.41(\%G+C)-600/N-0.72(\%\text{formamide})$$

where N is the length of the duplex formed, [Na+] is the molar concentration of the sodium ion in the hybridization or washing solution, %G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015M sodium chloride, 0.0015M sodium citrate at 50–65° C. or 0.015M sodium chloride, 0.0015M sodium citrate, and 20% formamide at 37–50° C. By way of example, a "moderately stringent" condition of 50° C. in 0.015 M sodium ion will allow about a 21% mismatch.

It will be appreciated by those skilled in the art that there is no absolute distinction between "highly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20nt is given by:

$$Tm=2° \text{ C. per } A-T \text{ base pair}+4° \text{ C. per } G-C \text{ base pair}$$

*The sodium ion concentration in 6× salt sodium citrate (SSC) is 1M. See Suggs et al., Developmental Biology Using Purified Genes, p. 683, Brown and Fox (eds.) (1981).

High stringency washing conditions for oligonucleotides are usually at a temperature of 0–5° C. below the Tm of the oligonucleotide in 6×SSC, 0.1% SDS.

In another embodiment, related nucleic acid molecules comprise or consist of a nucleotide sequence that is about 70 percent identical to the nucleotide sequence as shown in SEQ ID NO:1 or SEQ ID NO:3, or comprise or consist essentially of a nucleotide sequence encoding a polypeptide that is about 70 percent identical to the polypeptide as set forth in SEQ ID NO:2 or SEQ ID NO:4. In preferred embodiments, the nucleotide sequences are about 75 percent, or about 80 percent, or about 85 percent, or about 90 percent, or about 95, 96, 97, 98, or 99 percent identical to the nucleotide sequence as shown in SEQ ID NO:1 or SEQ ID NO:3, or the nucleotide sequences encode a polypeptide that is about 75 percent, or about 80 percent, or about 85 percent, or about 90 percent, or about 95, 96, 97, 98, or 99 percent identical to the polypeptide sequence as set forth in SEQ ID NO:2 or SEQ ID NO:4.

Differences in the nucleic acid sequence may result in conservative and/or non-conservative modifications of the amino acid sequence relative to the amino acid sequence of SEQ ID NO:2 or SEQ ID NO:4.

Conservative modifications to the amino acid sequence of SEQ ID NO:2 or SEQ ID NO:4 (and the corresponding modifications to the encoding nucleotides) will produce C3b/C4b CR-like polypeptides having functional and chemical characteristics similar to those of naturally occurring C3b/C4b CR-like polypeptide. In contrast, substantial modifications in the functional and/or chemical characteristics of C3b/C4b CR-like polypeptides may be accomplished by selecting substitutions in the amino acid sequence of SEQ ID NO:2 or SEQ ID NO:4 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties.

Naturally occurring residues may be divided into classes based on common side chain properties:

1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human C3b/C4b CR-like polypeptide that are homologous with non-human C3b/C4b CR-like polypeptide orthologs, or into the non-homologous regions of the molecule.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.,* 157:105–131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the C3b/C4b CR-like polypeptide, or to increase or decrease the affinity of the C3b/C4b CR-like polypeptides described herein.

Exemplary amino acid substitutions are set forth in Table I.

TABLE I

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diaminobutyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in SEQ ID NO:2 or SEQ ID NO:4 using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of an C3b/C4b CR-like polypeptide to such similar polypeptides. With such a comparison, one can identify residues and portions of the molecules that are conserved among similar polypeptides. It will be appreciated that changes in areas of an C3b/C4b CR-like polypeptide that are not conserved relative to such similar polypeptides would be less likely to adversely affect the biological activity and/or structure of the C3b/C4b CR-like polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in an C3b/C4b CR-like polypeptide that correspond to amino acid residues that are important for activity or structure in similar polypeptides. One skilled in the art may opt for chemically similar amino acid substitutions for such predicted important amino acid residues of C3b/C4b CR-like polypeptides.

One skilled in the art can also analyze the three-dimensional structure and amino acid sequence in relation to that structure in similar polypeptides. In view of that information, one skilled in the art may predict the alignment of amino acid residues of an C3b/C4b CR-like polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.*, 7(4):422–427 (1996), Chou et al., *Biochemistry*, 13(2):222–245 (1974); Chou et al., *Biochemistry*, 113(2):211–222 (1974); Chou et al., *Adv. Enzymol. Relat. Areas Mol. Biol.*, 47:45–148 (1978); Chou et al., *Ann. Rev. Biochem.*, 47:251–276 and Chou et al., *Biophys. J.*, 26:367–384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., *Nucl. Acid. Res.*, 27(1):244–247 (1999). It has been suggested (Brenner et al., *Curr. Op. Struct. Biol.*, 7(3):369–376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3):377–87 (1997); Sippl et al., Structure, 4(1):15–9 (1996)), "profile analysis" (Bowie et al., Science, 253:164–170 (1991); Gribskov et al., Meth. Enzym., 183:146–159 (1990); Gribskov et al., Proc. Nat. Acad. Sci., 84(13):4355–4358 (1987)), and "evolutionary linkage" (See Home, supra, and Brenner, supra)

Preferred C3b/C4b CR-like polypeptide variants include glycosylation variants wherein the number and/or type of glycosylation sites has been altered compared to the amino acid sequence set forth in SEQ ID NO:2 or SEQ ID NO:4. In one embodiment, C3b/C4b CR-like polypeptide variants comprise a greater or a lesser number of N-linked glycosylation sites than the amino acid sequence set forth in SEQ ID NO:2 or SEQ ID NO:4. An N-linked glycosylation site is characterized by the sequence: Asn-X-Ser or Asn-X-Thr, wherein the amino acid residue designated as X may be any amino acid residue except proline. The substitution(s) of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred C3b/C4b CR-like variants include cysteine variants, wherein one or more cysteine residues are deleted from or substituted for another amino acid (e.g., serine) as compared to the amino acid sequence set forth in SEQ ID NO:2 or SEQ ID NO:4. Cysteine variants are useful when C3b/C4b CR-like polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In addition, the polypeptide comprising the amino acid sequence of SEQ ID NO:2 or SEQ ID NO:4 or a C3b/C4b CR-like polypeptide variant may be fused to a homologous polypeptide to form a homodimer or to a heterologous polypeptide to form a heterodimer. Heterologous peptides and polypeptides include, but are not limited to: an epitope to allow for the detection and/or isolation of an C3b/C4b CR-like fusion polypeptide; a transmembrane receptor protein or a portion thereof, such as an extracellular domain, or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in SEQ ID NO:2 or SEQ ID NO:4 or an C3b/C4b CR-like polypeptide variant.

Fusions can be made either at the amino terminus or at the carboxy terminus of the polypeptide comprising the amino acid sequence set forth in SEQ ID NO:2 or SEQ ID NO:4 or an C3b/C4b CR-like polypeptide variant. Fusions may be direct with no linker or adapter molecule or indirect using a linker or adapter molecule. A linker or adapter molecule may be one or more amino acid residues, typically up to about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of SEQ ID NO:2 or SEQ ID NO:4 or an C3b/C4b CR-like polypeptide variant is fused to one or more domains of an Fc region of human IgG. Antibodies comprise two functionally independent parts, a variable domain known as "Fab", which binds antigen, and a constant domain known as "Fc", which is involved in effector functions such as complement activation and attack by phagocytic cells. An Fc has a long serum half-life, whereas an Fab is short-lived. Capon et al., Nature, 337:525–31 (1989). When constructed together with a therapeutic protein, an Fc domain can provide longer half-life or incorporate such functions as Fc receptor binding, protein A binding, complement fixation and perhaps even placental transfer. Id. Table II summarizes the use of certain Fc fusions known in the art.

TABLE II

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al. (1995), J. Immunol., 154: 5590–5600 |
| IgG1 | TNF receptor | septic shock | Fisher et al. (1996), N. Engl. J. Med., 334: 1697–1702; Van Zee et al., (1996), J. Immunol., 156: 2221–2230 |
| IgG, IgA, IgM, or IgE (excluding the first domain) | TNF receptor | inflammation, autoimmune disorders | U.S. Pat. No. 5,808,029, issued Sep. 15, 1998 |
| IgG1 | CD4 receptor | AIDS | Capon et al. (1989), Nature 337: 525–531 |
| IgG1, IgG3 | N-terminus of IL-2 | anti-cancer, antiviral | Harvill et al. (1995), Immunotech., 1: 95–105 |
| IgG1 | C-terminus of OPG | osteoarthritis; bone density | WO 97/23614, published Jul. 3, 1997 |
| IgG1 | N-terminus of leptin | anti-obesity | PCT/US 97/23183, filed Dec. 11, 1997 |
| Human Ig Cγ1 | CTLA-4 | autoimmune disorders | Linsley (1991), J. Exp. Med., 174:561–569 |

In one example, all or a portion of the human IgG hinge, CH2 and CH3 regions may be fused at either the N-terminus or C-terminus of the C3b/C4b CR-like polypeptides using methods known to the skilled artisan. The resulting C3b/C4b CR-like fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, reduce aggregation, etc.

Identity and similarity of related nucleic acid molecules and polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., *SIAM J. Applied Math.*, 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., *Nucl. Acid. Res.*, 12:387 (1984); Genetics Computer Group, University of Wisconsin, Madison, Wis.), BLASTP, BLASTN, and FASTA (Altschul et al., *J. Mol. Biol.*, 215:403–410 (1990)). The BLASTX program is publicly available from the National Center for Biotechnology Information (NCBI) and other sources (*BLAST Manual,* Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in a preferred embodiment, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3x the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., *Proc. Natl. Acad. Sci* USA, 89:10915–10919 (1992) for the BLOSUM 62 comparison matrix) is also used by the algorithm.

Preferred parameters for a polypeptide sequence comparison include the following:

Algorithm: Needleman et al., *J. Mol. Biol.*, 48:443–453 (1970);

Comparison matrix: BLOSUM 62 from Henikoff et al., *Proc. Natl. Acad. Sci.* USA, 89:10915–10919 (1992);

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following:

Algorithm: Needleman et al., *J. Mol Biol.*, 48:443–453 (1970);

Comparison matrix: matches=+10, mismatch=0

Gap Penalty: 50

Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Synthesis

It will be appreciated by those skilled in the art the nucleic acid and polypeptide molecules described herein may be produced by recombinant and other means.

Nucleic Acid Molecules

The nucleic acid molecules encode a polypeptide comprising the amino acid sequence of an C3b/C4b CR-like polypeptide can readily be obtained in a variety of ways including, without limitation, chemical synthesis, cDNA or genomic library screening, expression library screening and/or PCR amplification of cDNA.

Recombinant DNA methods used herein are generally those set forth in Sambrook et al., *Molecular Cloning: A Laboratory Manual,* Cold Spring Harbor Laboratory Press, Cold Spring Harbor, N.Y. (1989), and/or Ausubel et al., eds., *Current Protocols in Molecular Biology,* Green Publishers Inc. and Wiley and Sons, NY (1994). The present invention provides for nucleic acid molecules as described herein and methods for obtaining the molecules.

Where a gene encoding the amino acid sequence of an C3b/C4b CR-like polypeptide has been identified from one species, all or a portion of that gene may be used as a probe to identify orthologs or related genes from the same species. The probes or primers may be used to screen cDNA libraries from various tissue sources believed to express the C3b/C4b CR-like polypeptide. In addition, part or all of a nucleic acid molecule having the sequence as set forth in SEQ ID NO:1 or SEQ ID NO:3 may be used to screen a genomic library to identify and isolate a gene encoding the amino acid sequence of an C3b/C4b CR-like polypeptide. Typically, conditions of moderate or high stringency will be employed for screening to minimize the number of false positives obtained from the screen.

Nucleic acid molecules encoding the amino acid sequence of C3b/C4b CR-like polypeptides may also be identified by expression cloning which employs the detection of positive clones based upon a property of the expressed protein. Typically, nucleic acid libraries are screened by the binding of an antibody or other binding partner (e.g., receptor or ligand) to cloned proteins which are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence which encodes the amino acid sequence of an C3b/C4b CR-like polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of an C3b/C4b CR-like polypeptide can be inserted into an expression vector. By introducing the expression vector into an appropriate host, the encoded C3b/C4b CR-like polypeptide may be produced in large amounts.

Another method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA (oligonucleotides) encoding the amino acid sequence of an C3b/C4b CR-like polypeptide, are then added to the cDNA along with a polymerase such as Taq polymerase, and the polymerase amplifies the cDNA region between the two primers.

Another means of preparing a nucleic acid molecule encoding the amino acid sequence of an C3b/C4b CR-like polypeptide is chemical synthesis using methods well known to the skilled artisan such as those described by Engels et al., *Angew. Chem. Intl. Ed.*, 28:716–734 (1989). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DATA encoding the amino acid sequence of an C3b/C4b CR-like polypeptide will be several hundred nucleotides in length. Nucleic acids larger than about 100 nucleotides can be synthesized as several fragments using these methods. The fragments can then be ligated together to form the full length nucleotide sequence of an C3b/C4b CR-like polypeptide. Usually, the DNA fragment encoding the amino terminus of the polypeptide will have an ATG, which encodes a methionine residue. This methionine may or may not be present on the mature form of the C3b/C4b CR-like polypeptide; depending on whether the polypeptide produced in the host cell is designed to be secreted from that cell. Other methods known to the skilled artisan may be used as well.

In certain embodiments, nucleic acid variants contain codons which have been altered for the optimal expression of an C3b/C4b CR-like polypeptide in a given host cell. Particular codon alterations will depend upon the C3b/C4b CR-like polypeptide(s) and host cell(s) selected for expression. Such "codon optimization" can be carried out by a variety of methods, for example, by selecting codons which are preferred for use in highly expressed genes in a given host cell. Computer algorithms which incorporate codon frequency tables such as "Ecohigh.cod" for codon preference of highly expressed bacterial genes may be used and are provided by the University of Wisconsin Package Version 9.0, Genetics Computer Group, Madison, Wis. Other useful codon frequency tables include "Celegans_high.cod", "Celegans_low.cod", "Drosophila_high.cod", "Human_high.cod", "Maize_high.cod", and "Yeast_high.cod".

Vectors and Host Cells

A nucleic acid molecule encoding the amino acid sequence of an C3b/C4b CR-like polypeptide may be inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of an C3b/C4b CR-like polypeptide may be amplified/expressed in prokaryotic, yeast, insect (baculovirus systems), and/or eukaryotic host cells. Selection of the host cell will depend in part on whether an C3b/C4b CR-like polypeptide is to be post-translationally modified (e.g., glycosylated and/or phosphorylated). If so, yeast, insect, or mammalian host cells are preferable. For a review of expression vectors, see *Meth. Enz.*, v.185, D. V. Goeddel, ed. Academic Press Inc., San Diego, Calif. (1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the C3b/C4b CR-like polypeptide coding sequence; the oligonucleotide sequence encodes polyHis (such as hexaHis), or other "tag" such as FLAG, HA (hemaglutinin Influenza virus) or myc for which commercially available antibodies exist. This tag is typically fused to the polypeptide upon expression of the polypeptide, and can serve as a means for affinity purification of the C3b/C4b CR-like polypeptide from the host cell. Affinity purification can be accomplished, for example, by column chromatography using antibodies against the tag as an affinity matrix. Optionally, the tag can subsequently be removed from the purified C3b/C4b CR-like polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source) or synthetic, or the flanking sequences may be native sequences which normally function to regulate C3b/C4b CR-like polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

The flanking sequences useful in the vectors of this invention may be obtained by any of several methods well known in the art. Typically, flanking sequences useful herein other than the C3b/C4b CR-like gene flanking sequences will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with suitable oligonucleotide and/or flanking sequence fragments from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of an C3b/C4b CR-like polypeptide. If the vector of choice does not contain an origin of replication site, one may be chemically synthesized based on a known sequence, and ligated into the vector. For example, the origin of replication from the plasmid pBR322 (Product No. 303-3s, New England Biolabs, Beverly, Mass.) is suitable for most Gram-negative bacteria and various origins (e.g., SV40, polyoma, adenovirus, vesicular stomatitis virus (VSV) or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G–C rich fragment followed by a poly T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampiclllin resistance gene, and the tetracycline resistance gene. A neomycin resistance gene may also be used for selection in prokaryotic and eukaryotic host cells.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markets for mammalian cells include dihydrofolate reductase (DHFR) and thymidine kinase. The mammalian cell transformants are placed under selection pressure which only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes an C3b/C4b CR-like polypeptide. As a result, increased quantities of C3b/C4b CR-like polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of an C3b/C4b CR-like polypeptide to be expressed. The Shine-Dalgarno sequence is varied but is typically a polypurine (i.e., having a high A–G content). Many Shine-Dalgarno sequences have been identified, each of which can be readily synthesized using methods set forth herein and used in a prokaryotic vector.

A leader, or signal, sequence may be used to direct an C3b/C4b CR-like polypeptide out of the host cell. Typically, a nucleotide sequence encoding the signal sequence is positioned in the coding region of an C3b/C4b CR-like nucleic acid molecule, or directly at the 5' end of an C3b/C4b CR-like polypeptide coding region. Many signal sequences have been identified, and any of those that are functional in the selected host cell may be used in conjunction with an C3b/C4b CR-like nucleic acid molecule. Therefore, a signal sequence may be homologous (naturally occurring) or heterologous to an C3b/C4b CR-like gene or cDNA. Additionally, a signal sequence may be chemically synthesized using methods described herein. In most cases, the secretion of an C3b/C4b CR-like polypeptide from the host cell via the presence of a signal peptide will result in the removal of the signal peptide from the secreted C3b/C4b CR-like polypeptide. The signal sequence may be a component of the vector, or it may be a part of an C3b/C4b CR-like nucleic acid molecule that is inserted into the vector.

Included within the scope of this invention is the use of either a nucleotide sequence encoding a native C3b/C4b CR-like polypeptide signal sequence joined to an C3b/C4b CR-like polypeptide coding region or a nucleotide sequence encoding a heterologous signal sequence joined to an C3b/C4b CR-like polypeptide coding region. The heterologous signal sequence selected should be one that is recognized and processed, i.e., cleaved by a signal peptidase, by the host cell. For prokaryotic host cells that do not recognize and process the native C3B/C4B CR-like polypeptide signal sequence, the signal sequence is substituted by a prokaryotic signal sequence selected, for example, from the group of the alkaline phosphatase, penicillinase, or heat-stable enterotoxin II leaders. For yeast secretion, the native C3B/C4B CR-like polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add presequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the N-terminus. Alternatively, use of some enzyme cleavage sites may result in a slightly truncated form of the desired C3b/C4b CR-like polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the C3b/C4b CR-like gene, especially where the gene used is a full length genomic sequence or a fragment thereof. Where the intron is not naturally occurring within the gene (as for most cDNAs), the intron(s) may be obtained from another source. The position of the intron with respect to flanking sequences and the C3b/C4b CR-like gene is generally important, as the intron must be transcribed to be effective. Thus, when an C3b/C4b CR-like cDNA molecule is being transcribed, the preferred position for the intron is 3' to the transcription start site, and 5' to the polyA transcription termination sequence. Preferably, the intron or introns will be located on one side or the other (i.e., 5' or 3') of the cDNA such that it does not interrupt the coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

The expression and cloning vectors of the present invention will each typically contain a promoter that is recognized by the host organism and operably linked to the molecule encoding a C3B/C4B CR-like polypeptide. Promoters are untranscribed sequences located upstream (5') to the start codon of a structural gene (generally within about 100 to 1000 bp) that control the transcription of the structural gene. Promoters are conventionally grouped into one of two classes, inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding an C3B/C4B CR-like polypeptide by removing the promoter from the source DNA by restriction enzyme digestion and inserting the desired promoter sequence into the vector. The native C3B/C4B CR-like gene promoter sequence may be used to direct amplification and/or expression of an C3B/C4B CR-like nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence(s), using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus (CMV), a retrovirus, hepatitis-B virus and most preferably Simian Virus 40 (SV40). Other suitable mammalian promoters include heterologous mammalian promoters, e.g., heat-shock promoters and the actin promoter.

Additional promoters which may be of interest in controlling C3B/C4B CR-like gene transcription include, but are not limited to: the SV40 early promoter region (Bernoist and Chambon, *Nature,* 290:304–310, 1981); the CMV promoter; the promoter contained in the 3' long terminal repeat of Rous sarcoma virus (Yamamoto et al., *Cell,* 22:787–797, 1980); the herpes thymidine kinase promoter (Wagner et al., *Proc. Natl. Acad. Sci. USA,* 78:144–1445, 1981); the regulatory sequences of the metallothionine gene (Brinster et al., *Nature,* 296:39–42, 1982); prokaryotic expression vectors such as the beta-lactamase promoter (Villa-Kamaroff, et al., *Proc. Natl. Acad. Sci. USA,* 75:3727–3731, 1978); or the tac promoter (DeBoer, et al., *Proc. Natl. Acad. Sci. USA,* 80:21–25, 1983). Also of interest are the following animal transcriptional control regions, which exhibit tissue specificity and have been utilized in transgenic animals: the elastase I gene control region which is active in pancreatic acinar cells (Swift et al., *Cell,* 38:639–646, 1984; Ornitz et al., *Cold Spring Harbor Symp. Quant. Biol.,* 50:399–409 (1986); MacDonald, *Hepatology,* 7:425–515, 1987); the insulin gene control region which is active in pancreatic beta cells (Hanahan, *Nature,* 315:115–122, 1985); the immunoglobulin gene control region which is active in lymphoid cells (Grosschedl et al., *Cell,* 38:647–658 (1984); Adames et al., *Nature,* 318:533–538 (1985); Alexander et al., *Mol. Cell. Biol.,* 7:1436–1444, 1987); the mouse mammary tumor virus control region which is active in testicular, breast, lymphoid and mast cells (Leder et al., *Cell,* 45:485–495, 1986); the albumin gene control region which is active in liver (Pinkert et al., *Genes and Devel.,* 1:268–276, 1987); the alphafetoprotein gene control region which is active in liver (Krumlauf et al., *Mol. Cell. Biol.,* 5:1639–1648, 1985; Hammer et al., *Science,* 235:53–58, 1987); the alpha 1-antitrypsin gene control region which is active in the liver (Kelsey et al., *Genes and Devel.,* 1:161–171, 1987); the beta-globin gene control region which is active in myeloid cells (Mogram et al., *Nature,* 315:338–340, 1985; Kollias et al., *Cell,* 46:89–94, 1986); the myelin basic protein gene control region which is active in oligodendrocyte cells in the brain (Readhead et al., *Cell,* 48:703–712, 1987); the myosin light chain-2 gene control region which is active in skeletal muscle (Sani, *Nature,* 314:283–286, 1985); and the gonadotropic releasing hormone gene control region which is active in the hypothalamus (Mason et al., *Science,* 234:1372–1378, 1986).

An enhancer sequence may be inserted into the vector to increase the transcription of a DNA encoding an C3B/C4B CR-like polypeptide of the present invention by higher eukaryotes. Enhancers are cis-acting elements of DNA, usually about 10–300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to an C3B/C4B CR-like nucleic acid molecule, it is typically located at a site 5' from the promoter.

Expression vectors of the invention may be constructed from a starting vector such as a commercially available vector. Such vectors may or may not contain all of the desired flanking sequences. Where one or more of the desired flanking sequences are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen Company, Carlsbad, Calif.), pBSII (Stratagene Company, La Jolla, Calif.), pET15□ (Novagen, Madison, Wis.), pGEX (Pharmacia Biotech, Piscataway, N.J.), pEGFP-N2 (Clontech, Palo Alto, Calif.), pETL (BlueBacII; Invitrogen), pDSR-alpha (PCT Publication No. No. WO90/14363) and pFastBacDual (Gibco/BRL, Grand Island, N.Y.).

Additional suitable vectors include, but are not limited to, cosmids, plasmids or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast, or virus vectors such as a baculovirus expression system (pBacPAK plasmid derivatives, Clontech, Palo Alto, Calif.).

After the vector has been constructed and a nucleic acid molecule encoding an C3b/C4b CR-like polypeptide has been inserted into the proper site of the vector, the completed vector may be inserted into a suitable host cell for amplification and/or polypeptide expression. The transformation of an expression vector for an C3b/° C4b CR-like polypeptide into a selected host cell may be accomplished by well known methods including methods such as transfection, infection, calcium chloride, electroporation, microinjection, lipofection or the DE/AE-dextran method or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast cell, an insect cell or a vertebrate cell). The host cell, when cultured under appropriate conditions, synthesizes an C3b/C4b CR-like polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), 10801 University Boulevard, Manassas, Va. 20110–2209. Examples include, but are not limited to, mammalian cells, such as Chinese hamster ovary cells (CHO) (ATCC No. CCL61) CHO DHFR-cells (Urlaub et al., *Proc. Natl. Acad. Sci. USA*, 97:4216–4220 (1980)), human embryonic kidney (HEK) 293 or 293T cells (ATCC No. CRL1573), or 3T3 cells (ATCC No. CCL92). The selection of suitable mammalian host cells and methods for transformation, culture, amplification, screening and product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines, which are available from the ATCC. Each of these cell lines is known by and available to those skilled in the art of protein expression.

Similarly useful as host cells suitable for the present invention are bacterial cells. For example, the various strains of *E. coli* (e.g., HB101, (ATCC No. 33694) DH5α, DH10, and MC1061 (ATCC No. 53338)) are well-known as host cells in the field of biotechnology. Various strains of *B. subtilis*, Pseudomonas spp., other Bacillus spp., Streptomyces spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described for example in Kitts et al., *Biotechniques*, 14:810–817 (1993); Lucklow, *Curr. Opin. Biotechnol.*, 4:564–572 (1993); and Lucklow et al. (*J. Virol.*, 67:4566–4579 (1993). Preferred insect cells are Sf-9 and Hi5 (Invitrogen, Carlsbad, Calif.).

One may also use transgenic animals to express glycosylated C3b/C4b CR-like polypeptides. For example, one may use a transgenic milk-producing animal (a cow or goat, for example) and obtain the present glycosylated polypeptide in the animal milk. One may also use plants to produce C3b/C4b CR-like polypeptides, however, in general, the glycosylation occurring in plants is different from that produced in mammalian cells, and may result in a glycosylated product which is not suitable for human therapeutic use.

Polypeptide Production

Host cells comprising an C3b/C4b CR-like polypeptide expression vector may be cultured using standard media well known to the skilled artisan. The media will usually contain all nutrients necessary for the growth and survival of the cells. Suitable media for culturing E. coli cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as indicated by the particular cell line being cultured. A suitable medium for insect cultures is Grace's medium supplemented with yeastolate, lactalbumin hydrolysate and/or fetal calf serum, as necessary.

Typically, an antibiotic or other compound useful for selective growth of transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of an C3b/C4b CR-like polypeptide produced by a host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If an C3b/C4b CR-like polypeptide has been designed to be secreted from the host cells, the majority of polypeptide may be found in the cell culture medium. If however, the C3b/C4b CR-like polypeptide is not secreted from the host cells, it will be present in the cytoplasm and/or the nucleus (for eukaryotic host cells) or in the cytosol (for bacterial host cells).

For an C3b/C4b CR-like polypeptide situated in the host cell cytoplasm and/or the nucleus (for eukaryotic host cells) or in the cytosol (for bacterial host cells), intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If an C3b/C4b CR-like polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The C3b/C4b CR-like polypeptide in its now soluble form can then be analyzed using gel electrophoresis, immunoprecipitation or the like. If it is desired to isolate the C3b/C4b CR-like polypeptide, isolation may be accomplished using standard methods such as those described herein and in Marston et al., Meth. Enz., 182:264–275 (1990).

In some cases, an C3b/C4b CR-like polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/dithiane DTT, and 2-2mercaptoethanol(bME)/dithio-b(ME). A cosolvent may be used to increase the efficiency of the refolding, and the more common reagents used for this purpose include glycerol, polyethylene glycol of various molecular weights, arginine and the like.

If inclusion bodies are not formed to a significant degree upon expression of an C3b/C4b CR-like polypeptide, then the polypeptide will be found primarily in the supernatant after centrifugation of the cell homogenate. The polypeptide may be further isolated from the supernatant using methods such as those described herein.

The purification of an C3b/C4b CR-like polypeptide from solution can be accomplished using a variety of techniques. If the polypeptide has been synthesized such that it contains a tag such as Hexahistidine (C3b/C4b CR-like polypeptide/hexaHis) or other small peptide such as FLAG (Eastman Kodak Co., New Haven, Conn.) or myc (Invitrogen, Carlsbad, Calif.) at either its carboxyl or amino terminus, it may be purified in a one-step process by passing the solution through an affinity column where The column matrix has a high affinity for the tag.

For example, polyhistidine binds with great affinity and specificity to nickel, thus an affinity column of nickel (such as the Qiagen® nickel columns) can be used for purification of C3b/C4b CR-like polypeptide/polyHis. See for example, Ausubel et al., eds., Current Protocols in Molecular Biology, Section 10.11.8, John Wiley & Sons, New York (1993).

Additionally, the C3B/C4B CR-like polypeptide may be purified through the use of a monoclonal antibody which is capable of specifically recognizing and binding to the C3B/C4B CR-like polypeptide.

Suitable procedures for purification thus include, without limitation, affinity chromatography, immunoaffinity chromatography, ion exchange chromatography, molecular sieve chromatography, High Performance Liquid Chromatography (HPLC), electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

C3b/C4b CR-like polypeptides may also be prepared by chemical synthesis methods (such as solid phase peptide synthesis) using techniques known in the art, such as those set forth by Merrifield et al., J. Am. Chem. Soc., 85:2149 (1963), Houghten et al., Proc Natl Acad. Sci. USA, 82:5132 (1985), and Stewart and Young, Solid Phase Peptide Synthesis, Pierce Chemical Co., Rockford, Ill. (1984). Such polypeptides may be synthesized with or without a methionine on the amino terminus. Chemically synthesized C3b/C4b CR-like polypeptides may be oxidized using methods set forth in these references to form disulfide bridges. Chemically synthesized C3b/C4b CR-like polypeptides are expected to have comparable biological activity to the corresponding C3b/C4b CR-like polypeptides produced recombinantly or purified from natural sources, and thus may be used interchangeably with a recombinant or natural C3b/C4b CR-like polypeptide.

Another means of obtaining an C3b/C4b CR-like polypeptide is via purification from biological samples such as source tissues and/or fluids in which the C3b/C4b CR-like polypeptide is naturally found. Such purification can be conducted using methods for protein purification as described herein. The presence of the C3b/C4b CR-like polypeptide during purification may be monitored using, for example, an antibody prepared against recombinantly produced C3b/C4b CR-like polypeptide or peptide fragments thereof.

A number of additional methods for producing nucleic acids and polypeptides are known in the art, and can be used to produce polypeptides having specificity for C3b/C4b CR-like. See for example, Roberts et al., *Proc. Natl. Acad. Sci.*, 94:12297–12303 (1997), which describes the production of fusion proteins between an mRNA and its encoded peptide. See also Roberts, R., *Curr. Opin. Chem. Biol.*, 3:268–273 (1999). Additionally, U.S. Pat. No. 5,824,469 describes methods of obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those which exhibit a predetermined biological function. From that subpopulation, oligonucleotides capable of carrying out the desired biological function are isolated.

U.S. Pat. Nos. 5,763,192, 5,814,476, 5,723,323, and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive protein expression libraries, which can subsequently be used for high throughput phenotypic screening in a variety of assays, such as biochemical assays, cellular assays, and whole organism assays (e.g., plant, mouse, etc.).

Chemical Derivatives

Chemically modified derivatives of the C3b/C4b CR-like polypeptides may be prepared by one skilled in the art, given the disclosures set forth hereinbelow. C3b/C4b CR-like polypeptide derivatives are modified in a manner that is different, either in the type or location of the molecules naturally attached to the polypeptide. Derivatives may include molecules formed by the deletion of one or more naturally-attached chemical groups. The polypeptide comprising the amino acid sequence of SEQ ID NO:2 or SEQ ID NO:4, or an C3b/C4b CR-like polypeptide variant may be modified by the covalent attachment of one or more polymers. For example, the polymer selected is typically water soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water soluble polymer, some molecules will weigh more, some less, than the stated molecular weight). The average molecular weight of each polymer preferably is between about 5 kDa and about 50 kDa, more preferably between about 12 kDa and about 40 kDa and most preferably between about 20 kDa and about 35 kDa.

Suitable water soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$–$C_{10}$) alkoxy- or aryloxy-polyethylene glycol), monomethoxy-polyethylene glycol, dextran (such as low molecular weight dextran, of, for example about 6 kD), cellulose, or other carbohydrate based polymers, poly-(N-vinyl pyrrolidone) polyethylene glycol, propylene glycol homopolymers, a polypropylene oxide/ethylene oxide copolymer, polyoxyethylated polyols (e.g., glycerol) and polyvinyl alcohol. Also encompassed by the present invention are bifunctional crosslinking molecules which may be used to prepare covalently attached multimers of the polypeptide comprising the amino acid sequence of SEQ ID NO:2 or SEQ ID NO:4 or an C3b/C4b CR-like polypeptide variant.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the polypeptide comprising the amino acid sequence of SEQ ID NO:2 or SEQ ID NO:4, or an C3b/C4b CR-like polypeptide variant becomes attached to one or more polymer molecules, and (b) obtaining the reaction product(s). The optimal reaction conditions will be determined based on known parameters and the desired result. For example, the larger the ratio of polymer molecules:protein, the greater the percentage of attached polymer molecule. In one embodiment, the C3b/C4b CR-like polypeptide derivative may have a single polymer molecule moiety at the amino terminus. See, for example, U.S. Pat. No. 5,234,784.

The pegylation of the polypeptide specifically may be carried out by any of the pegylation reactions known in the art, as described for example in the following references: Francis et al., *Focus on Growth Factors*, 3:4–10 (1992); EP 0154316; EP 0401384 and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono $C_1$–$C_{10}$ alkoxy or aryloxy derivatives thereof (see U.S. Pat. No. 5,252,714).

In another embodiment, C3b/C4b CR-like polypeptides may be chemically coupled to biotin, and the biotin/C3b/C4b CR-like polypeptide molecules which are conjugated are then allowed to bind to avidin, resulting in tetravalent avidin/biotin/C3b/C4b CR-like polypeptide molecules. C3b/C4b CR-like polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions which may be alleviated or modulated by the administration of the present C3b/C4b CR-like polypeptide derivatives include those described herein for C3b/C4b CR-like polypeptides. However, the C3b/C4b CR-like polypeptide derivatives disclosed herein may have additional activities, enhanced or reduced biological activity, or other characteristics, such as increased or decreased half-life, as compared to the non-derivatized molecules.

Genetically Engineered Non-human Animals

Additionally included within the scope of the present invention are non-human animals such as mice, rats, or other rodents, rabbits, goats, or sheep, or other farm animals, in which the gene (or genes) encoding the native C3b/C4b CR-like polypeptide has (have) been disrupted ("knocked out") such that the level of expression of this gene or genes is (are) significantly decreased or completely abolished. Such animals may be prepared using techniques and methods such as those described in U.S. Pat. No. 5,557,032.

The present invention further includes non-human animals such as mice, rats, or other rodents, rabbits, goats, sheep, or other farm animals, in which either the native form of the C3b/C4b CR-like gene(s) for that animal or a heterologous C3b/C4b CR-like gene(s) is (are) over-expressed by the animal, thereby creating a "transgenic" animal. Such transgenic animals may be prepared using well known methods such as those described in U.S. Pat. No. 5,489,743 and PCT application No. WO94/28122.

The present invention further includes non-human animals in which the promoter for one or more of the C3b/C4b CR-like polypeptides of the present invention is either activated or inactivated (e.g., by using homologous recombination methods) to alter the level of expression of one or more of the native C3b/C4b CR-like polypeptides.

These non-human animals may be used for drug candidate screening. In such screening, the impact of a drug candidate on the animal may be measured. For example, drug candidates may decrease or increase the expression of the C3b/C4b CR-like gene. In certain embodiments, the amount of C3b/C4b CR-like polypeptide, that is produced may be measured after the exposure of the animal to the drug candidate. Additionally, in certain embodiments, one may detect the actual impact of the drug candidate on the animal. For example, the overexpression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Microarray

It will be appreciated that DNA microarray technology can be utilized in accordance with the present invention. DNA microarrays are miniature, high density arrays of nucleic acids positioned on a solid support, such as glass. Each cell or element within the array has numerous copies of a single species of DNA which acts as a target for hybridization for its cognate mRNA. In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA which is specifically bound to each target DNA. In this way, the expression of thousands of genes can be quantitated in a high throughput, parallel manner from a single sample of biological material.

This high throughput expression profiling has a broad range of applications with respect to the C3b/C4b CR-like molecules of the invention, including, but not limited to: the identification and validation of C3b/C4b CR-like disease-related genes as targets for therapeutics; molecular toxicology of C3b/C4b CR-like molecules and inhibitors thereof; stratification of populations and generation of surrogate markers for clinical trials; and enhancing C3b/C4b CR-like-related small molecule drug discovery by aiding in the identification of selective compounds in high throughput screens (HTS).

Selective Binding Agents

As used herein, the term "selective binding agent" refers to a molecule which has specificity for one or more C3b/C4b CR-like polypeptides. Suitable selective binding agents include, but are not limited to, antibodies and derivatives thereof, polypeptides, and small molecules. Suitable selective binding agents may be prepared using methods known in the art. An exemplary C3B/C4B CR-like polypeptide selective binding agent of the present invention is capable of binding a certain portion of the C3B/C4B CR-like polypeptide thereby inhibiting the binding of the polypeptide to the C3B/C4B CR-like polypeptide receptor(s).

Selective binding agents such as antibodies and antibody fragments that bind C3b/C4b CR-like polypeptides are within the scope of the present invention. The antibodies may be polyclonal including monospecific polyclonal, monoclonal (MAbs), recombinant, chimeric, humanized such as CDR-grafted, human, single chain, and/or bispecific, as well as fragments, variants or derivatives thereof. Antibody fragments include those portions of the antibody which bind to an epitope on the C3B/C4B CR-like polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward an C3b/C4b CR-like polypeptide generally are produced in animals (e.g., rabbits or mice) by means of multiple subcutaneous or intraperitoneal injections of C3b/C4b CR-like polypeptide and an adjuvant. It may be useful to conjugate an C3b/C4b CR-like polypeptide to a carrier protein that is immunogenic in the species to be immunized, such as keyhole limpet heocyanin, serum, albumin, bovine thyroglobulin, or soybean trypsin inhibitor. Also, aggregating agents such as alum are used to enhance the immune response. After immunization, the animals are bled and the serum is assayed for anti-C3b/C4b CR-like polypeptide antibody titer.

Monoclonal antibodies directed toward an C3b/C4b CR-like polypeptide are produced using any method which provides for the production of antibody molecules by continuous cell lines in culture. Examples of suitable methods for preparing monoclonal antibodies include the hybridoma methods of Kohler et al., *Nature*, 256:495–497 (1975) and the human B-cell hybridoma method, Kozbor, *J. Immunol.*, 133:3001 (1984); Brodeur et al., Monoclonal Antibody Production Techniques and Applications, pp. 51–63 (Marcel Dekker, Inc., New York, 1987). Also provided by the invention are hybridoma cell lines which produce monoclonal antibodies reactive with C3b/C4b CR-like polypeptides.

Monoclonal antibodies of the invention may be modified for use as therapeutics. One embodiment is a "chimeric" antibody in which a portion of the heavy and/or light chain is identical with or homologous to a corresponding sequence in antibodies derived from a particular species or belonging to a particular antibody class or subclass, while the remainder of the chain(s) is identical with or homologous to a corresponding sequence in antibodies derived from another species or belonging to another antibody class or subclass. Also included are fragments of such antibodies, so long as they exhibit the desired biological activity. See, U.S. Pat. No. 4,816,567; Morrison et al., *Proc. Natl. Acad. Sci.*, 81:6851–6855 (1985).

In another embodiment, a monoclonal antibody of the invention is a "humanized" antibody. Methods for humanizing non-human antibodies are well known in the art. See U.S. Pat. Nos. 5,585,089, and 5,693,762. Generally, a humanized antibody has one or more amino acid residues introduced into it from a source which is non-human. Humanization can be performed, for example, using methods described in the art (Jones et al., *Nature* 321:522–525 (1986); Riechmann et al., *Nature*, 332:323–327 (1988); Verhoeyen et al., *Science* 239:1534–1536 (1988)), by substituting at least a portion of a rodent complementarity-determining region (CDR) for the corresponding regions of a human antibody.

Also encompassed by the invention are human antibodies which bind C3b/C4b CR-like polypeptides. Using transgenic animals (e.g., mice) that are capable of producing a repertoire of human antibodies in the absence of endogenous immunoglobulin production such antibodies are produced by immunization with an C3b/C4b CR-like antigen (i.e., having at least 6 contiguous amino acids), optionally conjugated to a carrier. See, for example, Jakobovits et al., *Proc. Natl. Acad. Sci.*, 90:2551–2555 (1993); Jakobovits et al., *Nature* 362:255–258 (1993); Bruggemann et al., *Year in Immuno.*, 7:33 (1993). In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human (rather than e.g., murine) amino acid sequences, including variable regions which are immunospecific for these antigens. See PCT application nos. PCT/US96/05928 and PCT/US93/06926. Additional methods are described in U.S. Pat. No. 5,545,807, PCT application nos. PCT/US91/245, PCT/GB89/01207, and in EP 546073B1 and EP 546073A1. Human antibodies may also be produced by the expression of recombinant DNA in host cells or by expression in hybridoma cells as described herein.

In an alternative embodiment, human antibodies can be produced from phage-display libraries (Hoogenboom et al., *J. Mol. Biol.* 227:381 (1991); Marks et al., *J. Mol. Biol.* 222:581 (1991). These processes mimic immune selection through the display of antibody repertoires on the surface of filamentous bacteriophage, and subsequent selection of phage by their binding to an antigen of choice. One such technique is described in PCT Application no. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-C3b/C4b CR-like antibodies of the invention may be employed in any known assay method, such as competitive binding assays, direct and indirect sandwich assays, and immunoprecipitation assays (Zola, Monoclonal Antibodies: A Manual of Techniques, pp. 147–158 (CRC Press, Inc., 1987)) for the detection and quantitation of C3b/C4b CR-like polypeptides. The antibodies will bind C3b/C4b CR-like polypeptides with an affinity which is appropriate for the assay method being employed.

For diagnostic applications, in certain embodiments, anti-C3b/C4b CR-like antibodies may be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, $\square$-galactosidase, or horseradish peroxidase (Bayer et al., *Meth. Enz.*, 184:138–163 (1990)).

Competitive binding assays rely on the ability of a labeled standard (e.g., an C3b/C4b CR-like polypeptide, or an immunologically reactive portion thereof) to compete with the test sample analyte (an C3b/C4b CR-like polypeptide) for binding with a limited amount of anti C3b/C4b CR-like antibody. The amount of an C3b/C4b CR-like polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-C3b/C4b CR-like antibodies, also are useful for in vivo imaging. An antibody labeled with a detectable moiety may be administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of an C3b/C4b CR-like polypeptide. In one embodiment, antagonist antibodies of the invention are antibodies or binding fragments thereof which are capable of specifically binding to an C3b/C4b CR-like polypeptide and which are capable of inhibiting or eliminating the functional activity of an C3b/C4b CR-like polypeptide in vivo or in vitro. In preferred embodiments, the selective binding agent, e.g., an antagonist antibody, will inhibit the functional activity of an C3b/C4b CR-like polypeptide by at least about 50%, and preferably by at least about 80%. In another embodiment, the selective binding agent may be an antibody that is capable of interacting with an C3b/C4b CR-like binding partner (a ligand or receptor) thereby inhibiting or eliminating C3b/C4b CR-like activity in vitro or in vivo. Selective binding agents, including agonist and antagonist anti-C3b/C4b CR-like antibodies, are identified by screening assays which are well known in the art.

The invention also relates to a kit comprising C3b/C4b CR-like selective binding agents (such as antibodies) and other reagents useful for detecting C3b/C4b CR-like polypeptide levels in biological samples. Such reagents may include, a detectable label, blocking serum, positive and negative control samples, and detection reagents.

C3b/C4b CR-like polypeptides can be used to clone C3b/C4b CR-like ligand(s) using an "expression cloning" strategy. Radiolabeled (125-Iodine) C3b/C4b CR-like polypeptide or "affinity/activity-tagged" C3b/C4b CR-like polypeptide (such as an Fc fusion or an alkaline phosphatase fusion) can be used in binding assays to identify a cell type or cell line or tissue that expresses C3b/C4b CR-like ligand (s). RNA isolated from such cells or tissues can then be converted to cDNA, cloned into a mammalian expression vector, and transfected into mammalian cells (for example, COS, or 293) to create an expression library. Radiolabeled or tagged C3b/C4b CR-like polypeptide can then be used as an affinity reagent to identify and isolate the subset of cells in this library expressing C3b/C4b CR-like ligand(s). DNA is then isolated from these cells and transfected into mammalian cells to create a secondary expression library in which the fraction of cells expressing C3b/C4b CR-like ligand(s) would be many-fold higher than in the original library. This enrichment process can be repeated iteratively until a single recombinant clone containing an C3b/C4b CR-like ligand is isolated. Isolation of C3b/C4b CR-like ligand(s) is useful for identifying or developing novel agonists and antagonists of the C3b/C4b CR-like signaling pathway. Such agonists and antagonists include C3b/C4b CR-like ligand(s), anti-C3b/C4b CR-like ligand antibodies, small molecules or antisense oligonucleotides.

Assaying for other Modulators of C3b/C4b CR-like Polypeptide Activity

In some situations, it may be desirable to identify molecules that are modulators, i.e., agonists or antagonists, of the activity of C3b/C4b CR-like polypeptide. Natural or synthetic molecules that modulate C3b/C4b CR-like polypeptide may be identified using one or more screening assays, such as those described herein. Such molecules may be administered either in an ex vivo manner, or in an in vivo manner by injection, or by oral delivery, implantation device, or the like.

"Test molecule(s)" refers to the molecule(s) that is/are under evaluation for the ability to modulate (i.e., increase or decrease) the activity of an C3b/C4b CR-like polypeptide. Most commonly, a test molecule will interact directly with an C3b/C4b CR-like polypeptide. However, it is also contemplated that a test molecule may also modulate C3b/C4b CR-like polypeptide activity indirectly, such as by affecting C3b/C4b CR-like gene expression, or by binding to an C3b/C4b CR-like binding partner (e.g., receptor or ligand). In one embodiment, a test molecule will bind to an C3b/C4b CR-like polypeptide with an affinity constant of at least about $10^{-6}$ M, preferably about $10^{-8}$ M, more preferably about $10^{-9}$ M, and even more preferably about $10^{-10}$ M.

Methods for identifying compounds which interact with C3b/C4b CR-like polypeptides are encompassed by the present invention. In certain embodiments, an C3b/C4b CR-like polypeptide is incubated with a test molecule under conditions which permit the interaction of the test molecule with an C3b/C4b CR-like polypeptide, and the extent of the interaction can be measured. The test molecule(s) can be screened in a substantially purified form or in a crude mixture.

In certain embodiments, an C3b/C4b CR-like polypeptide agonist or antagonist may be a protein, peptide, carbohydrate, lipid, or small molecular weight molecule which interacts with C3b/C4b CR-like polypeptide to regulate its activity. Molecules which regulate C3b/C4b CR-like polypeptide expression include nucleic acids which are complementary to nucleic acids encoding an C3b/C4b CR-like polypeptide, or are complementary to nucleic acids sequences which direct or control the expression of C3b/C4b CR-like polypeptide, and which act as anti-sense regulators of expression.

Once a set of test molecules has been identified as interacting with an C3b/C4b CR-like polypeptide, the molecules may be further evaluated for their ability to increase or decrease C3b/C4b CR-like polypeptide activity. The measurement of the interaction of test molecules with C3b/C4b CR-like polypeptides may be carried out in several formats, including cell-based binding assays, membrane binding assays, solution-phase assays and immunoassays. In general, test molecules are incubated with an C3b/C4b CR-like polypeptide for a specified period of time, and C3b/C4b CR-like polypeptide activity is determined by one or more assays for measuring biological activity.

The interaction of test molecules with C3b/C4b CR-like polypeptides may also be assayed directly using polyclonal or monoclonal antibodies in an immunoassay. Alternatively, modified forms of C3b/C4b CR-like polypeptides containing epitope tags as described herein may be used in immunoassays.

In the event that C3b/C4b CR-like polypeptides display biological activity through an interaction with a binding partner (e.g., a receptor or a ligand), a variety of in vitro assays may be used to measure the binding of an C3b/C4b CR-like polypeptide to the corresponding binding. partner (such as a selective binding agent, receptor, or ligand). These assays may be used to screen test molecules for their ability to increase or decrease the rate and/or the extent of binding of an C3b/C4b CR-like polypeptide to its binding partner. In one assay, an C3b/C4b CR-like polypeptide is immobilized in the wells of a microtiter plate. Radiolabeled C3b/C4b CR-like binding partner (for example, iodinated C3b/C4b CR-like binding partner) and the test molecule(s) can then be added either one at a time (in either order) or simultaneously to the wells. After incubation, the wells can be washed and counted, using a scintillation counter, for radioactivity to determine the extent to which the binding partner bound to C3b/C4b CR-like polypeptide. Typically, the molecules will be tested over a range of concentrations, and a series of control wells lacking one or more elements of the test assays can be used for accuracy in the evaluation of the results. An alternative to this method involves reversing the "positions" of the proteins, i.e., immobilizing C3b/C4b CR-like binding partner to the microtiter plate wells, incubating with the test molecule and radiolabeled C3b/C4b CR-like polypeptide, and determining the extent of C3b/C4b CR-like polypeptide binding. See, for example, chapter 18, *Current Protocols in Molecular Biology,* Ausubel et al., eds., John Wiley & Sons, New York, N.Y. (1995).

As an alternative to radiolabelling, an C3b/C4b CR-like polypeptide or its binding partner may be conjugated to biotin and the presence of biotinylated protein can then be detected using streptavidin linked to an enzyme, such as horseradish peroxidase (HRP) or alkaline phosphatase (AP), that can be detected colorometrically, or by fluorescent tagging of streptavidin. An antibody directed to an C3b/C4b CR-like polypeptide or to an C3b/C4b CR-like binding partner and conjugated to biotin may also be used and can be detected after incubation with enzyme-linked streptavidin linked to AP or HRP.

An C3b/C4b CR-like polypeptide or an C3b/C4b CR-like binding partner can also be immobilized by attachment to agarose beads, acrylic beads or other types of such inert solid phase substrates. The substrate-protein complex can be placed in a solution containing the complementary protein and the test compound. After incubation, the beads can be precipitated by centrifugation, and the amount of binding between an C3b/C4b CR-like polypeptide and its binding partner can be assessed using the methods described herein. Alternatively, the substrate-protein complex can be immobilized in a column, and the test molecule and complementary protein are passed through the column. The formation of a complex between an C3b/C4b CR-like polypeptide and its binding partner can then be assessed using any of the techniques set forth herein, i.e., radiolabelling, antibody binding, or the like.

Another in vitro assay that is useful for identifying a test molecule which increases or decreases the formation of a complex between an C3b/C4b Complement Receptor polypeptide and an C3b/C4b CR-like binding partner is a surface plasmon resonance detector system such as the BIAcore assay system (Pharmacia, Piscataway, N.J.). The BIAcore system may be carried out using the manufacturer's protocol. This assay essentially involves the covalent binding of either C3b/C4b CR-like polypeptide or an C3b/C4b CR-like binding partner to a dextran-coated sensor chip which is located in a detector. The test compound and the other complementary protein can then be injected, either simultaneously or sequentially, into the chamber containing the sensor chip. The amount of complementary protein that binds can be assessed based on the change in molecular mass which is physically associated with the dextran-coated side of the sensor chip; the change in molecular mass can be measured by the detector system.

In some cases, it may be desirable to evaluate two or more test compounds together for their ability to increase or decrease the formation of a complex between an C3b/C4b CR-like polypeptide and an C3b/C4b CR-like binding partner. In these cases, the assays set forth herein can be readily modified by adding such additional test compound(s) either simultaneous with, or subsequent to, the first test compound. The remainder of the steps in the assay are as set forth herein.

In vitro assays such as those described herein may be used advantageously to screen large numbers of compounds for effects on complex formation by C3b/C4b CR-like polypeptide and C3b/C4b CR-like binding partner. The assays may be automated to screen compounds generated in phage display, synthetic peptide, and chemical synthesis libraries.

Compounds which increase or decrease the formation of a complex between an C3b/C4b CR-like polypeptide and an C3b/C4b CR-like binding partner may also be screened in cell culture using cells and cell lines expressing either C3b/C4b CR-like polypeptide or C3b/C4b CR-like binding partner. Cells and cell lines may be obtained from any mammal, but preferably will be from human or other primate, canine, or rodent sources. The binding of an C3b/C4b CR-like polypeptide to cells expressing C3b/C4b CR-like binding partner at the surface is evaluated in the presence or absence of test molecules, and the extent of binding may be determined by, for example, flow cytometry using a biotinylated antibody to an C3b/C4b CR-like binding partner. Cell culture assays can be used advantageously to further evaluate compounds that score positive in protein binding assays described herein.

Cell cultures can also be used to screen the impact of a drug candidate. For example, drug candidates may decrease or increase the expression of the C3b/C4b CR-like gene. In certain embodiments, the amount of C3b/C4b CR-like polypeptide that is produced may be measured after exposure of the cell culture to the drug candidate. In certain embodiments, one may detect the actual impact of the drug candidate on the cell culture. For example, the overexpression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

A yeast two hybrid system (Chien et al., *Proc. Natl. Acad. Sci. USA,* 88:9578–9583 (1991)) can be used to identify novel polypeptides that bind to, or interact with, C3b/C4b CR-like polypeptides. As an example, hybrid constructs comprising DNA encoding a cytoplasmic domain of an C3b/C4b CR-like polypeptide fused to a yeast GAL4-DNA binding domain may be used as a two-hybrid bait plasmid. Positive clones emerging from the screening may be characterized further to identify interacting proteins.

Internalizing Proteins

The tat protein sequence (from HIV) can be used to internalize proteins into a cell. See e.g., Faiwell et al., *Proc. Natl. Acad. Sci.*, 91:664–668 (1994). For example, an 11 amino acid sequence (YGRKKRRQRRR) (SEQ ID NO: 6) of the HIV tat protein (termed the "protein transduction domain", or TAT PDT) has been described as mediating delivery across the cytoplasmic membrane and the nuclear membrane of a cell. See Schwarze et al., *Science*, 285:1569–1572 (1999); and Nagahara et al., *Nature Medicine*, 4:1449–1452 (1998). In these procedures, FITC-constructs (FITC-GGGGYGRKKRRQRRR) (SEQ ID NO: 7) are prepared which bind to cells as observed by fluorescence-activated cell sorting (FACS) analysis, and these constructs penetrate tissues after i.p. administration. Next, tat-bgal fusion proteins are constructed. Cells treated with this construct demonstrated b-gal activity. Following injection, a number of tissues, including liver, kidney, lung, heart, and brain tissue have been found to demonstrate expression using these procedures. It is believed that these constructions underwent some degree of unfolding in order to enter the cell; as such, refolding may be required after entering the cell.

It will thus be appreciated that the tat protein sequence may be used to internalize a desired protein or polypeptide into a cell. For example, using the tat protein sequence, an C3b/C4b CR-like antagonist (such as an anti-C3b/C4b CR-like selective binding agent, small molecule, soluble receptor, or antisense oligonucleotide) can be administered intracellularly to inhibit the activity of an C3b/C4b CR-like molecule. As used herein, the term "C3b/C4b CR-like molecule" refers to both C3b/C4b CR-like nucleic acid molecules and C3b/C4b CR-like polypeptides as defined herein. Where desired, the C3b/C4b CR-like protein itself may also be internally administered to a cell using these procedures. See also, Strauss, E., "Introducing Proteins Into the Body's Cells", *Science*, 285:1466–1467 (1999).

Therapeutic Uses

A non-exclusive list of acute and chronic diseases which can be treated, diagnosed, ameliorated, or prevented with the polypeptides and nucleic acids of the invention is set forth below.

C3b/C4b CR-related protein may act to stimulate the activation of the complement system, which acts alone and in conjunction with antibodies to destroy cells that are foreign to the host and is a main defense against bacterial and viral infections. The ability of a binding partner to bind to and activate C3b/C4b CR-related protein may lead to complement activation. Such a binding partner can be an agonist of C3b/C4b-CR related protein, such as antibody, peptibody, peptide, carbohydrate, polynucleotide, or small molecular weight organic molecule. Agonists of C3b/C4b CR-related protein may be used to prevent and treat conditions characterized by insufficient or defective complement activation, such as bacterial and viral infections.

Alternatively, it may be desirable to use an antagonist of C3b/C4b CR-related protein to block complement activation. An antagonist would be useful for preventing and treating conditions characterized by excessive complement activation, particularly immune system disorders such as rheumatoid arthritis, psioriatic arthritis, inflammatory arthritis, osteoarthritis, inflammatory joint disease, autoimmune disease, multiple sclerosis, lupus, diabetes, inflammatory bowel disease, transplant rejection, and graft versus host disease. Antagonists would also be useful for prevent or treating undesired complement-mediated damage to cells and tissues. In one embodiment, an antagonist comprises a soluble domain of a C3b/C4b CR-related protein.

Other uses for agonists and antagonists of C3b/C4b CR-like molecules include the diagnosis, prevention and treatment of nervous system disorders, such as stroke, Alzheimer's disease, brain injury, and Parkinson's disease; damaged tissues, such as by wounds and burns; ischemic conditions, such as atherosclerosis, restenosis, myocardial infarction, angioplasty, hypertension, and ischemia; metabolic disorders, such as obesity, diabetes, and cachexia; and reproductive disorders, infertility, miscarriage, preterm labor and delivery, and endometriosis.

Other diseases associated with undesirable levels of C3b/C4b CR-related protein are encompassed within the scope of the invention. Undesirable levels include excessive and/or sub-normal levels of C3b/C4b CR-related protein as described herein.

C3b/C4b CR-like Compositions and Administration

Therapeutic compositions are within the scope of the present invention. Such C3B/C4B CR-like pharmaceutical compositions may comprise a therapeutically effective amount of an C3b/C4b CR-like polypeptide or an C3b/C4b CR-like nucleic acid molecule in admixture with a pharmaceutically or physiologically acceptable formulation agent selected for suitability with the mode of administration. Pharmaceutical compositions may comprise a therapeutically effective amount of one or more C3b/C4b CR-like selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine), antimicrobials, antioxidants (such as ascorbic acid, sodium sulfite or sodium hydrogen-sulfite), buffers (such as borate, bicarbonate, Tris-HCl, citrates, phosphates, other organic acids), bulking agents (such as mannitol or glycine), chelating agents (such as ethylenediamine tetraacetic acid (EDTA)), complexing agents (such as caffeine, polyvinylpyrrolidone, beta-cyclodextrin or hydroxypropyl-beta-cyclodextrin), fillers, monosaccharides, disaccharides, and other carbohydrates (such as glucose, mannose, or dextrins), proteins (such as serum albumin, gelatin or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid or hydrogen peroxide), solvents (such as glycerin, propylene glycol or polyethylene glycol), sugar alcohols (such as mannitol or sorbitol), suspending agents, surfactants or wetting agents (such as pluronics, PEG, sorbitan esters, polysorbates such as polysorbate 20, polysorbate 80, triton, tromethamine, lecithin, cholesterol, tyloxapal), stability enhancing agents (sucrose or sorbitol), tonicity enhancing agents (such as alkali metal halides (preferably sodium or potassium chloride), mannitol sorbitol), delivery vehicles, diluents, excipients and/or pharmaceutical adjuvants. (*Remington's Pharmaceutical Sciences*, 18th Edition, A. R. Gennaro, ed., Mack Publishing Company [1990]).

The optimal pharmaceutical composition will be determined by one skilled in the art depending upon, for example, the intended route of administration, delivery format, and desired dosage. See for example, *Remington's Pharmaceutical Sciences*, supra. Such compositions may influence the physical state, stability, rate of in vivo release, and rate of in vivo clearance of the C3b/C4b CR-like molecule.

The primary vehicle or carrier in a pharmaceutical composition may be either aqueous or non-aqueous in nature. For example, a suitable vehicle or carrier may be water for injection, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0–8.5, or acetate buffer of about pH 4.0–5.5, which may further include sorbitol or a suitable substitute therefor. In one embodiment of the present invention, C3b/C4b CR-like polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the C3b/C4b CR-like polypeptide product may be formulated as a lyophilizate using appropriate excipients such as sucrose.

The C3b/C4b CR-like pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired C3b/C4b CR-like molecule in a pharmaceutically acceptable vehicle. A particularly suitable vehicle for parenteral injection is sterile distilled water in which a C3b/C4b CR-like molecule is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), or beads, or liposomes, that provides for the controlled or sustained release of the product which may then be delivered as a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, an C3b/C4b CR-like molecule may be formulated as a dry powder for inhalation. C3b/C4b CR-like polypeptide or C3b/C4b CR-like nucleic acid molecule inhalation solutions may also be formulated with a propellant for aerosol delivery. In yet another embodiment, solutions may be nebulized. Pulmonary administration is further described in PCT application no. PCT/US94/001875, which describes pulmonary delivery of chemically modified proteins.

It is also contemplated that certain formulations may be administered orally. In one embodiment of the present invention, C3b/C4b CR-like molecules which are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the C3b/C4b CR-like molecule. Diluents, flavorings, low melting point waxes, vegetable oils, lubricants, suspending agents, tablet disintegrating agents, and binders may also be employed.

Another pharmaceutical composition may involve an effective quantity of C3b/C4b CR-like molecules in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional C3b/C4b CR-like pharmaceutical compositions will be evident to those skilled in the art, including formulations involving C3b/C4b CR-like polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 which describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., *Biopolymers*, 22:547–556 (1983)), poly (2-hydroxyethyl-methacrylate) (Langer et al., *J. Biomed. Mater. Res.*, 15:167–277 (1981) and Langer, *Chem. Tech.*, 12:98–105 (1982)), ethylene vinyl acetate (Langer et al., supra) or poly-D(−)-3-hydroxybutyric acid (EP 133,988). Sustained-release compositions also may include liposomes, which can be prepared by any of several methods known in the art. See e.g., Eppstein et al., *Proc. Natl. Acad. Sci. USA*, 82:3688–3692 (1985); EP 36,676; EP 88,046; EP 143,949.

The C3b/C4b CR-like pharmaceutical composition to be used for in vivo administration typically must be sterile. This may be accomplished by filtration through sterile filtration membranes. Where the composition is lyophilized, sterilization using these methods may be conducted either prior to, or following, lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of an C3b/C4b CR-like pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the C3b/C4b CR-like molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 $\mu$g/kg to up to about 100 mg/kg or more, depending on the factors mentioned above. In other embodiments, the dosage may range from 0.1 $\mu$g/kg up to about 100 mg/kg; or 1 $\mu$g/kg up to about 100 mg/kg; or 5 $\mu$g/kg up to about 100 mg/kg.

The frequency of dosing will depend upon the pharmacokinetic parameters of the C3b/C4b CR-like molecule in the formulation used. Typically, a clinician will administer the composition until a dosage is reached that achieves the desired effect. The composition may therefore be administered as a single dose, or as two or more doses (which may or may not contain the same amount of the desired molecule) over time, or as a continuous infusion via implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g. oral, injection by intravenous, intraperitoneal, intracerebral (intraparenchymal), intracerebroventricular, intramuscular, intraocular, intraarterial, intraportal, or intralesional routes, or by sustained release systems or implantation device. Where desired, the compositions may be administered by bolus injection or continuously by infusion, or by implantation device.

Alternatively or additionally, the composition may be administered locally via implantation of a membrane, sponge, or other appropriate material on to which the desired molecule has been absorbed or encapsulated. Where an implantation device is used, the device may be implanted into any suitable tissue or organ, and delivery of the desired molecule may be via diffusion, timed release bolus, or continuous administration.

In some cases, it may be desirable to use C3b/C4b CR-like pharmaceutical compositions in an ex vivo manner. In such instances, cells, tissues, or organs that have been removed from the patient are exposed to C3b/C4b CR-like pharmaceutical compositions after which the cells, tissues and/or organs are subsequently implanted back into the patient.

In other cases, an C3b/C4b CR-like polypeptide can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally silent C3b/C4b CR-like gene, or an under expressed gene, and thereby produce a cell which expresses therapeutically efficacious amounts of C3b/C4b CR-like polypeptides.

Homologous recombination is a technique originally developed for targeting genes to induce or correct mutations in transcriptionally active genes (Kucherlapati, *Prog. in Nucl. Acid Res. & Mol. Biol.,* 36:301, 1989). The basic technique was developed as a method for introducing specific mutations into specific regions of the mammalian genome (Thomas et al., *Cell,* 44:419–428, 1986; Thomas and Capecchi, *Cell,* 51:503–512, 1987; Doetschman et al.; *Proc. Natl. Acad. Sci.,* 85:8583–8587, 1988) or to correct specific mutations within defective genes (Doetschman et al., *Nature,* 330:576–578, 1987). Exemplary homologous recombination techniques are described in U.S. Pat. No. 5,272,071 (EP 9193051, EP Publication No. 505500; PCT/US90/07642, International Publication No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA which may interact with or control the expression of a C3b/C4b CR-like polypeptide, e.g., flanking sequences. For example, a promoter/enhancer element, a suppresser, or an exogenous transcription modulatory element is inserted in the genome of the intended host cell in proximity and orientation sufficient to influence the transcription of DNA encoding the desired C3b/C4b CR-like polypeptide. The control element controls a portion of the DNA present in the host cell genome. Thus, the expression of the desired C3b/

C4b CR-like polypeptide may be achieved not by transfection of DNA that encodes the C3b/C4b CR-like gene itself, but rather by the use of targeting DNA (containing regions of homology with the endogenous gene of interest) coupled with DNA regulatory segments that provide the endogenous gene sequence with recognizable signals for transcription of an C3b/C4b CR-like polypeptide.

In an exemplary method, the expression of a desired targeted gene in a cell (i.e., a desired endogenous cellular gene) is altered via homologous recombination into the cellular genome at a preselected site, by the introduction of DNA which includes at least a regulatory sequence, an exon and a splice donor site. These components are introduced into the chromosomal (genomic) DNA in such a manner that this, in effect, results in the production of a new transcription unit (in which the regulatory sequence, the exon and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, C3b/C4b CR-like polypeptide production from a cell's endogenous C3b/C4b CR-like gene involves first using homologous recombination to place a recombination sequence from a site-specific recombination system (e.g., Cre/loxP, FLP/FRT) (Sauer, *Current Opinion In Biotechnology*, 5:521–527, 1994; Sauer, *Methods In Enzymology*, 225:890–900, 1993) upstream (that is, 5' to) of the cell's endogenous genomic C3b/C4b CR-like polypeptide coding region. A plasmid containing a recombination site homologous to the site that was placed just upstream of the genomic C3b/C4b CR-like polypeptide coding region is introduced into the modified cell line along with the appropriate recombinase enzyme. This recombinase causes the plasmid to integrate, via the plasmid's recombination site, into the recombination site located just upstream of the genomic C3b/C4b CR-like polypeptide coding region in the cell line (Baubonis and Sauer, *Nucleic Acids Res.*, 21:2025–2029, 1993; O'Gorman et al., *Science*, 251:1351–1355, 1991). Any flanking sequences known to increase transcription (e.g., enhancer/promoter, intron, translational enhancer), if properly positioned in this plasmid, would integrate in such a manner as to create a new or modified transcriptional unit resulting in de novo or increased C3b/C4b CR-like polypeptide production from the cell's endogenous C3b/C4b CR-like gene.

A further method to use the cell line in which the site specific recombination sequence had been placed just upstream of the cell's endogenous genomic C3b/C4b CR-like polypeptide coding region is to use homologous recombination to introduce a second recombination site elsewhere in the cell line's genome. The appropriate recombinase enzyme is then introduced into the two-recombination-site cell line, causing a recombination event (deletion, inversion, translocation) (Sauer, *Current Opinion In Biotechnology*, supra, 1994; Sauer, *Methods In Enzymology*, supra, 1993) that would create a new or modified transcriptional unit resulting in de novo or increased C3b/C4b CR-like polypeptide production from the cell's endogenous C3b/C4b CR-like gene.

An additional approach for increasing, or causing, the expression of C3b/C4b CR-like polypeptide from a cell's endogenous C3b/C4b CR-like gene involves increasing, or causing, the expression of a gene or genes (e.g., transcription factors) and/or decreasing the expression of a gene or genes (e.g., transcriptional repressors) in a manner which results in de novo or increased C3b/C4b CR-like polypeptide production from the cell's endogenous C3b/C4b CR-like gene. This method includes the introduction of a non-naturally occurring polypeptide (e.g., a polypeptide comprising a site specific DNA binding domain fused to a transcriptional factor domain) into the cell such that de novo or increased C3b/C4b CR-like polypeptide production from the cell's endogenous C3b/C4b CR-like gene results.

The present invention further relates to DNA constructs useful in the method of altering expression of a target gene. In certain embodiments, the exemplary DNA constructs comprise: (a) one or more targeting sequences; (b) a regulatory sequence; (c) an exon; and (d) an unpaired splice-donor site. The targeting sequence in the DNA construct directs the integration of elements (a)–(d) into a target gene in a cell such that the elements (b)–(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)–(f) such that the elements of (b)–(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of C3b/C4b CR-like polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence(s) upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a C3b/C4b CR-like polypeptide, which nucleotides may be used as targeting sequences.

C3b/C4b CR-like polypeptide cell therapy, e.g., the implantation of cells producing C3b/C4b CR-like polypeptides, is also contemplated. This embodiment involves implanting cells capable of synthesizing and secreting a biologically active form of C3b/C4b CR-like polypeptide. Such C3b/C4b CR-like polypeptide-producing cells can be cells that are natural producers of C3b/C4b CR-like polypeptides or may be recombinant cells whose ability to produce C3b/C4b CR-like polypeptides has been augmented by transformation with a gene encoding the desired C3b/C4b CR-like polypeptide or with a gene augmenting the expression of C3b/C4b CR-like polypeptide. Such a modification may be accomplished by means of a vector suitable for delivering the gene as well as promoting its expression and secretion. In order to minimize a potential immunological reaction in patients being administered an C3b/C4b CR-like polypeptide, as may occur with the administration of a polypeptide of a foreign species, it is preferred that the natural cells producing C3b/C4b CR-like polypeptide be of human origin and produce human C3b/C4b CR-like polypeptide. Likewise, it is preferred that the recombinant cells producing C3b/C4b CR-like polypeptide be transformed with an expression vector containing a gene encoding a human C3b/C4b CR-like polypeptide.

Implanted cells may be encapsulated to avoid the infiltration of surrounding tissue. Human or non-human animal cells may be implanted in patients in biocompatible, semipermeable polymeric enclosures or membranes that allow the release of C3b/C4b CR-like polypeptide, but that prevent the destruction of the cells by the patient's immune system or by other detrimental factors from the surrounding tissue. Alternatively, the patient's own cells, transformed to produce C3b/C4b CR-like polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (WO95/05452; PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down regulation in vivo upon implantation into a mammalian host. The devices provide for the delivery of the molecules from living cells to specific sites within a recipient. In addition, see U.S. Pat. Nos. 4,892,538, 5,011,472, and 5,106,627. A system for encapsulating living cells is described in PCT Application no. PCT/US91/00157 of Aebischer et al. See also, PCT Application no. PCT/US91/00155 of Aebischer et al., Winn et al., *Exper. Neurol.*, 113:322–329 (1991), Aebischer et al., *Exper. Neurol.*, 111:269–275 (1991); and Tresco et al., ASAIO, 38:17–23 (1992).

In vivo and in vitro gene therapy delivery of C3b/C4b CR-like polypeptides is also envisioned. One example of a gene therapy technique is to use the C3b/C4b CR-like gene (either genomic DNA, cDNA, and/or synthetic DNA) encoding a C3b/C4b CR-like polypeptide which may be operably linked to a constitutive or inducible promoter to form a "gene therapy DNA construct". The promoter may be homologous or heterologous to the endogenous C3b/C4b CR-like gene, provided that it is active in the cell or tissue type into which the construct will be inserted. Other components of the gene therapy DNA construct may optionally include, DNA molecules designed for site-specific integration (e.g., endogenous sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (as, for example, for cell targeting), cell-specific internalization factors, and transcription factors to enhance expression by a vector as well as factors to enable vector manufacture.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the C3b/C4b CR-like gene in the target cell. Such elements are turned on in response to an appropriate effector. In this way, a therapeutic polypeptide can be expressed when desired. One conventional control means involves the use of small molecule dimerizers or rapalogs (as described in WO9641865 (PCT/US96/099486); WO9731898 (PCT/US97/03137) and WO9731899 (PCT/US95/03157) used to dimerize chimeric proteins which contain a small molecule-binding domain and a domain capable of initiating biological process, such as a DNA-binding protein or transcriptional activation protein. The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain which results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See, *Science* 287:816–817, and 826–830 (2000).

Other suitable control means or gene switches include, but are not limited to, the following systems. Mifepristone (RU486) is used as a progesterone antagonist. The binding of a modified progesterone receptor ligand-binding domain to the progesterone antagonist activates transcription by forming a dimer of two transcription factors which then pass into the nucleus to bind DNA. The ligand binding domain is modified to eliminate the ability of the receptor to bind to the natural ligand. The modified steroid hormone receptor system is further described in U.S. Pat. Nos. 5,364,791; WO9640911, and WO9710337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain/DNA-binding domain/ligand-binding domain to initiate transcription. The ecdysone system is further described in U.S. Pat. No. 5,514,578; WO9738117; WO9637609; and WO9303162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758; 5,650,298 and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding an C3b/C4b CR-like polypeptide into cells via local injection of an C3b/C4b CR-like nucleic acid molecule or by other appropriate viral or non-viral delivery vectors. Hefti, *Neurobiology*, 25:1418–1435 (1994). For example, a nucleic acid molecule encoding an C3b/C4b CR-like polypeptide may be contained in an adeno-associated virus (AAV) vector for delivery to the targeted cells (e.g., Johnson, International Publication No. WO95/34670; International Application No. PCT/US95/07178). The recombinant AAV genome typically contains AAV inverted terminal repeats flanking a DNA sequence encoding an C3b/C4b CR-like polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 involving adenoviral vectors; U.S. Pat. No. 5,672,510 involving retroviral vectors; and U.S. Pat. No. 5,635,399 involving retroviral vectors expressing cytokines.

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include the use of inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 involving electroporation techniques; WO96/40958 involving nuclear ligands; U.S. Pat. No. 5,679,559 describing a lipoprotein-containing system for gene delivery; U.S. Pat. No. 5,676,954 involving liposome carriers; U.S. Pat. No. 5,593,875 concerning methods for calcium phosphate transfection; and U.S. Pat. No. 4,945,050 wherein biologically active particles are propelled at cells at a speed whereby the particles penetrate the surface of the cells and become incorporated into the interior of the cells.

It is also contemplated that C3b/C4b CR-like gene therapy or cell therapy can further include the delivery of one or more additional polypeptide(s) in the same or a different cell(s). Such cell's may be separately introduced into the patient, or the cells may be contained in a single implantable device, such as the encapsulating membrane described above, or the cells may be separately modified by means of viral vectors.

A means to increase endogenous C3b/C4b CR-like polypeptide expression in a cell via gene therapy is to insert one or more enhancer elements into the C3b/C4b CR-like polypeptide promoter, where the enhancer element(s) can serve to increase transcriptional activity of the C3b/C4b CR-like gene. The enhancer element(s) used will be selected based on the tissue in which one desires to activate the gene (s); enhancer elements known to confer promoter activation in that tissue will be selected. For example, if a gene encoding a C3b/C4b CR-like polypeptide is to be "turned on" in T-cells, the lck promoter enhancer element may be used. Here, the functional portion of the transcriptional element to be added may be inserted into a fragment of DNA containing the C3b/C4b CR-like polypeptide promoter (and optionally, inserted into a vector and/or 5' and/or 3' flanking sequence(s), etc.) using standard cloning techniques. This construct, known as a "homologous recombination construct", can then be introduced into the desired cells either ex vivo or in vivo.

Gene therapy also can be used to decrease C3b/C4b CR-like polypeptide expression by modifying the nucleotide sequence of the endogenous promoter(s). Such modification is typically accomplished via homologous recombination methods. For example, a DNA molecule containing all or a portion of the promoter of the C3b/C4b CR-like gene(s) selected for inactivation can be engineered to remove and/or replace pieces of the promoter that regulate transcription. For example the TATA box and/or the binding site of a transcriptional activator of the promoter may be deleted using standard molecular biology techniques; such deletion can inhibit promoter activity thereby repressing the transcription of the corresponding C3b/C4b CR-like gene. The deletion of the TATA box or the transcription activator binding site in the promoter may be accomplished by generating a DNA construct comprising all or the relevant portion of the C3b/C4b CR-like polypeptide promoter(s) (from the same or a related species as the C3b/C4b CR-like gene(s) to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. The construct will typically contain at least about 500 bases of DNA that correspond to the native (endogenous) 5' and 3' DNA sequences adjacent to the promoter segment that has been modified. The construct may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Additional Uses of C3b/C4b CR-like Nucleic Acids and Polypeptides

Nucleic acid molecules of the present invention (including those that do not themselves encode biologically active polypeptides) may be used to map the locations of the C3b/C4b CR-like gene and related genes on chromosomes. Mapping may be done by techniques known in the art, such as PCR amplification and in situ hybridization.

C3b/C4b CR-like nucleic acid molecules (including those that do not themselves encode biologically active polypeptides), may be useful as hybridization probes in diagnostic assays to test, either qualitatively or quantitatively, for the presence of an C3b/C4b CR-like DNA or corresponding RNA in mammalian tissue or bodily fluid samples.

The C3b/C4b CR-like polypeptides may be used (simultaneously or sequentially) in combination with one or more cytokines, growth factors, antibiotics, anti-inflammatories, and/or chemotherapeutic agents as is appropriate for the indication being treated.

Other methods may also be employed where it is desirable to inhibit the activity of one or more C3b/C4b CR-like polypeptides. Such inhibition may be effected by nucleic acid molecules which are complementary to and hybridize to expression control sequences (triple helix formation) or to C3b/C4b CR-like mRNA. For example, antisense DNA or RNA molecules, which have a sequence that is complementary to at least a portion of the selected C3b/C4b CR-like gene(s) can be introduced into the cell. Anti-sense probes may be designed by available techniques using the sequence of C3b/C4b CR-like polypeptide disclosed herein. Typically, each such antisense molecule will be complementary to the start site (5' end) of each selected C3b/C4b CR-like gene. When the antisense molecule then hybridizes to the corresponding C3b/C4b CR-like mRNA, translation of this mRNA is prevented or reduced. Anti-sense inhibitors provide information relating to the decrease or absence of an C3b/C4b CR-like polypeptide in a cell or organism.

Alternatively, gene therapy may be employed to create a dominant-negative inhibitor of one or more C3b/C4b CR-like polypeptides. In this situation, the DNA encoding a mutant polypeptide of each selected C3b/C4b CR-like polypeptide can be prepared and introduced into the cells of a patient using either viral or non-viral methods as described herein. Each such mutant is typically designed to compete with endogenous polypeptide in its biological role.

In addition, an C3b/C4b CR-like polypeptide, whether biologically active or not, may be used as an immunogen, that is, the polypeptide contains at least one epitope to which antibodies may be raised. Selective binding agents that bind to an C3b/C4b CR-like polypeptide (as described herein) may be used for in vivo and in Vitro diagnostic purposes, including, but not limited to, use in labeled form to detect the presence of C3b/C4b CR-like polypeptide in a body fluid or cell sample. The antibodies may also be used to prevent, treat, or diagnose a number of diseases and disorders, including those recited herein. The antibodies may bind to an C3b/C4b CR-like polypeptide so as to diminish or block at least one activity characteristic of an C3b/C4b CR-like polypeptide, or may bind to a polypeptide to increase at least one activity characteristic of an C3b/C4b CR-like polypeptide (including by increasing the pharmacokinetics of the C3b/C4b CR-like polypeptide).

What is claimed:

1. An isolated nucleic acid comprising a nucleotide sequence selected from the group consisting of:
   (a) a nucleotide sequence set forth in SEQ ID NO: 1;
   (b) a nucleotide sequence encoding a polypeptide comprising an amino acid sequence as set forth in SEQ ID NO: 2; and
   (c) a nucleotide sequence fully complementary to (a) or (b).

2. A vector comprising the nucleic acid of claim 1.

3. A host cell comprising the vector of claim 2.

4. The host cell of claim 3 that is a eukaryotic cell.

5. The host cell of claim 3 that is a prokaryotic cell.

6. A process of producing a C3b/C4b complement receptor-like polypeptide comprising culturing the host cell of claim 3 under suitable conditions to express a C3b/C4b complement receptor-like polypeptide encoded by the nucleic acid.

7. The process of claim 6 wherein the vector further comprises a heterologous promoter operatively linked to the nucleotide sequence encoding the C3b/C4b complement receptor-like polypeptide.

8. A composition comprising a nucleic acid of claim 1 and a pharmaceutically acceptable formulation agent.

9. A composition of claim 8 wherein said nucleic acid is contained in a viral vector.

10. A viral vector comprising a nucleic acid of claim 1.

11. The process of claim 6 further comprising isolating the polypeptide from the culture.

12. An isolated nucleic acid comprising a nucleotide sequence selected from the group consisting of:
   (a) a nucleotide sequence encoding the polypeptide set forth in SEQ ID NO: 2;
   (b) a fragment of (a) wherein from 1 to 100 carboxy terminal codons have been deleted;
   (c) a fragment of (a) or (b) wherein from 1 to 100 amino terminal codons have been deleted;
   (d) a nucleotide sequence which hybridizes under stringent conditions to the full complement of any of (a)–(c) over the entire length of the sequence of (a)–(c) said stringent conditions comprising a final wash at 65° C. in 0.1×SSC and 0.1% SDS, wherein the nucleotide sequence encodes a polypeptide which has C3b/C4b complement receptor-like activity of the polypeptide set forth in SEQ ID NO: 2; and (e) a nucleotide sequence complementary to any of (a)–(d).

13. A vector comprising the nucleic arid of claim 12.
14. A host cell comprising the vector of claim 13.
15. The host cell of claim 14 that is a eukaryotic cell.
16. The host cell of claim 14 that is a prokaryotic cell.
17. A process of producing a C3b/C4b complement receptor-like polypeptide or fragment thereof comprising culturing the host cell of claim 14 under suitable conditions to express a C3b/C4b complement receptor-like polypeptide or fragment thereof encoded by the nucleic acid.

18. The process of claim 17 wherein the vector further comprises a heterologous promoter operatively linked to the nucleotide sequence encoding the C3b/C4b complement receptor-like polypeptide or fragment thereof.

19. The process of claim 17 further comprising isolating the polypeptide or fragment thereof from the culture.

* * * * *

UNITED STATES PATENT AND TRADEMARK OFFICE
CERTIFICATE OF CORRECTION

PATENT NO.    : 6,656,707 B2
DATED         : December 2, 2003
INVENTOR(S)   : Welcher et al.

It is certified that error appears in the above-identified patent and that said Letters Patent is hereby corrected as shown below:

Column 19,
Line 45, replace "DATA" with -- DNA --.

Column 22,
Line 4, replace "markets" with -- markers --.

Column 25,
Line 54, replace "DE/AE-dextran" with -- DEAE-dextran --.

Signed and Sealed this

Second Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,656,707 B2 Page 1 of 1
APPLICATION NO. : 09/911842
DATED : December 2, 2003
INVENTOR(S) : Andrew A. Welcher et al.

It is certified that error appears in the above-identified patent and that said Letters Patent is hereby corrected as shown below:

In the Specification:

Column 5, line 22, "C3b/C4b Complement Receptor (SEQ ID NO:2)" should be --C3b/C4b Complement Receptor (SEQ ID NO:5)--.

Column 5, line 23, "AGP-03144 (SEQ ID NO:5)" should be -- AGP-03144 (SEQ ID NO:2)--.

Signed and Sealed this

Fifth Day of December, 2006

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 10878
<212> TYPE: DNA
<213> ORGANISM: Homo sapiens

<400> SEQUENCE: 1
gattagcgcg atgtggcctc gcctggcctt ttgttgctgg ggtctggcgc tcgtttcggg      60
ctgggcgacc tttcagcaga tgtccccgtc gcgcaatttc agcttccgcc tcttccccga     120
gaccgcgccc ggggccccg ggagtatccc cgcgccgccc gctcctggcg acgaagcggc     180
ggggagcaga gtggagcggc tgggccaggc gttccggcga cgcgtgcggc tgctgcggga     240
gctcagcgag cgcctggagc ttgtcttcct ggtggatgat tcgtccagcg tgggcgaagt     300
caacttccgc agcgagctca tgttcgtccg caagctgctg tccgacttcc ccgtggtgcc     360
cacggccacg cgcgtggcca tcgtgacctt ctcgtccaag aactacgtgg tgccgcgcgt     420
cgattacatc tccacccgcc gcgcgcgcca gcacaagtgc gcgctgctcc tccaagagat     480
ccctgccatc tcctaccgag gtggcggcac ctacaccaag ggcgccttcc agcaagccgc     540
gcaaattctt cttcatgcta gagaaaactc aacaaaagtt gtatttctca tcactgatgg     600
atattccaat gggggagacc ctagaccaat tgcagcgtca ctgcgagatt caggagtgga     660
gatcttcact tttggcatat ggcaagggaa cattcgagag ctgaatgaca tggcttccac     720
cccaaaggag gagcactgtt acctgctaca cagttttgaa gaatttgagg ctttagctcg     780
ccgggcattg catgaagatc taccttctgg gagtttttatt caagatgata tggtccactg     840
ctcttatctt tgtgatgaag gcaaggactg ctgtgaccga atgggaagct gcaaatgtgg     900
gacacacaca ggccattttg agtgcatctg tgaaaagggg tattacggga aaggtctgca     960
gtatgaatgc acagcttgcc catcggggac atacaaacct gaaggctcac caggaggaat    1020
cagcagttgc attccatgtc ctgatgaaaa tcacacctct ccacctggaa gcacatcccc    1080
tgaagactgt gtctgcagag agggatacag ggcatctggc cagacctgtg aacttgtcca    1140
```

-continued

```
ctgccctgcc ctgaagcctc ccgaaaatgg ttactttatc caaaacactt gcaacaacca   1200
cttcaatgca gcctgtgggg tccgatgtca ccctggattt gatcttgtgg gaagcagcat   1260
catcttatgt ctacccaatg gtttgtggtc cggttcagag agctactgca gagtaagaac   1320
atgtcctcat ctccgccagc cgaaacatgg ccacatcagc tgttctacaa gggaaatgtt   1380
atataagaca acatgtttgg ttgcctgtga tgaagggtac agactagaag gcagtgataa   1440
gcttacttgt caaggaaaca gccagtggga tgggccagaa ccccggtgtg tggagcgcca   1500
ctgttccacc tttcagatgc ccaaagatat catcatatcc ccccacaact gtggcaagca   1560
gccagccaaa tttgggacga tctgctatgt aagttgccgc caagggttca ttttatctgg   1620
agtcaaagaa atgctgagat gtaccacttc tggaaaatgg aatgtcggag ttcaggcagc   1680
tgtgtgtaaa gacgtggagg ctcctcaaat caactgtcct aaggacatag aggctaagac   1740
tctggaacag caagattctg ccaatgttac ctggcagatt ccaacagcta agacaactc   1800 tggtgaaaag gtgtcagtcc acgttcatcc agctttcacc ccaccttacc ttttcccagt   1860
tggagatgtt gctatcgtat acacggcaac tgacctatcc ggcaaccagg ccagctgcat   1920
tttccatatc aaggttattg atgcagaacc acctgtcata gactggtgca gatctccacc   1980
tcccgtccag gtctcggaga aggtacatgc cgcaagctgg gatgagcctc agttctcaga   2040
caactcaggg gctgaattgg tcattaccag aagtcataca caaggagacc ttttccctca   2100
aggggagact atagtacagt atacagccac tgacccctca ggcaataaca ggacatgtga   2160
tatccatatt gtcataaaag gttctccctg tgaaattcca ttcacacctg taaatgggga   2220
ttttatatgc actccagata atactggagt caactgtaca ttaacttgct ggagggcta   2280 tgatttcaca gaagggtcta ctgacaagta ttattgtgct tatgaagatg gcgtctggaa   2340
accaacatat accactgaat ggccagactg tgccaaaaaa cgttttgcta ccacgggtt   2400 caagtccttt gagatgttct acaaagcagc tcgttgtgat gacacagatc tgatgaagaa   2460
gttttctgaa gcatttgaga cgaccctggg aaaaatggtc ccatcatttt gtagtgatgc   2520
agaggacatt gactgcagac tggaggagaa cctgaccaaa aaatattgcc tagaatataa   2580
ttatgactat gaaaatggct ttgcaattgg accaggtggc tggggtgcag ctaataggct   2640
ggattactct tacgatgact cctggacac tgtgcaagaa acagccacaa gcatcggcaa   2700
tgccaagtcc tcacggatta aaagaagtgc cccattatct gactataaaa ttaagttaat   2760
ttttaacatc acagctagtg tgccattacc cgatgaaaga aatgataccc ttgaatggga   2820
aaatcagcaa cgactccttc agacattgga aactatcaca aataaactga aaaggactct   2880
caacaaagac cccatgtatt cctttcagct tgcatcagaa atacttatag ccgacagcaa   2940
ttcattagaa acaaaaaagg cttccccctt ctgcagacca ggctcagtgc tgagagggcg   3000
tatgtgtgtc aattgcccctt tgggaaccta ttataatctg gaacatttca cctgtgaaag   3060
ctgccggatc ggatcctatc aagatgaaga agggcaactt gagtgcaagc tttgcccctc   3120
tgggatgtac acggaatata tccattcaag aaacatctct gattgtaaag ctcagtgtaa   3180
acaaggcacc tactcataca gtggacttga gacttgtgaa tcgtgtccac tgggcactta   3240
tcagccaaaa tttggttccc ggagctgcct tcgtgtccag aaaacacct caactgtgaa   3300 aagaggagcc gtgaacattt ctgcatgtgg agttccttgt ccagaaggaa aattctcgcg   3360
ttctgggtta atgccctgtc acccatgtcc tcgtgactat taccaaccta tgcaggaa   3420 ggccttctgc ctggcctgtc cctttatgg aactacccca ttcgctggtt ccagatccat   3480
```

-continued

| | |
|---|---|
| cacagaatgt tcaagtttta gttcaacttt ctcagcggca gaggaaagtg tggtgccccc | 3540 |
| tgcctctctt ggacatatta aaagaggca tgaaatcagc agtcaggttt tccatgaatg | 3600 |
| cttcttttaac ccttgccaca atagtggaac ctgccagcaa cttgggcgtg ttatgtttg | 3660 |
| tctctgtcca cttggatata caggcttaaa gtgtgaaaca gacatcgatg agtgcagccc | 3720 |
| actgccttgc ctcaacaatg gagtttgtaa agacctagtt gggggaattca tttgtgagtg | 3780 |
| cccatcaggt tacacaggtc agcggtgtga agaaaatata aatgagtgta gctccagtcc | 3840 |
| ttgtttaaat aaaggaatct gtgttgatgg tgtggctggc tatcgttgca catgtgtgaa | 3900 |
| aggatttgta ggcctgcatt gtgaaacaga agtcaatgaa tgccagtcaa acccatgctt | 3960 |
| aaataatgca gtctgtgaag accaggttgg gggattcttg tgcaaatgcc cacctggatt | 4020 |
| tttgggtacc cgatgtggaa agaacgtcga tgagtgtctc agtcagccat gcaaaaatgg | 4080 |
| agctacctgt aaagacggtg ccaatagctt cagatgcctg tgtgcagctg gcttcacagg | 4140 |
| atcacactgt gaattgaaca tcaatgaatg tcagtctaat ccatgtagaa atcaggccac | 4200 |
| ctgtgtggat gaattaaatt catacagttg taaatgtcag ccaggatttt caggcaaaag | 4260 |
| gtgtgaaaca gaacagtcta caggctttaa cctggatttt gaagtttctg gcatctatgg | 4320 |
| atatgtcatg ctagatggca tgctcccatc tctccatgct ctaacctgta ccttctggat | 4380 |
| gaaatcctct gacgacatga actatggaac accaatctcc tatgcagttg ataacggcag | 4440 |
| cgacaatacc ttgctcctga ctgattataa cggctgggtt cttttatgtga atggcaggga | 4500 |
| aaagataaca aactgtccct cggtgaatga tggcagatgg catcatattg caatcacttg | 4560 |
| gacaagtgcc aatggcatct ggaaagtcta tatcgatggg aaattatctg acggtggtgc | 4620 |
| tggcctctct gttggtttgc ccatacctgg tggtggtgcg ttagttctgg ggcaagagca | 4680 |
| agacaaaaaa ggagagggat tcagcccagc tgagtctttt gtgggctcca taagccagct | 4740 |
| caacctctgg gactatgtcc tgtctccaca gcaggtgaag tcactggcta cctcctgccc | 4800 |
| agaggaactc agtaaaggaa acgtgttagc atggcctgat tccttgtcag aattgtggg | 4860 |
| gaaagtgaag atcgattcta agagcatatt ttgttctgat tgcccacgct taggagggtc | 4920 |
| agtgcctcat ctgagaactg catctgaaga tttaaagcca ggttccaaag tcaatctgtt | 4980 |
| ctgtgatcca ggcttccagc tggtcgggaa ccctgtgcag tactgtctga atcaaggaca | 5040 |
| gtggacacaa ccacttcctc actgtgaacg cattagctgt ggggtgccac ctcctttgga | 5100 |
| gaatggcttc cattcagccg atgacttcta tgctggcagc acagtaacct accagtgcaa | 5160 |
| caatggctac tatctattgg gtgactcaag gatgttctgt acagataatg ggagctggaa | 5220 |
| cggcgtttca ccatcctgcc ttgatgtcga tgagtgtgca gttggatcag attgtagtga | 5280 |
| gcatgcttct tgcctgaacg tagatggatc ctacatatgt tcatgtgtcc caccgtacac | 5340 |
| aggagatggg aaaaactgtg cagaacctat aaaatgtaag gctccaggaa atccggaaaa | 5400 |
| tggccactcc tcaggtgaga tttatacagt aggtgccgaa gtcacatttt cgtgtcagga | 5460 |
| aggataccag ttgatgggag taaccaaaat cacatgtttg gagtctggag aatggaatca | 5520 |
| tctaatacca tattgtaaag ctgtttcatg tggtaaaccg gctattccag aaaatggttg | 5580 |
| cattgaggag ttagcattta cttttggcag caaagtgaca tataggtgta ataaggata | 5640 |
| tactctggcc ggtgataaag aatcatcctg tcttgctaac agttcttgga gtcattcccc | 5700 |
| tcctgtgtgt gaaccagtga agtgttctag tccggaaaat ataaataatg gaaaatatat | 5760 |
| tttgagtggg cttacctacc tttctactgc atcatattca tgcgatacag gatacagctt | 5820 |
| acagggccct tccattattg aatgcacggc ttctggcatc tgggacagag cgccacctgc | 5880 |

```
ctgtcacctc gtcttctgtg gagaaccacc tgccatcaaa gatgctgtca ttacggggaa    5940
taacttcact ttcaggaaca ccgtcactta cacttgcaaa gaaggctata ctcttgctgg    6000
tcttgacacc attgaatgcc tggccgacgg caagtggagt agaagtgacc agcagtgcct    6060
ggctgtctcc tgtgatgagc cacccattgt ggaccacgcc tctccagaga ctgcccatcg    6120 gctcttttgga gacattgcat tctactactg ctctgatggt tacagcctag cagacaattc    6180
ccagcttctc tgcaatgccc agggcaagtg ggtaccccca gaaggtcaag acatgccccg    6240
ttgtatagct catttctgtg aaaaacctcc atcggtttcc tatagcatct tggaatctgt    6300
gagcaaagca aaatttgcag ctggctcagt tgtgagcttt aaatgcatgg aaggctttgt    6360
actgaacacc tcagcaaaga ttgaatgtat gagaggtggg cagtggaacc cttcccccat    6420
gtccatccag tgcatccctg tgcggtgtgg agagccacca agcatcatga atggctatgc    6480
aagtggatca aactacagtt ttggagccat ggtggcttac agctgcaaca aggggttcta    6540
catcaagggg gaaaagaaga gcacctgcga agccacaggg cagtggagta gtcctatacc    6600
gacgtgccac ccgtatcttt gtggtgaacc acctaaggtt gagaatggct ttctggagca    6660
tacaactggc aggatctttg agagtgaagt gaggtatcag tgtaacccgg gctataagtc    6720
agtcggaagt cctgtatttg tctgccaagc caatcgccac tggcacagtg aatcccctct    6780
gatgtgtgtt cctctcgact gtggaaaacc tcccccgatc cagaatggct tcatgaaagg    6840
agaaaacttt gaagtagggt ccaaggttca gttttttctgt aatgagggtt atgagcttgt    6900
tggtgacagt tcttggacat gtcagaaatc tggcaaatgg aataagaagt caaatccaaa    6960
gtgcatgcct gccaagtgcc cagagccgcc cctcttggaa aaccagctag tattaaagga    7020
gttgaccacc gaggtaggag ttgtgacatt ttcctgtaaa gaagggcatg tcctgcaagg    7080
cccctctgtc ctgaaatgct tgccatccca gcaatggaat gactctttcc ctgtttgtaa    7140
gattgttctt tgtaccccac ctcccctaat ttcctttggt gtcccattc cttcttctgc    7200 tcttcatttt ggaagtactg tcaagtattc ttgtgtaggt gggttttcc taagaggaaa    7260 ttctaccacc ctctgccaac ctgatggcac ctggagctct ccactgccag aatgtgttcc    7320
agtagaatgt cccccaacctg aggaaatccc caatggaatc attgatgtgc aaggccttgc    7380
ctatctcagc acagctctct ataccgcaa gccaggcttt gaattggtgg gaaatactac    7440
caccctttgt ggagaaaatg gtcactggct tggaggaaaa ccaacatgta aagccattga    7500
gtgcctgaaa cccaaggaga ttttgaatgg caaattctct tacacggacc tacactatgg    7560
acagaccgtt acctactctt gcaaccgagg cttccggctc gaaggtccca gtgccttgac    7620
ctgtttagag acaggtgatt gggatgtaga tgccccatct tgcaatgcca tccactgtga    7680
ttccccacaa cccattgaaa atggttttgt agaaggtgca gattacagct atggtgccat    7740
aatcatctac agttgcttcc ctgggtttca ggtggctggt catgccatgc agacctgtga    7800
agagtcagga tggtcaagtt ccatcccaac atgtatgcca atagactgtg gcctccctcc    7860
tcatatagat tttggagact gtactaaact caaagatgac cagggatatt ttgagcaaga    7920
agacgacatg atggaagttc catatgtgac tcctcaccct ccttatcatt gggagcagt    7980 ggctaaaacc tggaaaata caaggagtc tcctgctaca cattcatcaa actttctgta    8040
tggtaccatg gtttcataca cctgtaatcc aggatatgaa cttctgggga accctgtgct    8100
gatctgccag gaagatggaa cttggaatgg cagtgcacca tcctgcattt caattgaatg    8160
tgacttgcct actgctcctg aaaatggctt tttgcgtttt acagagacta gcatgggaag    8220
```

-continued

| | |
|---|---|
| tgctgtgcag tatagctgta aacctggaca cattctagtg ggctctgact taaggctttg | 8280 |
| tctagagaat agaaagtgga gtggtgcctc cccacgctgt gaagccattt catgcaaaaa | 8340 |
| gccaaatcca gtcatgaatg gatccatcaa aggaagcaac tacacatacc tgagcacgtt | 8400 |
| gtactatgag tgtgaccccg gatatgtgct gaatggcact gagaggagaa catgccagga | 8460 |
| tgacaaaaac tgggatgagg atgagcccat ttgcattcct gtggactgca gttcaccccc | 8520 |
| agtctcagcc aatggccagg tgagaggaga cgagtacaca ttccaaaaag agattgaata | 8580 |
| cacttgcaat gaagggttct tgcttgaggg agccaggagt cgggtttgtc ttgccaatgg | 8640 |
| aagttggagt ggagccactc ccgactgtgt gcctgtcaga tgtgccaccc cgccacaact | 8700 |
| ggccaatggg gtgacggaag gcctggacta tggcttcatg aaggaagtaa cattccactg | 8760 |
| tcatgagggc tacatcttgc acggtgctcc aaaactcacc tgtcagtcag atggcaactg | 8820 |
| ggatgcagag attcctctct gtaaaccagt caactgtgga cctcctgaag atcttgccca | 8880 |
| tggtttccct aatggttttt cctttattca tgggggccat atacagtatc agtgctttcc | 8940 |
| tggttataag ctccatggaa attcatcaag aaggtgcctc tccaatggct cctggagtgg | 9000 |
| cagctcacct tcctgcctgc cttgcagatg ttccacacca gtaattgaat atggaactgt | 9060 |
| caatgggaca gattttgact gtggaaaggc agcccggatt cagtgcttca aaggcttcaa | 9120 |
| gctcctagga ctttctgaaa tcacctgtga agccgatggc cagtggagct ctgggttccc | 9180 |
| ccactgtgaa cacacttctt gtggttctct tccaatgata ccaaatgcgt tcatcagtga | 9240 |
| gaccagctct tggaaggaaa atgtgataac ttacagctgc aggtctggat atgtcataca | 9300 |
| aggcagttca gatctgattt gtacagagaa aggggtatgg agccagcctt atccagtctg | 9360 |
| tgagcccttg tcctgtgggt ccccaccgtc tgtcgccaat gcagtggcaa ctggagaggc | 9420 |
| acacacctat gaaagtgaag tgaaactcag atgtctggaa ggttatacga tggatacaga | 9480 |
| tacagataca ttcacctgtc agaaagatgg tcgctggttc cctgagagaa tctcctgcag | 9540 |
| tcctaaaaaa tgtcctctcc cggaaaacat aacacatata cttgttcatg gggacgattt | 9600 |
| cagtgtgaat aggcaagttt ctgtgtcatg tgcagaaggg tatacctttg agggagttaa | 9660 |
| catatcagta tgtcagcttg atggaacctg ggagccacca ttctccgatg aatcttgcag | 9720 |
| tccagtttct tgtgggaaac ctgaaagtcc agaaatggaa tttgtggttg gcagtaaata | 9780 |
| ccctttgaa agcacaatta tttatcagtg tgagcctggc tatgaactag ggggaacag | 9840 |
| ggaacgcgtc tgccaggaga acagacagtg gagtggaggg gtggcaatat gcaaagagac | 9900 |
| caggtgtgaa actccacttg aatttctcaa tgggaaagct gacattgaaa acaggacgac | 9960 |
| tggacccaac gtggtatatt cctgcaacag aggctacagt cttgaagggc catctgaggc | 10020 |
| acactgcaca gaaaatggaa cctggagcca cccagtccct ctctgcaaac caaatccatg | 10080 |
| ccctgttcct tttgtgattc ccgagaatgc tctgctgtct gaaaaggagt tttatgttga | 10140 |
| tcagaatgtg tccatcaaat gtagggaagg ttttctgctg caggccacg gcatcattac | 10200 |
| ctgcaacccc gacgagacgt ggacacagac aagcgccaaa tgtgaaaaaa tctcatgtgg | 10260 |
| tccaccagct cacgtagaaa atgcaattgc tcgaggcgta cattatcaat atggagacat | 10320 |
| gatcacctac tcatgttaca gtggatacat gttggagggt tcctgagga gtgtttgttt | 10380 |
| agaaaatgga acatggacat cacctcctat ttgcagagct gtctgtcgat ttccatgtca | 10440 |
| gaatgggggc atctgccaac gcccaaatgc ttgttcctgt ccagagggct ggatggggcg | 10500 |
| cctctgtgaa gaaccaatct gcattcttcc ctgtctgaac ggaggtcgct gtgtggcccc | 10560 |
| ttaccagtgt gactgcccgc ctggctggac ggggtctcgc tgtcatacag ctgtttgcca | 10620 |

```
gtctccctgc ttaaatggtg gaaaatgtgt aagaccaaac cgatgtcact gtctttcttc   10680
ttggacggga cataactgtt ccaggaaaag gaggactggg ttttaaccac tgcacgacca   10740
tctggctctc ccaaaagcag gatcatctct cctcggtagt gcctgggcat cctggaactt   10800
atgcaaagaa agtccaacat ggtgctgggt cttgtttagt aaacttgtta cttggggtga   10860
aaaaaaaaaa aaaaaaaa                                                 10878
```

<210> SEQ ID NO 2
<211> LENGTH: 3571
<212> TYPE: PRT
<213> ORGANISM: Homo sapiens
<400> SEQUENCE: 2

```
Met Trp Pro Arg Leu Ala Phe Cys Cys Trp Gly Leu Ala Leu Val Ser
1               5                  10                  15

Gly Trp Ala Thr Phe Gln Gln Met Ser Pro Ser Arg Asn Phe Ser Phe
            20                  25                  30

Arg Leu Phe Pro Glu Thr Ala Pro Gly Ala Pro Gly Ser Ile Pro Ala
        35                  40                  45

Pro Pro Ala Pro Gly Asp Glu Ala Ala Gly Ser Arg Val Glu Arg Leu
    50                  55                  60

Gly Gln Ala Phe Arg Arg Val Arg Leu Leu Arg Glu Leu Ser Glu
65                  70                  75                  80

Arg Leu Glu Leu Val Phe Leu Val Asp Ser Ser Val Gly
                85                  90                  95

Val Asn Phe Arg Ser Glu Leu Met Phe Val Arg Lys Leu Leu Ser Asp
                100                 105                 110

Phe Pro Val Val Pro Thr Ala Thr Arg Val Ala Ile Val Thr Phe Ser
            115                 120                 125

Ser Lys Asn Tyr Val Val Pro Arg Val Asp Tyr Ile Ser Thr Arg Arg
130                 135                 140

Ala Arg Gln His Lys Cys Ala Leu Leu Leu Gln Glu Ile Pro Ala Ile
145                 150                 155                 160

Ser Tyr Arg Gly Gly Gly Thr Tyr Thr Lys Gly Ala Phe Gln Gln Ala
                165                 170                 175

Ala Gln Ile Leu Leu His Ala Arg Glu Asn Ser Thr Lys Val Val Phe
            180                 185                 190

Leu Ile Thr Asp Gly Tyr Ser Asn Gly Gly Asp Pro Arg Pro Ile Ala
        195                 200                 205

Ala Ser Leu Arg Asp Ser Gly Val Glu Ile Phe Thr Phe Gly Ile Trp
    210                 215                 220

Gln Gly Asn Ile Arg Glu Leu Asn Asp Met Ala Ser Thr Pro Lys Glu
225                 230                 235                 240

Glu His Cys Tyr Leu Leu His Ser Phe Glu Glu Phe Glu Ala Leu Ala
                245                 250                 255

Arg Arg Ala Leu His Glu Asp Leu Pro Ser Gly Ser Phe Ile Gln Asp
            260                 265                 270

Asp Met Val His Cys Ser Tyr Leu Cys Asp Glu Gly Lys Asp Cys Cys
        275                 280                 285

Asp Arg Met Gly Ser Cys Lys Cys Gly Thr His Thr His Gly His Phe Glu
    290                 295                 300

Cys Ile Cys Glu Lys Gly Tyr Tyr Gly Lys Gly Leu Gln Tyr Glu Cys
305                 310                 315                 320
```

-continued

Thr Ala Cys Pro Ser Gly Thr Tyr Lys Pro Glu Gly Ser Pro Gly Gly
                    325                 330                 335

Ile Ser Ser Cys Ile Pro Cys Pro Asp Glu Asn His Thr Ser Pro Pro
                340                 345                 350

Gly Ser Thr Ser Pro Glu Asp Cys Val Cys Arg Glu Gly Tyr Arg Ala
                355                 360                 365

Ser Gly Gln Thr Cys Glu Leu Val His Cys Pro Ala Leu Lys Pro Pro
            370                 375                 380

Glu Asn Gly Tyr Phe Ile Gln Asn Thr Cys Asn Asn His Phe Asn Ala
385                 390                 395                 400

Ala Cys Gly Val Arg Cys His Pro Gly Phe Asp Leu Val Gly Ser Ser
                405                 410                 415

Ile Ile Leu Cys Leu Pro Asn Gly Leu Trp Ser Gly Ser Glu Ser Tyr
                420                 425                 430

Cys Arg Val Arg Thr Cys Pro His Leu Arg Gln Pro Lys His Gly His
            435                 440                 445

Ile Ser Cys Ser Thr Arg Glu Met Leu Tyr Lys Thr Thr Cys Leu Val
450                 455                 460

Ala Cys Asp Glu Gly Tyr Arg Leu Glu Gly Ser Asp Lys Leu Thr Cys
465                 470                 475                 480

Gln Gly Asn Ser Gln Trp Asp Gly Pro Glu Pro Arg Cys Val Glu Arg
                485                 490                 495

His Cys Ser Thr Phe Gln Met Pro Lys Asp Ile Ile Ser Pro His
            500                 505                 510

Asn Cys Gly Lys Gln Pro Ala Lys Phe Gly Thr Ile Cys Tyr Val Ser
                515                 520                 525

Cys Arg Gln Gly Phe Ile Leu Ser Gly Val Lys Glu Met Leu Arg Cys
            530                 535                 540

Thr Thr Ser Gly Lys Trp Asn Val Gly Val Gln Ala Ala Val Cys Lys
545                 550                 555                 560

Asp Val Glu Ala Pro Gln Ile Asn Cys Pro Lys Asp Ile Glu Ala Lys
                565                 570                 575

Thr Leu Glu Gln Gln Asp Ser Ala Asn Val Thr Trp Gln Ile Pro Thr
            580                 585                 590

Ala Lys Asp Asn Ser Gly Glu Lys Val Ser Val His Val His Pro Ala
            595                 600                 605

Phe Thr Pro Pro Tyr Leu Phe Pro Val Gly Asp Val Ala Ile Val Tyr
            610                 615                 620

Thr Ala Thr Asp Leu Ser Gly Asn Gln Ala Ser Cys Ile Phe His Ile
625                 630                 635                 640

Lys Val Ile Asp Ala Glu Pro Pro Val Ile Asp Trp Cys Arg Ser Pro
                645                 650                 655

Pro Pro Val Gln Val Ser Glu Lys Val His Ala Ala Ser Trp Asp Glu
                660                 665                 670

Pro Gln Phe Ser Asp Asn Ser Gly Ala Glu Leu Val Ile Thr Arg Ser
            675                 680                 685

His Thr Gln Gly Asp Leu Phe Pro Gln Gly Glu Thr Ile Val Gln Tyr
            690                 695                 700

Thr Ala Thr Asp Pro Ser Gly Asn Asn Arg Thr Cys Asp Ile His Ile
705                 710                 715                 720

Val Ile Lys Gly Ser Pro Cys Glu Ile Pro Phe Thr Pro Val Asn Gly
                725                 730                 735

Asp Phe Ile Cys Thr Pro Asp Asn Thr Gly Val Asn Cys Thr Leu Thr

-continued

```
            740                 745                 750
Cys Leu Glu Gly Tyr Asp Phe Thr Glu Gly Ser Thr Asp Lys Tyr Tyr
                755                 760                 765

Cys Ala Tyr Glu Asp Gly Val Trp Lys Pro Thr Tyr Thr Thr Glu Trp
        770                 775                 780

Pro Asp Cys Ala Lys Lys Arg Phe Ala Asn His Gly Phe Lys Ser Phe
785                 790                 795                 800

Glu Met Phe Tyr Lys Ala Ala Arg Cys Asp Asp Thr Asp Leu Met Lys
                805                 810                 815

Lys Phe Ser Glu Ala Phe Glu Thr Thr Leu Gly Lys Met Val Pro Ser
                820                 825                 830

Phe Cys Ser Asp Ala Glu Asp Ile Asp Cys Arg Leu Glu Glu Asn Leu
                835                 840                 845

Thr Lys Lys Tyr Cys Leu Glu Tyr Asn Tyr Asp Tyr Glu Asn Gly Phe
            850                 855                 860

Ala Ile Gly Pro Gly Gly Trp Gly Ala Ala Asn Arg Leu Asp Tyr Ser
865                 870                 875                 880

Tyr Asp Asp Phe Leu Asp Thr Val Gln Glu Thr Ala Thr Ser Ile Gly
                885                 890                 895

Asn Ala Lys Ser Ser Arg Ile Lys Arg Ser Ala Pro Leu Ser Asp Tyr
            900                 905                 910

Lys Ile Lys Leu Ile Phe Asn Ile Thr Ala Ser Val Pro Leu Pro Asp
            915                 920                 925

Glu Arg Asn Asp Thr Leu Glu Trp Glu Asn Gln Gln Arg Leu Leu Gln
        930                 935                 940

Thr Leu Glu Thr Ile Thr Asn Lys Leu Lys Arg Thr Leu Asn Lys Asp
945                 950                 955                 960

Pro Met Tyr Ser Phe Gln Leu Ala Ser Glu Ile Leu Ile Ala Asp Ser
                965                 970                 975

Asn Ser Leu Glu Thr Lys Lys Ala Ser Pro Phe Cys Arg Pro Gly Ser
            980                 985                 990

Val Leu Arg Gly Arg Met Cys Val  Asn Cys Pro Leu Gly  Thr Tyr Tyr
            995                 1000                1005

Asn Leu  Glu His Phe Thr Cys  Glu Ser Cys Arg Ile  Gly Ser Tyr
    1010                1015                1020

Gln Asp  Glu Glu Gly Gln Leu  Glu Cys Lys Leu Cys  Pro Ser Gly
    1025                1030                1035

Met Tyr  Thr Glu Tyr Ile His  Ser Arg Asn Ile Ser  Asp Cys Lys
    1040                1045                1050

Ala Gln  Cys Lys Gln Gly Thr  Tyr Ser Tyr Ser Gly  Leu Glu Thr
    1055                1060                1065

Cys Glu  Ser Cys Pro Leu Gly  Thr Tyr Gln Pro Lys  Phe Gly Ser
    1070                1075                1080

Arg Ser  Cys Leu Ser Cys Pro  Glu Asn Thr Ser Thr  Val Lys Arg
    1085                1090                1095

Gly Ala  Val Asn Ile Ser Ala  Cys Gly Val Pro Cys  Pro Glu Gly
    1100                1105                1110

Lys Phe  Ser Arg Ser Gly Leu  Met Pro Cys His Pro  Cys Pro Arg
    1115                1120                1125

Asp Tyr  Tyr Gln Pro Asn Ala  Gly Lys Ala Phe Cys  Leu Ala Cys
    1130                1135                1140

Pro Phe  Tyr Gly Thr Thr Pro  Phe Ala Gly Ser Arg  Ser Ile Thr
    1145                1150                1155
```

```
Glu Cys Ser Ser Phe Ser Ser Thr Phe Ser Ala Ala Glu Glu Ser
    1160                1165                1170

Val Val Pro Pro Ala Ser Leu Gly His Ile Lys Lys Arg His Glu
    1175                1180                1185

Ile Ser Ser Gln Val Phe His Glu Cys Phe Phe Asn Pro Cys His
    1190                1195                1200

Asn Ser Gly Thr Cys Gln Gln Leu Gly Arg Gly Tyr Val Cys Leu
    1205                1210                1215

Cys Pro Leu Gly Tyr Thr Gly Leu Lys Cys Glu Thr Asp Ile Asp
    1220                1225                1230

Glu Cys Ser Pro Leu Pro Cys Leu Asn Asn Gly Val Cys Lys Asp
    1235                1240                1245

Leu Val Gly Glu Phe Ile Cys Glu Cys Pro Ser Gly Tyr Thr Gly
    1250                1255                1260

Gln Arg Cys Glu Glu Asn Ile Asn Glu Cys Ser Ser Ser Pro Cys
    1265                1270                1275

Leu Asn Lys Gly Ile Cys Val Asp Gly Val Ala Gly Tyr Arg Cys
    1280                1285                1290

Thr Cys Val Lys Gly Phe Val Gly Leu His Cys Glu Thr Glu Val
    1295                1300                1305

Asn Glu Cys Gln Ser Asn Pro Cys Leu Asn Asn Ala Val Cys Glu
    1310                1315                1320

Asp Gln Val Gly Gly Phe Leu Cys Lys Cys Pro Pro Gly Phe Leu
    1325                1330                1335

Gly Thr Arg Cys Gly Lys Asn Val Asp Glu Cys Leu Ser Gln Pro
    1340                1345                1350

Cys Lys Asn Gly Ala Thr Cys Lys Asp Gly Ala Asn Ser Phe Arg
    1355                1360                1365

Cys Leu Cys Ala Ala Gly Phe Thr Gly Ser His Cys Glu Leu Asn
    1370                1375                1380

Ile Asn Glu Cys Gln Ser Asn Pro Cys Arg Asn Gln Ala Thr Cys
    1385                1390                1395

Val Asp Glu Leu Asn Ser Tyr Ser Cys Lys Cys Gln Pro Gly Phe
    1400                1405                1410

Ser Gly Lys Arg Cys Glu Thr Glu Gln Ser Thr Gly Phe Asn Leu
    1415                1420                1425

Asp Phe Glu Val Ser Gly Ile Tyr Gly Tyr Val Met Leu Asp Gly
    1430                1435                1440

Met Leu Pro Ser Leu His Ala Leu Thr Cys Thr Phe Trp Met Lys
    1445                1450                1455

Ser Ser Asp Asp Met Asn Tyr Gly Thr Pro Ile Ser Tyr Ala Val
    1460                1465                1470

Asp Asn Gly Ser Asp Asn Thr Leu Leu Leu Thr Asp Tyr Asn Gly
    1475                1480                1485

Trp Val Leu Tyr Val Asn Gly Arg Glu Lys Ile Thr Asn Cys Pro
    1490                1495                1500

Ser Val Asn Asp Gly Arg Trp His His Ile Ala Ile Thr Trp Thr
    1505                1510                1515

Ser Ala Asn Gly Ile Trp Lys Val Tyr Ile Asp Gly Lys Leu Ser
    1520                1525                1530

Asp Gly Gly Ala Gly Leu Ser Val Gly Leu Pro Ile Pro Gly Gly
    1535                1540                1545
```

-continued

```
Gly Ala Leu Val Leu Gly Gln Glu Gln Asp Lys Lys Gly Glu Gly
    1550                1555                1560

Phe Ser Pro Ala Glu Ser Phe Val Gly Ser Ile Ser Gln Leu Asn
    1565                1570                1575

Leu Trp Asp Tyr Val Leu Ser Pro Gln Val Lys Ser Leu Ala
    1580                1585                1590

Thr Ser Cys Pro Glu Glu Leu Ser Lys Gly Asn Val Leu Ala Trp
    1595                1600                1605

Pro Asp Phe Leu Ser Gly Ile Val Gly Lys Val Lys Ile Asp Ser
    1610                1615                1620

Lys Ser Ile Phe Cys Ser Asp Cys Pro Arg Leu Gly Gly Ser Val
    1625                1630                1635

Pro His Leu Arg Thr Ala Ser Glu Asp Leu Lys Pro Gly Ser Lys
    1640                1645                1650

Val Asn Leu Phe Cys Asp Pro Gly Phe Gln Leu Val Gly Asn Pro
    1655                1660                1665

Val Gln Tyr Cys Leu Asn Gln Gly Gln Trp Thr Gln Pro Leu Pro
    1670                1675                1680

His Cys Glu Arg Ile Ser Cys Gly Val Pro Pro Leu Glu Asn
    1685                1690                1695

Gly Phe His Ser Ala Asp Asp Phe Tyr Ala Gly Ser Thr Val Thr
    1700                1705                1710

Tyr Gln Cys Asn Asn Gly Tyr Tyr Leu Leu Gly Asp Ser Arg Met
    1715                1720                1725

Phe Cys Thr Asp Asn Gly Ser Trp Asn Gly Val Ser Pro Ser Cys
    1730                1735                1740

Leu Asp Val Asp Glu Cys Ala Val Gly Ser Asp Cys Ser Glu His
    1745                1750                1755

Ala Ser Cys Leu Asn Val Asp Gly Ser Tyr Ile Cys Ser Cys Val
    1760                1765                1770

Pro Pro Tyr Thr Gly Asp Gly Lys Asn Cys Ala Glu Pro Ile Lys
    1775                1780                1785

Cys Lys Ala Pro Gly Asn Pro Glu Asn Gly His Ser Ser Gly Glu
    1790                1795                1800

Ile Tyr Thr Val Gly Ala Glu Val Thr Phe Ser Cys Gln Glu Gly
    1805                1810                1815

Tyr Gln Leu Met Gly Val Thr Lys Ile Thr Cys Leu Glu Ser Gly
    1820                1825                1830

Glu Trp Asn His Leu Ile Pro Tyr Cys Lys Ala Val Ser Cys Gly
    1835                1840                1845

Lys Pro Ala Ile Pro Glu Asn Gly Cys Ile Glu Glu Leu Ala Phe
    1850                1855                1860

Thr Phe Gly Ser Lys Val Thr Tyr Arg Cys Asn Lys Gly Tyr Thr
    1865                1870                1875

Leu Ala Gly Asp Lys Glu Ser Ser Cys Leu Ala Asn Ser Ser Trp
    1880                1885                1890

Ser His Ser Pro Pro Val Cys Glu Pro Val Lys Cys Ser Ser Pro
    1895                1900                1905

Glu Asn Ile Asn Asn Gly Lys Tyr Ile Leu Ser Gly Leu Thr Tyr
    1910                1915                1920

Leu Ser Thr Ala Ser Tyr Ser Cys Asp Thr Gly Tyr Ser Leu Gln
    1925                1930                1935

Gly Pro Ser Ile Ile Glu Cys Thr Ala Ser Gly Ile Trp Asp Arg
```

-continued

```
        1940                1945                1950
Ala Pro Pro Ala Cys His Leu Val Phe Cys Gly Glu Pro Pro Ala
        1955                1960                1965
Ile Lys Asp Ala Val Ile Thr Gly Asn Asn Phe Thr Phe Arg Asn
        1970                1975                1980
Thr Val Thr Tyr Thr Cys Lys Glu Gly Tyr Thr Leu Ala Gly Leu
        1985                1990                1995
Asp Thr Ile Glu Cys Leu Ala Asp Gly Lys Trp Ser Arg Ser Asp
        2000                2005                2010
Gln Gln Cys Leu Ala Val Ser Cys Asp Glu Pro Pro Ile Val Asp
        2015                2020                2025
His Ala Ser Pro Glu Thr Ala His Arg Leu Phe Gly Asp Ile Ala
        2030                2035                2040
Phe Tyr Tyr Cys Ser Asp Gly Tyr Ser Leu Ala Asp Asn Ser Gln
        2045                2050                2055
Leu Leu Cys Asn Ala Gln Gly Lys Trp Val Pro Pro Glu Gly Gln
        2060                2065                2070
Asp Met Pro Arg Cys Ile Ala His Phe Cys Glu Lys Pro Pro Ser
        2075                2080                2085
Val Ser Tyr Ser Ile Leu Glu Ser Val Ser Lys Ala Lys Phe Ala
        2090                2095                2100
Ala Gly Ser Val Val Ser Phe Lys Cys Met Glu Gly Phe Val Leu
        2105                2110                2115
Asn Thr Ser Ala Lys Ile Glu Cys Met Arg Gly Gly Gln Trp Asn
        2120                2125                2130
Pro Ser Pro Met Ser Ile Gln Cys Ile Pro Val Arg Cys Gly Glu
        2135                2140                2145
Pro Pro Ser Ile Met Asn Gly Tyr Ala Ser Gly Ser Asn Tyr Ser
        2150                2155                2160
Phe Gly Ala Met Val Ala Tyr Ser Cys Asn Lys Gly Phe Tyr Ile
        2165                2170                2175
Lys Gly Glu Lys Lys Ser Thr Cys Glu Ala Thr Gly Gln Trp Ser
        2180                2185                2190
Ser Pro Ile Pro Thr Cys His Pro Val Ser Cys Gly Glu Pro Pro
        2195                2200                2205
Lys Val Glu Asn Gly Phe Leu Glu His Thr Thr Gly Arg Ile Phe
        2210                2215                2220
Glu Ser Glu Val Arg Tyr Gln Cys Asn Pro Gly Tyr Lys Ser Val
        2225                2230                2235
Gly Ser Pro Val Phe Val Cys Gln Ala Asn Arg His Trp His Ser
        2240                2245                2250
Glu Ser Pro Leu Met Cys Val Pro Leu Asp Cys Gly Lys Pro Pro
        2255                2260                2265
Pro Ile Gln Asn Gly Phe Met Lys Gly Glu Asn Phe Glu Val Gly
        2270                2275                2280
Ser Lys Val Gln Phe Phe Cys Asn Glu Gly Tyr Glu Leu Val Gly
        2285                2290                2295
Asp Ser Ser Trp Thr Cys Gln Lys Ser Gly Lys Trp Asn Lys Lys
        2300                2305                2310
Ser Asn Pro Lys Cys Met Pro Ala Lys Cys Pro Glu Pro Pro Leu
        2315                2320                2325
Leu Glu Asn Gln Leu Val Leu Lys Glu Leu Thr Thr Glu Val Gly
        2330                2335                2340
```

-continued

```
Val Val Thr Phe Ser Cys Lys Glu Gly His Val Leu Gln Gly Pro
2345                2350                2355

Ser Val Leu Lys Cys Leu Pro Ser Gln Gln Trp Asn Asp Ser Phe
2360                2365                2370

Pro Val Cys Lys Ile Val Leu Cys Thr Pro Pro Leu Ile Ser
2375                2380                2385

Phe Gly Val Pro Ile Pro Ser Ser Ala Leu His Phe Gly Ser Thr
2390                2395                2400

Val Lys Tyr Ser Cys Val Gly Gly Phe Phe Leu Arg Gly Asn Ser
2405                2410                2415

Thr Thr Leu Cys Gln Pro Asp Gly Thr Trp Ser Ser Pro Leu Pro
2420                2425                2430

Glu Cys Val Pro Val Glu Cys Pro Gln Pro Glu Glu Ile Pro Asn
2435                2440                2445

Gly Ile Ile Asp Val Gln Gly Leu Ala Tyr Leu Ser Thr Ala Leu
2450                2455                2460

Tyr Thr Cys Lys Pro Gly Phe Glu Leu Val Gly Asn Thr Thr Thr
2465                2470                2475

Leu Cys Gly Glu Asn Gly His Trp Leu Gly Gly Lys Pro Thr Cys
2480                2485                2490

Lys Ala Ile Glu Cys Leu Lys Pro Lys Glu Ile Leu Asn Gly Lys
2495                2500                2505

Phe Ser Tyr Thr Asp Leu His Tyr Gly Gln Thr Val Thr Tyr Ser
2510                2515                2520

Cys Asn Arg Gly Phe Arg Leu Glu Gly Pro Ser Ala Leu Thr Cys
2525                2530                2535

Leu Glu Thr Gly Asp Trp Asp Val Asp Ala Pro Ser Cys Asn Ala
2540                2545                2550

Ile His Cys Asp Ser Pro Gln Pro Ile Glu Asn Gly Phe Val Glu
2555                2560                2565

Gly Ala Asp Tyr Ser Tyr Gly Ala Ile Ile Ile Tyr Ser Cys Phe
2570                2575                2580

Pro Gly Phe Gln Val Ala Gly His Ala Met Gln Thr Cys Glu Glu
2585                2590                2595

Ser Gly Trp Ser Ser Ser Ile Pro Thr Cys Met Pro Ile Asp Cys
2600                2605                2610

Gly Leu Pro Pro His Ile Asp Phe Gly Asp Cys Thr Lys Leu Lys
2615                2620                2625

Asp Asp Gln Gly Tyr Phe Glu Gln Glu Asp Asp Met Met Glu Val
2630                2635                2640

Pro Tyr Val Thr Pro His Pro Pro Tyr His Leu Gly Ala Val Ala
2645                2650                2655

Lys Thr Trp Glu Asn Thr Lys Glu Ser Pro Ala Thr His Ser Ser
2660                2665                2670

Asn Phe Leu Tyr Gly Thr Met Val Ser Tyr Thr Cys Asn Pro Gly
2675                2680                2685

Tyr Glu Leu Leu Gly Asn Pro Val Leu Ile Cys Gln Glu Asp Gly
2690                2695                2700

Thr Trp Asn Gly Ser Ala Pro Ser Cys Ile Ser Ile Glu Cys Asp
2705                2710                2715

Leu Pro Thr Ala Pro Glu Asn Gly Phe Leu Arg Phe Thr Glu Thr
2720                2725                2730
```

-continued

```
Ser Met Gly Ser Ala Val Gln Tyr Ser Cys Lys Pro Gly His Ile
    2735                2740                2745
Leu Val Gly Ser Asp Leu Arg Leu Cys Leu Glu Asn Arg Lys Trp
    2750                2755                2760
Ser Gly Ala Ser Pro Arg Cys Glu Ala Ile Ser Cys Lys Lys Pro
    2765                2770                2775
Asn Pro Val Met Asn Gly Ser Ile Lys Gly Ser Asn Tyr Thr Tyr
    2780                2785                2790
Leu Ser Thr Leu Tyr Tyr Glu Cys Asp Pro Gly Tyr Val Leu Asn
    2795                2800                2805
Gly Thr Glu Arg Arg Thr Cys Gln Asp Asp Lys Asn Trp Asp Glu
    2810                2815                2820
Asp Glu Pro Ile Cys Ile Pro Val Asp Cys Ser Ser Pro Pro Val
    2825                2830                2835
Ser Ala Asn Gly Gln Val Arg Gly Asp Glu Tyr Thr Phe Gln Lys
    2840                2845                2850
Glu Ile Glu Tyr Thr Cys Asn Glu Gly Phe Leu Leu Glu Gly Ala
    2855                2860                2865
Arg Ser Arg Val Cys Leu Ala Asn Gly Ser Trp Ser Gly Ala Thr
    2870                2875                2880
Pro Asp Cys Val Pro Val Arg Cys Ala Thr Pro Pro Gln Leu Ala
    2885                2890                2895
Asn Gly Val Thr Glu Gly Leu Asp Tyr Gly Phe Met Lys Glu Val
    2900                2905                2910
Thr Phe His Cys His Glu Gly Tyr Ile Leu His Gly Ala Pro Lys
    2915                2920                2925
Leu Thr Cys Gln Ser Asp Gly Asn Trp Asp Ala Glu Ile Pro Leu
    2930                2935                2940
Cys Lys Pro Val Asn Cys Gly Pro Pro Glu Asp Leu Ala His Gly
    2945                2950                2955
Phe Pro Asn Gly Phe Ser Phe Ile His Gly Gly His Ile Gln Tyr
    2960                2965                2970
Gln Cys Phe Pro Gly Tyr Lys Leu His Gly Asn Ser Ser Arg Arg
    2975                2980                2985
Cys Leu Ser Asn Gly Ser Trp Ser Gly Ser Ser Pro Ser Cys Leu
    2990                2995                3000
Pro Cys Arg Cys Ser Thr Pro Val Ile Glu Tyr Gly Thr Val Asn
    3005                3010                3015
Gly Thr Asp Phe Asp Cys Gly Lys Ala Ala Arg Ile Gln Cys Phe
    3020                3025                3030
Lys Gly Phe Lys Leu Leu Gly Leu Ser Glu Ile Thr Cys Glu Ala
    3035                3040                3045
Asp Gly Gln Trp Ser Ser Gly Phe Pro His Cys Glu His Thr Ser
    3050                3055                3060
Cys Gly Ser Leu Pro Met Ile Pro Asn Ala Phe Ile Ser Glu Thr
    3065                3070                3075
Ser Ser Trp Lys Glu Asn Val Ile Thr Tyr Ser Cys Arg Ser Gly
    3080                3085                3090
Tyr Val Ile Gln Gly Ser Ser Asp Leu Ile Cys Thr Glu Lys Gly
    3095                3100                3105
Val Trp Ser Gln Pro Tyr Pro Val Cys Glu Pro Leu Ser Cys Gly
    3110                3115                3120
Ser Pro Pro Ser Val Ala Asn Ala Val Ala Thr Gly Glu Ala His
```

-continued

```
            3125                3130                 3135

Thr Tyr Glu Ser Glu Val Lys Leu Arg Cys Leu Glu Gly Tyr Thr
        3140                3145                3150

Met Asp Thr Asp Thr Asp Thr Phe Thr Cys Gln Lys Asp Gly Arg
        3155                3160                3165

Trp Phe Pro Glu Arg Ile Ser Cys Ser Pro Lys Lys Cys Pro Leu
        3170                3175                3180

Pro Glu Asn Ile Thr His Ile Leu Val His Gly Asp Asp Phe Ser
        3185                3190                3195

Val Asn Arg Gln Val Ser Val Ser Cys Ala Glu Gly Tyr Thr Phe
        3200                3205                3210

Glu Gly Val Asn Ile Ser Val Cys Gln Leu Asp Gly Thr Trp Glu
        3215                3220                3225

Pro Pro Phe Ser Asp Glu Ser Cys Ser Pro Val Ser Cys Gly Lys
        3230                3235                3240

Pro Glu Ser Pro Glu His Gly Phe Val Val Gly Ser Lys Tyr Thr
        3245                3250                3255

Phe Glu Ser Thr Ile Ile Tyr Gln Cys Glu Pro Gly Tyr Glu Leu
        3260                3265                3270

Glu Gly Asn Arg Glu Arg Val Cys Gln Glu Asn Arg Gln Trp Ser
        3275                3280                3285

Gly Gly Val Ala Ile Cys Lys Glu Thr Arg Cys Glu Thr Pro Leu
        3290                3295                3300

Glu Phe Leu Asn Gly Lys Ala Asp Ile Glu Asn Arg Thr Thr Gly
        3305                3310                3315

Pro Asn Val Val Tyr Ser Cys Asn Arg Gly Tyr Ser Leu Glu Gly
        3320                3325                3330

Pro Ser Glu Ala His Cys Thr Glu Asn Gly Thr Trp Ser His Pro
        3335                3340                3345

Val Pro Leu Cys Lys Pro Asn Pro Cys Pro Val Pro Phe Val Ile
        3350                3355                3360

Pro Glu Asn Ala Leu Leu Ser Glu Lys Glu Phe Tyr Val Asp Gln
        3365                3370                3375

Asn Val Ser Ile Lys Cys Arg Glu Gly Phe Leu Leu Gln Gly His
        3380                3385                3390

Gly Ile Ile Thr Cys Asn Pro Asp Glu Thr Trp Thr Gln Thr Ser
        3395                3400                3405

Ala Lys Cys Glu Lys Ile Ser Cys Gly Pro Pro Ala His Val Glu
        3410                3415                3420

Asn Ala Ile Ala Arg Gly Val His Tyr Gln Tyr Gly Asp Met Ile
        3425                3430                3435

Thr Tyr Ser Cys Tyr Ser Gly Tyr Met Leu Glu Gly Phe Leu Arg
        3440                3445                3450

Ser Val Cys Leu Glu Asn Gly Thr Trp Thr Ser Pro Pro Ile Cys
        3455                3460                3465

Arg Ala Val Cys Arg Phe Pro Cys Gln Asn Gly Gly Ile Cys Gln
        3470                3475                3480

Arg Pro Asn Ala Cys Ser Cys Pro Glu Gly Trp Met Gly Arg Leu
        3485                3490                3495

Cys Glu Glu Pro Ile Cys Ile Leu Pro Cys Leu Asn Gly Gly Arg
        3500                3505                3510

Cys Val Ala Pro Tyr Gln Cys Asp Cys Pro Pro Gly Trp Thr Gly
        3515                3520                3525
```

-continued

Ser Arg Cys His Thr Ala Val Cys Gln Ser Pro Cys Leu Asn Gly
    3530                3535                3540

Gly Lys Cys Val Arg Pro Asn Arg Cys His Cys Leu Ser Ser Trp
    3545                3550                3555

Thr Gly His Asn Cys Ser Arg Lys Arg Arg Thr Gly Phe
    3560                3565                3570

<210> SEQ ID NO 3
<211> LENGTH: 11230
<212> TYPE: DNA
<213> ORGANISM: Mus musculus

<400> SEQUENCE: 3

```
ccccgagctg ccagaggagt ctggatcgtg tccccagtgt cacatgcaag gacgctgagg      60
ttcgcggttg ctaccccggg tcccctccgc ttagttcggg aaccttggcg cctctctgcg     120
cgctcgggga ctgtcgcctt gcactcccg gggccaccgc tcggtcccca gcgggatgtg     180
gtcgcgcctg gccttttgtt gctgggctct ggcactggtg tcgggctgga ccaacttcca     240
gcccgtggcc ccttcgctca acttcagctt ccgcctgttc cccgaggcct ctccggggc     300
tctgggcaga ctggcggtac ctcccgcgtc cagtgaggag gaggcagcag ggagcaaagt     360
ggagcgcctg ggccgcgcgt tccggagccg cgtgcggcga ctgcgggagc tcagcggcag     420
cctggagctc gtcttcctgg tggacgagtc gtccagcgtg gccaaacca acttcctcaa     480
cgagctcaag ttcgtgcgca agctgctgtc cgacttcccc gtggtgtcca cggccacgcg     540
tgtggccatc gtcaccttct catccaagaa caacgtggtg gcgcgcgtgg attacatctc     600
caccagccgc gcgcaccaac acaagtgcgc gctgctcagc cgcgagatcc cggccatcac     660
ctaccgcggt ggtggcacct ataccaaggg cgccttccag caagccgcgc aaatccttcg     720
tcactctaga gaaaactcca ccaaagtcat atttctcatc accgacggct attccaatgg     780
cggagacccc agacctattg cagcatcgct tcgggatttc ggagtggaga tcttcacgtt     840
cgggatttgg caggggaata tccgggaact gaatgacatg gcttccaccc gaaggaaga     900
acattgttac ctgctccaca gttttgaaga atttgaggct ttagctcgca gggcgttgca     960
tgaagatcta ccttctggga gttttatcca agaggatatg gcccactgct cttatctctg    1020
tgaggctggg aaagactgct gtgacagaat ggccagctgc aaatgtggga cacacacggg    1080
tcaatttgaa tgcatctgtg agaagggcta ttacgggaaa ggtctgcagc atgagtgcac    1140
agcttgccca tcagggacat ataagccgga agcttctcca ggaggaatca gcacctgcat    1200
cccatgtcct gacgtaagcc acacctcccc acctggaagc acttcccctg aagactgcgt    1260
gtgccgagag ggataccaga gatctggcca gacctgtgag gttgtccact gtcctgccct    1320
gaagcctcct gaaaatggtt ttttatacaa aacacttgc aaaaactact caatgccgc     1380
ctgtggggtc cgatgtcgcc cgggctttga ccttgtggga agcagcatcc atttgtgtca    1440
acccaatggt ttgtggtctg ggacagaaag cttctgcaga gtgagaacgt gcccccacct    1500
ccgacagccc aaacacggcc acatcagctg ctccactgcg gaaatgtcct acaacaccct    1560
gtgtttggtt acctgcaatg aaggatacag attagaaggc agcactaggc ttacctgtca    1620
aggaaatgcc cagtgggatg cccagagcc ccggtgtgta aacgccatt gtgccacctt     1680
ccagaagccc aaaggcgtca tcatttctcc acccagctgc ggcaagcagc ccgccaggcc    1740
tgggatgacc tgtcagctaa gctgccgcca gggatacatt ttatccgggg tcagagaagt    1800
gagatgtgcc acatctggga gtggagtgc caaagttcag acagctgtgt gcaaagatgt    1860
```

```
ggaggctcca caaatcagct gtccaaatga cattgaggca aagactgggg agcagcagga    1920
ctctgctaat gccacctggc aagtcccaac agctaaagac aactctggtg aaaaggtgtc    1980
agtccacgtc cacccagcct ttaccccacc ttacctcttc ccaattggag acgtggccat    2040
cacctacacg gcaaccgact catccggtaa ccaagccagc tgcactttct acattaaggt    2100
cattgatgtg gaaccgcctg tcatagattg gtgccgatct ccacctccaa tccaggtcgt    2160
agagaaggag caccctgcaa gctgggatga gcctcagttc tcagacaact ccggggctga    2220
attggtcatt accagcagtc acacacaagg cgacatgttt cctcatgggg aaacggtggt    2280
gtggtacaca gccactgacc cctcaggcaa caacaggacc tgtgacatcc acattgtcat    2340
aaaaggttct ccctgtgagg tccccttcac ccctgtaaac ggggacttta tctgtgccca    2400
ggatagtgct ggagttaact gtagcctgag ctgcaaggag ggctatgatt tcacagaagg    2460
gtcacctgag aagtactact gtgcttttga agatggtatc tggagaccac catactctac    2520
agaatggcca gactgtgcta taaaacgttt tgcaaaccat ggtttcaagt cctttgaaat    2580
gctatacaaa accactcgct gtgatgacat ggatctgttt aagaagtttt ctgcagcatt    2640
tgagactacc ctggggaaca tggtcccgtc cttttgtaac gatgctgatg acattgactg    2700
cagactggag gacctgacca aaaaatactg catcgagtat aattacaact atgaaaatgg    2760
ctttgcaatt ggaccaggag gctggggtgc aggcaacagg ctggattatt cctacgatca    2820
cttcctggat gttgtacagg aaacaccac cgatgtgggc aaggccagat cgtcacggat    2880
taaaagaact gtcccattgt ctgaccccaa aattcagcta attttttaaca tcacagctag    2940
cgtgccactc ccagaggaaa gaaacgatac ccttgaattg gagaatcagc agcgactcat    3000
taagacattg gaaacaatca ccaatcgcct gaaaagcacc ttgaataaag agcccatgta    3060
ttcttcccag ctcgcctcgg aaacagtggt ggctgacagc aattccctcg aaacagaaaa    3120
ggctttctc ttctgcagac caggctctgt gctgaggggg cgcatgtgtg tcaactgccc    3180
cctgggaacc tcttactctc tggagcattc cacctgtgaa agctgcctca tgggatccta    3240
ccaagatgaa gaagggcagc tggaatgcaa gctctgtccc ccaaggactc acgcggaata    3300
cctccattca agaagcgtct ctgaatgcaa agctcagtgt aagcaaggca cctactcttc    3360
cagtgggctg gagacctgcg aatcgtgtcc gctgggtact tatcaaccgg aatttggatc    3420
ccggagctgc ctcctatgcc cagaaaccac cacaacggtg aaaagaggag ccgtggacat    3480
ctctgcttgt ggagtgccct gcccagtagg agaattctcc cgttctgggc taacaccctg    3540
ctacccttgc cctcgagact attaccaacc caatgcaggg aagtccttct gcctcgcttg    3600
tcccttttat ggaactacaa ccatcactgg cgccacgtcc atcacagact gctcaagttt    3660
tagctctact ttctcagcag cagaagaaag catagtgccc ctcgtggccc ctggacattc    3720
ccagaacaag tacgaagtca gcagtcaggt ctttcacgaa tgcttcttaa accctgccca    3780
caacagtgga acctgccaac agcttgggcg tggttatgtc tgtctctgcc cacctggata    3840
cacaggctta aagtgtgaaa cagatattga tgaatgcagc tctctgccttt gcctcaatgg    3900
tggaatttgt agagaccaag ttgggggatt cacgtgcgaa tgttcattgg gctattcagg    3960
tcaaatatgt gaagaaaata taatgagtg tatctccagc ccttgcttaa ataaaggaac    4020
ctgcactgac ggcttggcaa gctaccgctg tacctgtgtg aaaggataca tgggtgtgca    4080
ctgtgaaaca gacgtcaatg aatgccagtc aagcccctgc ttaaacaacg cagttttgtaa    4140
agaccaagtt gggggggttct cgtgcaaatg cccacccgga ttttttgggta ctcggtgtga    4200
```

```
aaaaaatgtg gatgagtgtc tcagtcagcc atgccaaaat ggagccactt gtaaggatgg      4260
tgccaacagc ttcaggtgtc aatgtccagc aggcttcaca gggacacact gtgaactgaa      4320
catcaacgag tgtcagtcca acccgtgtag gaaccaggcc acctgtgtgg atgaactaaa      4380
ctcatacagt tgtaaatgtc agccaggatt tcaggccac aggtgtgaga cagaacagcc      4440
ttccggtttt aacctggatt ttgaagtttc tggcatctac gggtacgtcc tgctagatgg      4500
agtgctgcca accctccatg ccgtaacctg cgcattctgg atgaaatcct ctgatgtcat      4560
caactacggg acgcccatct cctatgcact gaggatgac aaagacaaca ccttcctcct       4620
gactgattac aacggctggg ttctttatgt gaatggaaag gaaagatca ccaactgccc       4680 ctccgtaaat gatggcattt ggcatcatat tgcaatcaca tggacaagta ttggtggagc      4740
ctggagggtc tatatagatg gggaattatc tgacggtggt actggcctct ccattggcaa      4800 agccataccct ggtggcggtg cattagttct tgggcaagag caagacaaaa aaggagaggg     4860
gttcaacccg gctgagtctt ttgtgggctc cataagccag ctcaacctct gggactatgt      4920
cctgtctcca cagcaggtga agttgctggc cagctcctgc ccagaggaac tgagtcgggg      4980
aaacgtgtta gcatggcccg atttcctgtc gggaatcacg gggaaggtga aggttgattc      5040
cagcagcatg ttctgctctg attgtccgtc tttagaagga tccgtgcctc acctgagacc      5100
tgcatcagga aatcgaaagc caggctccaa agtcagtctg ttctgtgatc cgggcttcca      5160
gatggttggg aatcctgtgc agtattgtct gaaccaaggg cagtggacac aaccactccc      5220
ccactgtgaa cgcattcgct gtgggctgcc tcccgccttg gagaatggct tctactcagc      5280
cgaggacttc catgcgggca gcacggtgac ctatcagtgc accagtggct actacctgct      5340
gggtgattcc cgaatgttct gcrcagacaa cgggagctgg aacggcattt caccatcctg      5400
tctcgatgtc gatgagtgtg cagtcggctc ggactgtagt gagcacgcct cctgcctgaa      5460
caccaacgga tcctacgtat gctcctgtaa cccaccatac acgggagatg ggaaaaactg      5520
tgcagaacct gtaaaatgta aggctccaga aaatccagaa aatggccgct cttctggcga      5580
gatttacacc gtgggtactg cagtcacatt ttcctgtgac gaagggcacg agctggtggg      5640
agtgagcacc atcacgtgtt tggagactgg cgagtgggat cgcctcaggc cgtcctgtga      5700
agccatttcc tgtggtgtcc cacctgttcc tgaaaatggt ggtgttgacg ggtcggcatt      5760
cacatatggc agtaaggtgg tgtacaggtg tgataaagga tatactttgt ctgggatga      5820 agagtcagca tgccttgcta gtggttcctg gagtcattcc tctcctgtgt gcgggctagt      5880
gaagtgttcc cagcctgagg acataaataa cggcaaatac atcttaagtg ggctcaccta      5940
cctttctatt gcatcgtact cctgtgagaa cggatacagt ttacagggcc catccctcct      6000
tgaatgcaca gcttccggca gctgggacag agcgccacct agctgtcaac ttgtctcctg      6060
cggagagcct ccaatcgtca aagatgctgt catcactggg agcaacttca cttttgggaa      6120
cacagttgct tacacatgca agagggcta caccccttgct gggcctgaca ccatcatatg      6180
ccaggccaac ggcaaatgga attcaagtaa ccaccagtgc ctggctgtct cctgtgacga      6240
gccccccaat gtggaccacg cctctccaga gactgctcac aggctctttg gagacaccgc      6300 gtttttactac tgtgcggatg gctacagcct ggctgataat tcccagctca tctgcaatgc      6360
ccaggggaac tgggttcccc ccgcgggcca ggctgtgccg cgctgcatag ctcacttctg      6420
tgaaaaaccc ccatctgttt cctacagcat cttggaatct gtgagcaaag caaagtttgc      6480
agctggctcg gtagtgagct tcaagtgcat ggagggtttt gtgctgaaca cctcagcgaa      6540
gattgaatgc ctgagaggtg gagagtggag ccttctcccc ctctcggtcc agtgcatccc      6600
```

-continued

```
ggtgcgatgc ggagagcctc caagcatcgc aaatggctac ccgagtggga caaactacag    6660
ttttggggcc gtggtggcct acagctgcca caaggattc tatatcaagg gggagaagaa     6720
gagcacgtgt gaggccacag gacagtggag taaacccacg cccacctgcc atcctgtgtc    6780
ctgtaacgag ccacctaagg ttgagaacgg cttcctggag cacaccactg gcaggacctt    6840
tgagagcgaa gcaaggttcc agtgcaaccc aggctataag gcagccggaa gtcctgtgtt    6900
tgtttgccaa gccaatcgcc actggcacag cgacgcccct ctgtcctgca ccctctcaa    6960 ctgtgggaaa ccccctccca ttcagaatgg ctttttgaaa ggagaaagct ttgaagtagg   7020
gtccaaggtt cagtttgtct gtaatgaggg atatgagctc gttggtgata attcttggac   7080
ttgccagaaa tctggcaaat ggagtaagaa gccaagcccg aagtgtgtcc ccaccaagtg    7140
tgcagagcct cctctcttag aaaaccagct cgtattgaag gaattagctt ccgaggtagg    7200
agtgatgacc atttcctgta aagagggca tgccttgcaa ggcccctctg tcctgaagtg     7260
cttgccatcc gggcaatgga atggttcctt tcctatttgt aagatggtcc tttgtccctc    7320
gcctcccttg attcccttcg gcgtccctgc gtcttccggt gctcttcatt ttggcagtac    7380
tgtcaagtat ctgtgtgtcg acgggttttt cttaagaggc agtccaacca tcctctgcca    7440
ggctgatagc acctggagtt ctccattgcc cgaatgcgtt ccggtagaat gtccccaacc    7500
tgaggagatc ctcaacggta tcatccacgt acaagggctt gcctatctca gcaccacgct    7560
ctacacctgc aagccaggct ttgagttagt gggcaatgct accaccctct gtggggaaaa    7620
tggccagtgg ctcggaggaa accaatgtg caaacccatt gaatgccag agcccaagga     7680 gattttaaat ggccaattct cttccgtgag ctttcagtat ggacaaacca tcacatactt    7740
ttgtgaccgg ggcttccggc tcgaaggtcc caaatccctg acctgtttag agacaggtga    7800
ctgggatatg gatcccccct cttgtgatgc catccactgc agtgacccac agcccattga    7860
aaatggtttc gtagaaggtg cggattacag atacggtgcc atgatcatct atagctgctt    7920
ccctgggttt caggtgcttg gtcatgccat gcagacctgt aaagagtcgg gatggtcaag    7980
ctccagccca acctgtgtac ccatagactg cggtctccct cctcacatag actttggtga    8040
ctgtactaaa gtcagagatg ccagggaca ttttgatcaa gaagatgaca tgatggaagt    8100
cccatatctg gctcacccte aacatttgga agcaacagct aaggccttgg aaaatacaaa    8160
ggagtcgcct gcctcacatg catcccactt cctctatggc acgatggttt cctacagctg    8220
cgagcctggt tatgaactgc tgggaatccc tgtgctgatc tgccaggaag atggtacgtg    8280
gaatggtacc gcaccctctt gcatttccat tgaatgtgat ttgcctgttg ctcccgaaaa    8340
tggcttttta catttcacac agacgactat gggcagtgct gcacaatata gctgcaagcc    8400
ggggcacatt ctagaaggct cccacttaag actctgtctg cagaataagc agtggagtgg    8460
cactgttcca cgctgtgaag ccatctcatg cagtaagcca aacccactct ggaatggatc    8520
catcaaagga gatgactact cctacctggg tgtgttatac tacgagtgtg actctggcta    8580
tattctcaat ggctctaaga gaggacatg ccaagaaaat agagattggg atgggcatga    8640
gcccatgtgt attcctgtag actgtggctc acccccagtc cccaccaatg ccgagtgaa    8700 gggagaagaa tacacattcc aaaaggagat tacatactct tgccgtgaag ggttcatact    8760
ggaaggagcc aggagtcgta tctgtcttac caatggaagt tggagtggtg ccactcccag   8820
ctgcatgcct gttagatgtc ctgccccacc acaggtgcca aatggggtgg cagatggcct    8880
agactatggg ttcaagaagg aagtagcgtt ccactgtcta gagggctatg tgctgcaggg    8940
```

```
ggctccaaga ctcacctgtc agtccaatgg gacttgggat gcagaagtcc ctgtctgtaa    9000
accagctacc tgtggtcctc ctgccgacct tccccagggc ttccctaatg gcttttcttt    9060
ttatcatggg ggccacatac agtatcagtg ttttactggt tataagcttc atggaaaccc    9120
atcaagaaga tgccttccca atggttcctg gagcggcagc tcgccatcct gcctaccttg    9180
caggtgttcc acacccatca ttcaacaggg aaccatcaac gcaactgatt tgggatgtgg    9240
aaagacggtc cagattgagt gcttcaaagg cttcaagctg cttggacttt ctgaaatcac    9300
ctgtgatgcc aatggccaat ggtctgacgt cccactgtgt gagcacgctc agtgcgggcc    9360
tctcccaacc atacccaacg caattgtcct tgagggcagc ctttcggagg acaatgtggt    9420
aacttacagc tgcagacctg gctacaccat gcaaggtagt tcagatctga tttgtacgga    9480
aaaagcgata tggagccagc cttacccaac gtgtgaaccc ctgtcctgtg gacccccacc    9540
aactgtagcc aatgcagtgg caacaggaga ggctcatacc tatgaaagca agtgaaaact    9600
caggtgtctg gaagggtatg tgatggattc ggatacagat acattcacct gccagcaaga    9660
tggccattgg gtccctgaaa gaatcacctg cagtcctaaa aaatgccctg tgccatccaa    9720
catgacacgc atacgttttc acggagatga cttccaggtg aacagacaag tttctgtgtc    9780
atgtgcagaa gggtttaccc acgaaggagt gaactggtca acatgccagc ccgacggtac    9840
atgggagcca ccattttctg atgaatcctg tatcccagtt gtttgtgggc atcctgaaag    9900
cccagcgcat ggctccgtgg ttggcaataa gcacagcttt ggaagcacca ttgtttacca    9960
gtgtgaccct ggctacaaat tagaggggaa cagggaacga atctgccagg agaacagaca    10020
gtggagtgga gaggtggcag tgtgcagaga gaacagatgt gagactccag ctgagtttcc    10080
caatgggaag gctgtcttgg aaaacaccac atctggaccc agccttctgt tttcctgtca    10140
cagaggctac accctggaag ggtcccccga ggcacactgc actgcaaatg gaacctggaa    10200
tcacctgact cccctctgca aaccaaatcc atgccctgtc ccttttgtga ttcctgagaa    10260
cgccgtcctt tctgaaaaag agttttatgt cgaccagaat gtatctatca agtgcagggac    10320 aggcttcctg ctcaaaggca atggtgtcat cacgtgcagc cctgacgaga catggacgca    10380
caccaatgcc agatgtgaaa aaatctcctg tggtcctcca agtcacgtag agaatgcaat    10440
tgctcgagga gtgtattacc agtatgggga catgatcacc tactcctgtt acagtggcta    10500
catgctagaa ggttccctcc ggagtgtttg cctagaaaat ggaacatgga caccatctcc    10560
tgtttgcaga gctgtctgtc ggttcccatg tcagaatgga ggtgtctgtc aacgtccaaa    10620
tgcttgctca tgcccagacg gctggatggg acgtctctgt gaagagccaa tatgcatact    10680
cccctgtttg aatggtgggc gctgtgtggc cccttatcag tgtgactgcc ccacaggctg    10740
gactgggtcc cgctgtcata cagctacttg tcagtccccc tgcttaaatg gcgggaaatg    10800
cataagacca aaccgatgcc attgtctctc agcctggaca ggacatgatt gttccaggaa    10860
aaggagagcc gggctttgat ctcatgcccc acccccctctc cctaagcagc atcatctcct    10920
tccggtagct cctgggactc ccaccaagaa agaccaacgc ggtgctgggg cttgtttggt    10980
tttataagct tgaggttgac ttttttaattt tgtgatctat tttgttaaat ttttttgtga    11040 cgtccttctcc tacatgtgtg cgttgtttaa atatgcttgc attttctata taaaatttat    11100
attaaacgga cgcacttcat cctcaccaga tgtacatact ctgctgtctg ctgggaaagc    11160
ccctggaata catttttatt caattactta aagatgactt tccattaaaa tatattttgc    11220
tactaaaaaa                                                            11230
```

<210> SEQ ID NO 4
<211> LENGTH: 3594
<212> TYPE: PRT
<213> ORGANISM: Mus musculus
<220> FEATURE:
<221> NAME/KEY: misc_feature
<222> LOCATION: (1757)..()
<223> OTHER INFORMATION: Xaa = any or unknown amino acid

<400> SEQUENCE: 4

```
Phe Gly Asn Leu Gly Ala Ser Leu Arg Ala Arg Gly Leu Ser Pro Cys
  1               5                  10                  15

Thr Pro Arg Gly His Arg Ser Val Pro Ser Gly Met Trp Ser Arg Leu
             20                  25                  30

Ala Phe Cys Cys Trp Ala Leu Ala Leu Val Ser Gly Trp Thr Asn Phe
         35                  40                  45

Gln Pro Val Ala Pro Ser Leu Asn Phe Ser Phe Arg Leu Phe Pro Glu
     50                  55                  60

Ala Ser Pro Gly Ala Leu Gly Arg Leu Ala Val Pro Pro Ala Ser Ser
 65                  70                  75                  80

Glu Glu Glu Ala Ala Gly Ser Lys Val Glu Arg Leu Gly Arg Ala Phe
                 85                  90                  95

Arg Ser Arg Val Arg Arg Leu Arg Glu Leu Ser Gly Ser Leu Glu Leu
            100                 105                 110

Val Phe Leu Val Asp Glu Ser Ser Val Gly Gln Thr Asn Phe Leu
            115                 120                 125

Asn Glu Leu Lys Phe Val Arg Lys Leu Leu Ser Asp Phe Pro Val Val
    130                 135                 140

Ser Thr Ala Thr Arg Val Ala Ile Val Thr Phe Ser Ser Lys Asn Asn
145                 150                 155                 160

Val Val Ala Arg Val Asp Tyr Ile Ser Thr Ser Arg Ala His Gln His
                165                 170                 175

Lys Cys Ala Leu Leu Ser Arg Glu Ile Pro Ala Ile Thr Tyr Arg Gly
            180                 185                 190

Gly Gly Thr Tyr Thr Lys Gly Ala Phe Gln Gln Ala Ala Gln Ile Leu
        195                 200                 205

Arg His Ser Arg Glu Asn Ser Thr Lys Val Ile Phe Leu Ile Thr Asp
    210                 215                 220

Gly Tyr Ser Asn Gly Gly Asp Pro Arg Pro Ile Ala Ala Ser Leu Arg
225                 230                 235                 240

Asp Phe Gly Val Glu Ile Phe Thr Phe Gly Ile Trp Gln Gly Asn Ile
                245                 250                 255

Arg Glu Leu Asn Asp Met Ala Ser Thr Pro Lys Glu Glu His Cys Tyr
            260                 265                 270

Leu Leu His Ser Phe Glu Glu Phe Glu Ala Leu Ala Arg Arg Ala Leu
        275                 280                 285

His Glu Asp Leu Pro Ser Gly Ser Phe Ile Gln Glu Asp Met Ala His
    290                 295                 300

Cys Ser Tyr Leu Cys Glu Ala Gly Lys Asp Cys Asp Arg Met Ala
305                 310                 315                 320

Ser Cys Lys Cys Gly Thr His Thr Gly Gln Phe Glu Cys Ile Cys Glu
                325                 330                 335

Lys Gly Tyr Tyr Gly Lys Gly Leu Gln His Glu Cys Thr Ala Cys Pro
            340                 345                 350

Ser Gly Thr Tyr Lys Pro Glu Ala Ser Pro Gly Gly Ile Ser Thr Cys
        355                 360                 365
```

-continued

```
Ile Pro Cys Pro Asp Val Ser His Thr Ser Pro Gly Ser Thr Ser
370                 375                 380
Pro Glu Asp Cys Val Cys Arg Glu Gly Tyr Gln Arg Ser Gly Gln Thr
385                 390                 395                 400
Cys Glu Val Val His Cys Pro Ala Leu Lys Pro Pro Glu Asn Gly Phe
                405                 410                 415
Phe Ile Gln Asn Thr Cys Lys Asn Tyr Phe Asn Ala Ala Cys Gly Val
            420                 425                 430
Arg Cys Arg Pro Gly Phe Asp Leu Val Gly Ser Ser Ile His Leu Cys
        435                 440                 445
Gln Pro Asn Gly Leu Trp Ser Gly Thr Glu Ser Phe Cys Arg Val Arg
    450                 455                 460
Thr Cys Pro His Leu Arg Gln Pro Lys His Gly His Ile Ser Cys Ser
465                 470                 475                 480
Thr Ala Glu Met Ser Tyr Asn Thr Leu Cys Leu Val Thr Cys Asn Glu
                485                 490                 495
Gly Tyr Arg Leu Glu Gly Ser Thr Arg Leu Thr Cys Gln Gly Asn Ala
            500                 505                 510
Gln Trp Asp Gly Pro Glu Pro Arg Cys Val Glu Arg His Cys Ala Thr
        515                 520                 525
Phe Gln Lys Pro Lys Gly Val Ile Ile Ser Pro Pro Ser Cys Gly Lys
    530                 535                 540
Gln Pro Ala Arg Pro Gly Met Thr Cys Gln Leu Ser Cys Arg Gln Gly
545                 550                 555                 560
Tyr Ile Leu Ser Gly Val Arg Glu Val Arg Cys Ala Thr Ser Gly Lys
                565                 570                 575
Trp Ser Ala Lys Val Gln Thr Ala Val Cys Lys Asp Val Glu Ala Pro
            580                 585                 590
Gln Ile Ser Cys Pro Asn Asp Ile Glu Ala Lys Thr Gly Glu Gln Gln
        595                 600                 605
Asp Ser Ala Asn Ala Thr Trp Gln Val Pro Thr Ala Lys Asp Asn Ser
    610                 615                 620
Gly Glu Lys Val Ser Val His Val His Pro Ala Phe Thr Pro Pro Tyr
625                 630                 635                 640
Leu Phe Pro Ile Gly Asp Val Ala Ile Thr Tyr Thr Ala Thr Asp Ser
                645                 650                 655
Ser Gly Asn Gln Ala Ser Cys Thr Phe Tyr Ile Lys Val Ile Asp Val
            660                 665                 670
Glu Pro Pro Val Ile Asp Trp Cys Arg Ser Pro Pro Ile Gln Val
        675                 680                 685
Val Glu Lys Glu His Pro Ala Ser Trp Asp Glu Pro Gln Phe Ser Asp
    690                 695                 700
Asn Ser Gly Ala Glu Leu Val Ile Thr Ser Ser His Thr Gln Gly Asp
705                 710                 715                 720
Met Phe Pro His Gly Glu Thr Val Val Trp Tyr Thr Ala Thr Asp Pro
                725                 730                 735
Ser Gly Asn Asn Arg Thr Cys Asp Ile His Ile Val Ile Lys Gly Ser
            740                 745                 750
Pro Cys Glu Val Pro Phe Thr Pro Val Asn Gly Asp Phe Ile Cys Ala
        755                 760                 765
Gln Asp Ser Ala Gly Val Asn Cys Ser Leu Ser Cys Lys Glu Gly Tyr
    770                 775                 780
```

-continued

```
Asp Phe Thr Glu Gly Ser Pro Glu Lys Tyr Tyr Cys Ala Phe Glu Asp
785                 790                 795                 800

Gly Ile Trp Arg Pro Pro Tyr Ser Thr Glu Trp Pro Asp Cys Ala Ile
                805                 810                 815

Lys Arg Phe Ala Asn His Gly Phe Lys Ser Phe Glu Met Leu Tyr Lys
                820                 825                 830

Thr Thr Arg Cys Asp Asp Met Asp Leu Phe Lys Lys Phe Ser Ala Ala
                835                 840                 845

Phe Glu Thr Thr Leu Gly Asn Met Val Pro Ser Phe Cys Asn Asp Ala
850                 855                 860

Asp Asp Ile Asp Cys Arg Leu Glu Asp Leu Thr Lys Lys Tyr Cys Ile
865                 870                 875                 880

Glu Tyr Asn Tyr Asn Tyr Glu Asn Gly Phe Ala Ile Gly Pro Gly Gly
                885                 890                 895

Trp Gly Ala Gly Asn Arg Leu Asp Tyr Ser Tyr Asp His Phe Leu Asp
                900                 905                 910

Val Val Gln Glu Thr Pro Thr Asp Val Gly Lys Ala Arg Ser Ser Arg
                915                 920                 925

Ile Lys Arg Thr Val Pro Leu Ser Asp Pro Lys Ile Gln Leu Ile Phe
930                 935                 940

Asn Ile Thr Ala Ser Val Pro Leu Pro Glu Glu Arg Asn Asp Thr Leu
945                 950                 955                 960

Glu Leu Glu Asn Gln Gln Arg Leu Ile Lys Thr Leu Glu Thr Ile Thr
                965                 970                 975

Asn Arg Leu Lys Ser Thr Leu Asn Lys Glu Pro Met Tyr Ser Phe Gln
                980                 985                 990

Leu Ala Ser Glu Thr Val Val Ala  Asp Ser Asn Ser Leu  Glu Thr Glu
                995                 1000                1005

Lys Ala  Phe Leu Phe Cys Arg  Pro Gly Ser Val Leu  Arg Gly Arg
    1010                1015                1020

Met Cys  Val Asn Cys Pro Leu  Gly Thr Ser Tyr Ser  Leu Glu His
    1025                1030                1035

Ser Thr  Cys Glu Ser Cys Leu  Met Gly Ser Tyr Gln  Asp Glu Glu
    1040                1045                1050

Gly Gln  Leu Glu Cys Lys Leu  Cys Pro Pro Arg Thr  His Ala Glu
    1055                1060                1065

Tyr Leu  His Ser Arg Ser Val  Ser Glu Cys Lys Ala  Gln Cys Lys
    1070                1075                1080

Gln Gly  Thr Tyr Ser Ser Ser  Gly Leu Glu Thr Cys  Glu Ser Cys
    1085                1090                1095

Pro Leu  Gly Thr Tyr Gln Pro  Glu Phe Gly Ser Arg  Ser Cys Leu
    1100                1105                1110

Leu Cys  Pro Glu Thr Thr Thr  Thr Val Lys Arg Gly  Ala Val Asp
    1115                1120                1125

Ile Ser  Ala Cys Gly Val Pro  Cys Pro Val Gly Glu  Phe Ser Arg
    1130                1135                1140

Ser Gly  Leu Thr Pro Cys Tyr  Pro Cys Pro Arg Asp  Tyr Tyr Gln
    1145                1150                1155

Pro Asn  Ala Gly Lys Ser Phe  Cys Leu Ala Cys Pro  Phe Tyr Gly
    1160                1165                1170

Thr Thr  Thr Ile Thr Gly Ala  Thr Ser Ile Thr Asp  Cys Ser Ser
    1175                1180                1185

Phe Ser  Ser Thr Phe Ser Ala  Ala Glu Glu Ser Ile  Val Pro Leu
```

-continued

```
             1190                1195                1200

Val Ala Pro Gly His Ser Gln Asn Lys Tyr Glu Val Ser Ser Gln
    1205                1210                1215

Val Phe His Glu Cys Phe Leu Asn Pro Cys His Asn Ser Gly Thr
    1220                1225                1230

Cys Gln Gln Leu Gly Arg Gly Tyr Val Cys Leu Cys Pro Pro Gly
    1235                1240                1245

Tyr Thr Gly Leu Lys Cys Glu Thr Asp Ile Asp Glu Cys Ser Ser
    1250                1255                1260

Leu Pro Cys Leu Asn Gly Gly Ile Cys Arg Asp Gln Val Gly Gly
    1265                1270                1275

Phe Thr Cys Glu Cys Ser Leu Gly Tyr Ser Gly Gln Ile Cys Glu
    1280                1285                1290

Glu Asn Ile Asn Glu Cys Ile Ser Ser Pro Cys Leu Asn Lys Gly
    1295                1300                1305

Thr Cys Thr Asp Gly Leu Ala Ser Tyr Arg Cys Thr Cys Val Lys
    1310                1315                1320

Gly Tyr Met Gly Val His Cys Glu Thr Asp Val Asn Glu Cys Gln
    1325                1330                1335

Ser Ser Pro Cys Leu Asn Asn Ala Val Cys Lys Asp Gln Val Gly
    1340                1345                1350

Gly Phe Ser Cys Lys Cys Pro Pro Gly Phe Leu Gly Thr Arg Cys
    1355                1360                1365

Glu Lys Asn Val Asp Glu Cys Leu Ser Gln Pro Cys Gln Asn Gly
    1370                1375                1380

Ala Thr Cys Lys Asp Gly Ala Asn Ser Phe Arg Cys Gln Cys Pro
    1385                1390                1395

Ala Gly Phe Thr Gly Thr His Cys Glu Leu Asn Ile Asn Glu Cys
    1400                1405                1410

Gln Ser Asn Pro Cys Arg Asn Gln Ala Thr Cys Val Asp Glu Leu
    1415                1420                1425

Asn Ser Tyr Ser Cys Lys Cys Gln Pro Gly Phe Ser Gly His Arg
    1430                1435                1440

Cys Glu Thr Glu Gln Pro Ser Gly Phe Asn Leu Asp Phe Glu Val
    1445                1450                1455

Ser Gly Ile Tyr Gly Tyr Val Leu Leu Asp Gly Val Leu Pro Thr
    1460                1465                1470

Leu His Ala Val Thr Cys Ala Phe Trp Met Lys Ser Ser Asp Val
    1475                1480                1485

Ile Asn Tyr Gly Thr Pro Ile Ser Tyr Ala Leu Glu Asp Asp Lys
    1490                1495                1500

Asp Asn Thr Phe Leu Leu Thr Asp Tyr Asn Gly Trp Val Leu Tyr
    1505                1510                1515

Val Asn Gly Lys Glu Lys Ile Thr Asn Cys Pro Ser Val Asn Asp
    1520                1525                1530

Gly Ile Trp His His Ile Ala Ile Thr Trp Thr Ser Ile Gly Gly
    1535                1540                1545

Ala Trp Arg Val Tyr Ile Asp Gly Glu Leu Ser Asp Gly Gly Thr
    1550                1555                1560

Gly Leu Ser Ile Gly Lys Ala Ile Pro Gly Gly Gly Ala Leu Val
    1565                1570                1575

Leu Gly Gln Glu Gln Asp Lys Lys Gly Glu Gly Phe Asn Pro Ala
    1580                1585                1590
```

-continued

| | | | | | | | | | | | |
|---|---|---|---|---|---|---|---|---|---|---|---|
| Glu | Ser | Phe | Val | Gly | Ser | Ile | Ser | Gln | Leu | Asn | Leu | Trp | Asp | Tyr |
| | 1595 | | | | 1600 | | | | 1605 | | |
| Val | Leu | Ser | Pro | Gln | Gln | Val | Lys | Leu | Leu | Ala | Ser | Ser | Cys | Pro |
| 1610 | | | | | 1615 | | | | | 1620 | | |
| Glu | Glu | Leu | Ser | Arg | Gly | Asn | Val | Leu | Ala | Trp | Pro | Asp | Phe | Leu |
| 1625 | | | | | 1630 | | | | | 1635 | | |
| Ser | Gly | Ile | Thr | Gly | Lys | Val | Lys | Val | Asp | Ser | Ser | Ser | Met | Phe |
| 1640 | | | | | 1645 | | | | | 1650 | | |
| Cys | Ser | Asp | Cys | Pro | Ser | Leu | Glu | Gly | Ser | Val | Pro | His | Leu | Arg |
| 1655 | | | | | 1660 | | | | | 1665 | | |
| Pro | Ala | Ser | Gly | Asn | Arg | Lys | Pro | Gly | Ser | Lys | Val | Ser | Leu | Phe |
| 1670 | | | | | 1675 | | | | | 1680 | | |
| Cys | Asp | Pro | Gly | Phe | Gln | Met | Val | Gly | Asn | Pro | Val | Gln | Tyr | Cys |
| 1685 | | | | | 1690 | | | | | 1695 | | |
| Leu | Asn | Gln | Gly | Gln | Trp | Thr | Gln | Pro | Leu | Pro | His | Cys | Glu | Arg |
| 1700 | | | | | 1705 | | | | | 1710 | | |
| Ile | Arg | Cys | Gly | Leu | Pro | Pro | Ala | Leu | Glu | Asn | Gly | Phe | Tyr | Ser |
| 1715 | | | | | 1720 | | | | | 1725 | | |
| Ala | Glu | Asp | Phe | His | Ala | Gly | Ser | Thr | Val | Thr | Tyr | Gln | Cys | Thr |
| 1730 | | | | | 1735 | | | | | 1740 | | |
| Ser | Gly | Tyr | Tyr | Leu | Leu | Gly | Asp | Ser | Arg | Met | Phe | Cys | Xaa | Asp |
| 1745 | | | | | 1750 | | | | | 1755 | | |
| Asn | Gly | Ser | Trp | Asn | Gly | Ile | Ser | Pro | Ser | Cys | Leu | Asp | Val | Asp |
| 1760 | | | | | 1765 | | | | | 1770 | | |
| Glu | Cys | Ala | Val | Gly | Ser | Asp | Cys | Ser | Glu | His | Ala | Ser | Cys | Leu |
| 1775 | | | | | 1780 | | | | | 1785 | | |
| Asn | Thr | Asn | Gly | Ser | Tyr | Val | Cys | Ser | Cys | Asn | Pro | Pro | Tyr | Thr |
| 1790 | | | | | 1795 | | | | | 1800 | | |
| Gly | Asp | Gly | Lys | Asn | Cys | Ala | Glu | Pro | Val | Lys | Cys | Lys | Ala | Pro |
| 1805 | | | | | 1810 | | | | | 1815 | | |
| Glu | Asn | Pro | Glu | Asn | Gly | Arg | Ser | Ser | Gly | Glu | Ile | Tyr | Thr | Val |
| 1820 | | | | | 1825 | | | | | 1830 | | |
| Gly | Thr | Ala | Val | Thr | Phe | Ser | Cys | Asp | Glu | Gly | His | Glu | Leu | Val |
| 1835 | | | | | 1840 | | | | | 1845 | | |
| Gly | Val | Ser | Thr | Ile | Thr | Cys | Leu | Glu | Thr | Gly | Glu | Trp | Asp | Arg |
| 1850 | | | | | 1855 | | | | | 1860 | | |
| Leu | Arg | Pro | Ser | Cys | Glu | Ala | Ile | Ser | Cys | Gly | Val | Pro | Pro | Val |
| 1865 | | | | | 1870 | | | | | 1875 | | |
| Pro | Glu | Asn | Gly | Gly | Val | Asp | Gly | Ser | Ala | Phe | Thr | Tyr | Gly | Ser |
| 1880 | | | | | 1885 | | | | | 1890 | | |
| Lys | Val | Val | Tyr | Arg | Cys | Asp | Lys | Gly | Tyr | Thr | Leu | Ser | Gly | Asp |
| 1895 | | | | | 1900 | | | | | 1905 | | |
| Glu | Glu | Ser | Ala | Cys | Leu | Ala | Ser | Gly | Ser | Trp | Ser | His | Ser | Ser |
| 1910 | | | | | 1915 | | | | | 1920 | | |
| Pro | Val | Cys | Gly | Leu | Val | Lys | Cys | Ser | Gln | Pro | Glu | Asp | Ile | Asn |
| 1925 | | | | | 1930 | | | | | 1935 | | |
| Asn | Gly | Lys | Tyr | Ile | Leu | Ser | Gly | Leu | Thr | Tyr | Leu | Ser | Ile | Ala |
| 1940 | | | | | 1945 | | | | | 1950 | | |
| Ser | Tyr | Ser | Cys | Glu | Asn | Gly | Tyr | Ser | Leu | Gln | Gly | Pro | Ser | Leu |
| 1955 | | | | | 1960 | | | | | 1965 | | |
| Leu | Glu | Cys | Thr | Ala | Ser | Gly | Ser | Trp | Asp | Arg | Ala | Pro | Pro | Ser |
| 1970 | | | | | 1975 | | | | | 1980 | | |

```
Cys Gln Leu Val Ser Cys Gly Glu Pro Ile Val Lys Asp Ala
    1985                1990            1995

Val Ile Thr Gly Ser Asn Phe Thr Phe Gly Asn Thr Val Ala Tyr
    2000            2005            2010

Thr Cys Lys Glu Gly Tyr Thr Leu Ala Gly Pro Asp Thr Ile Ile
    2015            2020            2025

Cys Gln Ala Asn Gly Lys Trp Asn Ser Ser Asn His Gln Cys Leu
    2030            2035            2040

Ala Val Ser Cys Asp Glu Pro Pro Asn Val Asp His Ala Ser Pro
    2045            2050            2055

Glu Thr Ala His Arg Leu Phe Gly Asp Thr Ala Phe Tyr Tyr Cys
    2060            2065            2070

Ala Asp Gly Tyr Ser Leu Ala Asp Asn Ser Gln Leu Ile Cys Asn
    2075            2080            2085

Ala Gln Gly Asn Trp Val Pro Pro Ala Gly Gln Ala Val Pro Arg
    2090            2095            2100

Cys Ile Ala His Phe Cys Glu Lys Pro Pro Ser Val Ser Tyr Ser
    2105            2110            2115

Ile Leu Glu Ser Val Ser Lys Ala Lys Phe Ala Ala Gly Ser Val
    2120            2125            2130

Val Ser Phe Lys Cys Met Glu Gly Phe Val Leu Asn Thr Ser Ala
    2135            2140            2145

Lys Ile Glu Cys Leu Arg Gly Gly Glu Trp Ser Pro Ser Pro Leu
    2150            2155            2160

Ser Val Gln Cys Ile Pro Val Arg Cys Gly Glu Pro Pro Ser Ile
    2165            2170            2175

Ala Asn Gly Tyr Pro Ser Gly Thr Asn Tyr Ser Phe Gly Ala Val
    2180            2185            2190

Val Ala Tyr Ser Cys His Lys Gly Phe Tyr Ile Lys Gly Glu Lys
    2195            2200            2205

Lys Ser Thr Cys Glu Ala Thr Gly Gln Trp Ser Lys Pro Thr Pro
    2210            2215            2220

Thr Cys His Pro Val Ser Cys Asn Glu Pro Pro Lys Val Glu Asn
    2225            2230            2235

Gly Phe Leu Glu His Thr Thr Gly Arg Thr Phe Glu Ser Glu Ala
    2240            2245            2250

Arg Phe Gln Cys Asn Pro Gly Tyr Lys Ala Ala Gly Ser Pro Val
    2255            2260            2265

Phe Val Cys Gln Ala Asn Arg His Trp His Ser Asp Ala Pro Leu
    2270            2275            2280

Ser Cys Thr Pro Leu Asn Cys Gly Lys Pro Pro Ile Gln Asn
    2285            2290            2295

Gly Phe Leu Lys Gly Glu Ser Phe Glu Val Gly Ser Lys Val Gln
    2300            2305            2310

Phe Val Cys Asn Glu Gly Tyr Glu Leu Val Gly Asp Asn Ser Trp
    2315            2320            2325

Thr Cys Gln Lys Ser Gly Lys Trp Ser Lys Pro Ser Pro Lys
    2330            2335            2340

Cys Val Pro Thr Lys Cys Ala Glu Pro Pro Leu Leu Glu Asn Gln
    2345            2350            2355

Leu Val Leu Lys Glu Leu Ala Ser Glu Val Gly Val Met Thr Ile
    2360            2365            2370

Ser Cys Lys Glu Gly His Ala Leu Gln Gly Pro Ser  Val Leu Lys
```

-continued

|     |     |     |     |     |     |     |     |     |     |     |     |
|---|---|---|---|---|---|---|---|---|---|---|---|
| | 2375 | | | 2380 | | | 2385 | | | | |
| Cys | Leu | Pro | Ser | Gly | Gln | Trp | Asn | Gly | Ser | Phe | Pro | Ile | Cys | Lys |
| | 2390 | | | | 2395 | | | 2400 | | | |
| Met | Val | Leu | Cys | Pro | Ser | Pro | Pro | Leu | Ile | Pro | Phe | Gly | Val | Pro |
| 2405 | | | | 2410 | | | 2415 | | | | |
| Ala | Ser | Ser | Gly | Ala | Leu | His | Phe | Gly | Ser | Thr | Val | Lys | Tyr | Leu |
| 2420 | | | | 2425 | | | 2430 | | | | |
| Cys | Val | Asp | Gly | Phe | Phe | Leu | Arg | Gly | Ser | Pro | Thr | Ile | Leu | Cys |
| 2435 | | | | 2440 | | | 2445 | | | | |
| Gln | Ala | Asp | Ser | Thr | Trp | Ser | Ser | Pro | Leu | Pro | Glu | Cys | Val | Pro |
| 2450 | | | | 2455 | | | 2460 | | | | |
| Val | Glu | Cys | Pro | Gln | Pro | Glu | Glu | Ile | Leu | Asn | Gly | Ile | Ile | His |
| 2465 | | | | 2470 | | | 2475 | | | | |
| Val | Gln | Gly | Leu | Ala | Tyr | Leu | Ser | Thr | Thr | Leu | Tyr | Thr | Cys | Lys |
| 2480 | | | | 2485 | | | 2490 | | | | |
| Pro | Gly | Phe | Glu | Leu | Val | Gly | Asn | Ala | Thr | Thr | Leu | Cys | Gly | Glu |
| 2495 | | | | 2500 | | | 2505 | | | | |
| Asn | Gly | Gln | Trp | Leu | Gly | Gly | Lys | Pro | Met | Cys | Lys | Pro | Ile | Glu |
| 2510 | | | | 2515 | | | 2520 | | | | |
| Cys | Pro | Glu | Pro | Lys | Glu | Ile | Leu | Asn | Gly | Gln | Phe | Ser | Ser | Val |
| 2525 | | | | 2530 | | | 2535 | | | | |
| Ser | Phe | Gln | Tyr | Gly | Gln | Thr | Ile | Thr | Tyr | Phe | Cys | Asp | Arg | Gly |
| 2540 | | | | 2545 | | | 2550 | | | | |
| Phe | Arg | Leu | Glu | Gly | Pro | Lys | Ser | Leu | Thr | Cys | Leu | Glu | Thr | Gly |
| 2555 | | | | 2560 | | | 2565 | | | | |
| Asp | Trp | Asp | Met | Asp | Pro | Pro | Ser | Cys | Asp | Ala | Ile | His | Cys | Ser |
| 2570 | | | | 2575 | | | 2580 | | | | |
| Asp | Pro | Gln | Pro | Ile | Glu | Asn | Gly | Phe | Val | Glu | Gly | Ala | Asp | Tyr |
| 2585 | | | | 2590 | | | 2595 | | | | |
| Arg | Tyr | Gly | Ala | Met | Ile | Ile | Tyr | Ser | Cys | Phe | Pro | Gly | Phe | Gln |
| 2600 | | | | 2605 | | | 2610 | | | | |
| Val | Leu | Gly | His | Ala | Met | Gln | Thr | Cys | Glu | Glu | Ser | Gly | Trp | Ser |
| 2615 | | | | 2620 | | | 2625 | | | | |
| Ser | Ser | Ser | Pro | Thr | Cys | Val | Pro | Ile | Asp | Cys | Gly | Leu | Pro | Pro |
| 2630 | | | | 2635 | | | 2640 | | | | |
| His | Ile | Asp | Phe | Gly | Asp | Cys | Thr | Lys | Val | Arg | Asp | Gly | Gln | Gly |
| 2645 | | | | 2650 | | | 2655 | | | | |
| His | Phe | Asp | Gln | Glu | Asp | Asp | Met | Met | Glu | Val | Pro | Tyr | Leu | Ala |
| 2660 | | | | 2665 | | | 2670 | | | | |
| His | Pro | Gln | His | Leu | Glu | Ala | Thr | Ala | Lys | Ala | Leu | Glu | Asn | Thr |
| 2675 | | | | 2680 | | | 2685 | | | | |
| Lys | Glu | Ser | Pro | Ala | Ser | His | Ala | Ser | His | Phe | Leu | Tyr | Gly | Thr |
| 2690 | | | | 2695 | | | 2700 | | | | |
| Met | Val | Ser | Tyr | Ser | Cys | Glu | Pro | Gly | Tyr | Glu | Leu | Leu | Gly | Ile |
| 2705 | | | | 2710 | | | 2715 | | | | |
| Pro | Val | Leu | Ile | Cys | Gln | Glu | Asp | Gly | Thr | Trp | Asn | Gly | Thr | Ala |
| 2720 | | | | 2725 | | | 2730 | | | | |
| Pro | Ser | Cys | Ile | Ser | Ile | Glu | Cys | Asp | Leu | Pro | Val | Ala | Pro | Glu |
| 2735 | | | | 2740 | | | 2745 | | | | |
| Asn | Gly | Phe | Leu | His | Phe | Thr | Gln | Thr | Thr | Met | Gly | Ser | Ala | Ala |
| 2750 | | | | 2755 | | | 2760 | | | | |
| Gln | Tyr | Ser | Cys | Lys | Pro | Gly | His | Ile | Leu | Glu | Gly | Ser | His | Leu |
| 2765 | | | | 2770 | | | 2775 | | | | |

-continued

```
Arg Leu Cys Leu Gln Asn Lys Gln Trp Ser Gly Thr Val Pro Arg
    2780                2785                2790
Cys Glu Ala Ile Ser Cys Ser Lys Pro Asn Pro Leu Trp Asn Gly
    2795                2800                2805
Ser Ile Lys Gly Asp Asp Tyr Ser Tyr Leu Gly Val Leu Tyr Tyr
    2810                2815                2820
Glu Cys Asp Ser Gly Tyr Ile Leu Asn Gly Ser Lys Lys Arg Thr
    2825                2830                2835
Cys Gln Glu Asn Arg Asp Trp Asp Gly His Glu Pro Met Cys Ile
    2840                2845                2850
Pro Val Asp Cys Gly Ser Pro Pro Val Pro Thr Asn Gly Arg Val
    2855                2860                2865
Lys Gly Glu Glu Tyr Thr Phe Gln Lys Glu Ile Thr Tyr Ser Cys
    2870                2875                2880
Arg Glu Gly Phe Ile Leu Glu Gly Ala Arg Ser Arg Ile Cys Leu
    2885                2890                2895
Thr Asn Gly Ser Trp Ser Gly Ala Thr Pro Ser Cys Met Pro Val
    2900                2905                2910
Arg Cys Pro Ala Pro Pro Gln Val Pro Asn Gly Val Ala Asp Gly
    2915                2920                2925
Leu Asp Tyr Gly Phe Lys Lys Glu Val Ala Phe His Cys Leu Glu
    2930                2935                2940
Gly Tyr Val Leu Gln Gly Ala Pro Arg Leu Thr Cys Gln Ser Asn
    2945                2950                2955
Gly Thr Trp Asp Ala Glu Val Pro Val Cys Lys Pro Ala Thr Cys
    2960                2965                2970
Gly Pro Pro Ala Asp Leu Pro Gln Gly Phe Pro Asn Gly Phe Ser
    2975                2980                2985
Phe Tyr His Gly Gly His Ile Gln Tyr Gln Cys Phe Thr Gly Tyr
    2990                2995                3000
Lys Leu His Gly Asn Pro Ser Arg Arg Cys Leu Pro Asn Gly Ser
    3005                3010                3015
Trp Ser Gly Ser Ser Pro Ser Cys Leu Pro Cys Arg Cys Ser Thr
    3020                3025                3030
Pro Ile Ile Gln Gln Gly Thr Ile Asn Ala Thr Asp Leu Gly Cys
    3035                3040                3045
Gly Lys Thr Val Gln Ile Glu Cys Phe Lys Gly Phe Lys Leu Leu
    3050                3055                3060
Gly Leu Ser Glu Ile Thr Cys Asp Ala Asn Gly Gln Trp Ser Asp
    3065                3070                3075
Val Pro Leu Cys Glu His Ala Gln Cys Gly Pro Leu Pro Thr Ile
    3080                3085                3090
Pro Asn Ala Ile Val Leu Glu Gly Ser Leu Ser Glu Asp Asn Val
    3095                3100                3105
Val Thr Tyr Ser Cys Arg Pro Gly Tyr Thr Met Gln Gly Ser Ser
    3110                3115                3120
Asp Leu Ile Cys Thr Glu Lys Ala Ile Trp Ser Gln Pro Tyr Pro
    3125                3130                3135
Thr Cys Glu Pro Leu Ser Cys Gly Pro Pro Thr Val Ala Asn
    3140                3145                3150
Ala Val Ala Thr Gly Glu Ala His Thr Tyr Glu Ser Lys Val Lys
    3155                3160                3165
```

-continued

```
Leu Arg Cys Leu Glu Gly Tyr Val Met Asp Ser Asp Thr Asp Thr
    3170                3175                3180

Phe Thr Cys Gln Gln Asp Gly His Trp Val Pro Glu Arg Ile Thr
    3185                3190                3195

Cys Ser Pro Lys Lys Cys Pro Val Pro Ser Asn Met Thr Arg Ile
    3200                3205                3210

Arg Phe His Gly Asp Asp Phe Gln Val Asn Arg Gln Val Ser Val
    3215                3220                3225

Ser Cys Ala Glu Gly Phe Thr His Glu Gly Val Asn Trp Ser Thr
    3230                3235                3240

Cys Gln Pro Asp Gly Thr Trp Glu Pro Pro Phe Ser Asp Glu Ser
    3245                3250                3255

Cys Ile Pro Val Val Cys Gly His Pro Glu Ser Pro Ala His Gly
    3260                3265                3270

Ser Val Val Gly Asn Lys His Ser Phe Gly Ser Thr Ile Val Tyr
    3275                3280                3285

Gln Cys Asp Pro Gly Tyr Lys Leu Glu Gly Asn Arg Glu Arg Ile
    3290                3295                3300

Cys Gln Glu Asn Arg Gln Trp Ser Gly Glu Val Ala Val Cys Arg
    3305                3310                3315

Glu Asn Arg Cys Glu Thr Pro Ala Glu Phe Pro Asn Gly Lys Ala
    3320                3325                3330

Val Leu Glu Asn Thr Thr Ser Gly Pro Ser Leu Leu Phe Ser Cys
    3335                3340                3345

His Arg Gly Tyr Thr Leu Glu Gly Ser Pro Glu Ala His Cys Thr
    3350                3355                3360

Ala Asn Gly Thr Trp Asn His Leu Thr Pro Leu Cys Lys Pro Asn
    3365                3370                3375

Pro Cys Pro Val Pro Phe Val Ile Pro Glu Asn Ala Val Leu Ser
    3380                3385                3390

Glu Lys Glu Phe Tyr Val Asp Gln Asn Val Ser Ile Lys Cys Arg
    3395                3400                3405

Glu Gly Phe Leu Leu Lys Gly Asn Gly Val Ile Thr Cys Ser Pro
    3410                3415                3420

Asp Glu Thr Trp Thr His Thr Asn Ala Arg Cys Glu Lys Ile Ser
    3425                3430                3435

Cys Gly Pro Pro Ser His Val Glu Asn Ala Ile Ala Arg Gly Val
    3440                3445                3450

Tyr Tyr Gln Tyr Gly Asp Met Ile Thr Tyr Ser Cys Tyr Ser Gly
    3455                3460                3465

Tyr Met Leu Glu Gly Ser Leu Arg Ser Val Cys Leu Glu Asn Gly
    3470                3475                3480

Thr Trp Thr Pro Ser Pro Val Cys Arg Ala Val Cys Arg Phe Pro
    3485                3490                3495

Cys Gln Asn Gly Gly Val Cys Gln Arg Pro Asn Ala Cys Ser Cys
    3500                3505                3510

Pro Asp Gly Trp Met Gly Arg Leu Cys Glu Glu Pro Ile Cys Ile
    3515                3520                3525

Leu Pro Cys Leu Asn Gly Gly Arg Cys Val Ala Pro Tyr Gln Cys
    3530                3535                3540

Asp Cys Pro Thr Gly Trp Thr Gly Ser Arg Cys His Thr Ala Thr
    3545                3550                3555

Cys Gln Ser Pro Cys Leu Asn Gly Gly Lys Cys Ile Arg Pro Asn
```

-continued

```
          3560                3565                3570
Arg Cys His Cys Leu Ser Ala Trp Thr Gly His Asp Cys Ser Arg
    3575                3580                3585
Lys Arg Arg Ala Gly Leu
    3590

<210> SEQ ID NO 5
<211> LENGTH: 2489
<212> TYPE: PRT
<213> ORGANISM: Homo sapiens

<400> SEQUENCE: 5

Met Gly Ala Ser Ser Pro Arg Ser Pro Glu Pro Val Gly Pro Pro Ala
1               5                   10                  15

Pro Gly Leu Pro Phe Cys Cys Gly Ser Leu Leu Ala Val Val Val
            20                  25                  30

Leu Leu Ala Leu Pro Val Ala Trp Gly Gln Cys Asn Ala Pro Glu Trp
        35                  40                  45

Leu Pro Phe Ala Arg Pro Thr Asn Leu Thr Asp Glu Phe Glu Phe Pro
    50                  55                  60

Ile Gly Thr Tyr Leu Asn Tyr Glu Cys Arg Pro Gly Tyr Ser Gly Arg
65                  70                  75                  80

Pro Phe Ser Ile Ile Cys Leu Lys Asn Ser Val Trp Thr Gly Ala Lys
                85                  90                  95

Asp Arg Cys Arg Arg Lys Ser Cys Arg Asn Pro Pro Asp Pro Val Asn
            100                 105                 110

Gly Met Val His Val Ile Lys Gly Ile Gln Phe Gly Ser Gln Ile Lys
        115                 120                 125

Tyr Ser Cys Thr Lys Gly Tyr Arg Leu Ile Gly Ser Ser Ser Ala Thr
    130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                165                 170                 175

Phe Ile Ser Thr Asn Arg Glu Asn Phe His Tyr Gly Ser Val Val Thr
            180                 185                 190

Tyr Arg Cys Asn Pro Gly Ser Gly Gly Arg Lys Val Phe Glu Leu Val
        195                 200                 205

Gly Glu Pro Ser Ile Tyr Cys Thr Ser Asn Asp Asp Gln Val Gly Ile
    210                 215                 220

Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
                245                 250                 255

Ser Leu Asn Glu Val Val Glu Phe Arg Cys Gln Pro Gly Phe Val Met
            260                 265                 270

Lys Gly Pro Arg Arg Val Lys Cys Gln Ala Leu Asn Lys Trp Glu Pro
        275                 280                 285

Glu Leu Pro Ser Cys Ser Arg Val Cys Gln Pro Pro Pro Asp Val Leu
    290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                325                 330                 335
```

```
Ser Met Arg Cys Thr Pro Gln Gly Asp Trp Ser Pro Ala Ala Pro Thr
            340                 345                 350

Cys Glu Val Lys Ser Cys Asp Asp Phe Met Gly Gln Leu Leu Asn Gly
            355                 360                 365

Arg Val Leu Phe Pro Val Asn Leu Gln Leu Gly Ala Lys Val Asp Phe
            370                 375                 380

Val Cys Asp Glu Gly Phe Gln Leu Lys Gly Ser Ser Ala Ser Tyr Cys
385                 390                 395                 400

Val Leu Ala Gly Met Glu Ser Leu Trp Asn Ser Ser Val Pro Val Cys
                405                 410                 415

Glu Gln Ile Phe Cys Pro Ser Pro Val Ile Pro Asn Gly Arg His
            420                 425                 430

Thr Gly Lys Pro Leu Glu Val Phe Pro Phe Gly Lys Ala Val Asn Tyr
            435                 440                 445

Thr Cys Asp Pro His Pro Asp Arg Gly Thr Ser Phe Asp Leu Ile Gly
            450                 455                 460

Glu Ser Thr Ile Arg Cys Thr Ser Asp Pro Gln Gly Asn Gly Val Trp
465                 470                 475                 480

Ser Ser Pro Ala Pro Arg Cys Gly Ile Leu Gly His Cys Gln Ala Pro
                485                 490                 495

Asp His Phe Leu Phe Ala Lys Leu Lys Thr Gln Thr Asn Ala Ser Asp
            500                 505                 510

Phe Pro Ile Gly Thr Ser Leu Lys Tyr Glu Cys Arg Pro Glu Tyr Tyr
            515                 520                 525

Gly Arg Pro Phe Ser Ile Thr Cys Leu Asp Asn Leu Val Trp Ser Ser
            530                 535                 540

Pro Lys Asp Val Cys Lys Arg Lys Ser Cys Lys Thr Pro Pro Asp Pro
545                 550                 555                 560

Val Asn Gly Met Val His Val Ile Thr Asp Ile Gln Val Gly Ser Arg
                565                 570                 575

Ile Asn Tyr Ser Cys Thr Thr Gly His Arg Leu Ile Gly His Ser Ser
            580                 585                 590

Ala Glu Cys Ile Leu Ser Gly Asn Ala Ala His Trp Ser Thr Lys Pro
            595                 600                 605

Pro Ile Cys Gln Arg Ile Pro Cys Gly Leu Pro Pro Thr Ile Ala Asn
            610                 615                 620

Gly Asp Phe Ile Ser Thr Asn Arg Glu Asn Phe His Tyr Gly Ser Val
625                 630                 635                 640

Val Thr Tyr Arg Cys Asn Pro Gly Ser Gly Gly Arg Lys Val Phe Glu
                645                 650                 655

Leu Val Gly Glu Pro Ser Ile Tyr Cys Thr Ser Asn Asp Asp Gln Val
            660                 665                 670

Gly Ile Trp Ser Gly Pro Ala Pro Gln Cys Ile Ile Pro Asn Lys Cys
            675                 680                 685

Thr Pro Pro Asn Val Glu Asn Gly Ile Leu Val Ser Asp Asn Arg Ser
            690                 695                 700

Leu Phe Ser Leu Asn Glu Val Val Glu Phe Arg Cys Gln Pro Gly Phe
705                 710                 715                 720

Val Met Lys Gly Pro Arg Arg Val Lys Cys Gln Ala Leu Asn Lys Trp
                725                 730                 735

Glu Pro Glu Leu Pro Ser Cys Ser Arg Val Cys Gln Pro Pro Pro Asp
            740                 745                 750

Val Leu His Ala Glu Arg Thr Gln Arg Asp Lys Asp Asn Phe Ser Pro
```

-continued

```
            755                 760                 765
Gly Gln Glu Val Phe Tyr Ser Cys Glu Pro Gly Tyr Asp Leu Arg Gly
        770                 775                 780
Ala Ala Ser Met Arg Cys Thr Pro Gln Gly Asp Trp Ser Pro Ala Ala
785                 790                 795                 800
Pro Thr Cys Glu Val Lys Ser Cys Asp Asp Phe Met Gly Gln Leu Leu
                805                 810                 815
Asn Gly Arg Val Leu Phe Pro Val Asn Leu Gln Leu Gly Ala Lys Val
            820                 825                 830
Asp Phe Val Cys Asp Glu Gly Phe Gln Leu Lys Gly Ser Ser Ala Ser
            835                 840                 845
Tyr Cys Val Leu Ala Gly Met Glu Ser Leu Trp Asn Ser Ser Val Pro
    850                 855                 860
Val Cys Glu Gln Ile Phe Cys Pro Ser Pro Val Ile Pro Asn Gly
865                 870                 875                 880
Arg His Thr Gly Lys Pro Leu Glu Val Phe Pro Phe Gly Lys Thr Val
                885                 890                 895
Asn Tyr Thr Cys Asp Pro His Pro Asp Arg Gly Thr Ser Phe Asp Leu
            900                 905                 910
Ile Gly Glu Ser Thr Ile Arg Cys Thr Ser Asp Pro Gln Gly Asn Gly
            915                 920                 925
Val Trp Ser Ser Pro Ala Pro Arg Cys Gly Ile Leu Gly His Cys Gln
    930                 935                 940
Ala Pro Asp His Phe Leu Phe Ala Lys Leu Lys Thr Gln Thr Asn Ala
945                 950                 955                 960
Ser Asp Phe Pro Ile Gly Thr Ser Leu Lys Tyr Glu Cys Arg Pro Glu
                965                 970                 975
Tyr Tyr Gly Arg Pro Phe Ser Ile Thr Cys Leu Asp Asn Leu Val Trp
            980                 985                 990
Ser Ser Pro Lys Asp Val Cys Lys Arg Lys Ser Cys Lys Thr Pro Pro
            995                 1000                1005
Asp Pro Val Asn Gly Met Val His Val Ile Thr Asp Ile Gln Val
        1010                1015                1020
Gly Ser Arg Ile Asn Tyr Ser Cys Thr Thr Gly His Arg Leu Ile
        1025                1030                1035
Gly His Ser Ser Ala Glu Cys Ile Leu Ser Gly Asn Ala Ala His
        1040                1045                1050
Trp Ser Thr Lys Pro Pro Ile Cys Gln Arg Ile Pro Cys Gly Leu
        1055                1060                1065
Pro Pro Thr Ile Ala Asn Gly Asp Phe Ile Ser Thr Asn Arg Glu
        1070                1075                1080
Asn Phe His Tyr Gly Ser Val Val Thr Tyr Arg Cys Asn Pro Gly
        1085                1090                1095
Ser Gly Gly Arg Lys Val Phe Glu Leu Val Gly Glu Pro Ser Ile
        1100                1105                1110
Tyr Cys Thr Ser Asn Asp Asp Gln Val Gly Ile Trp Ser Gly Pro
        1115                1120                1125
Ala Pro Gln Cys Ile Ile Pro Asn Lys Cys Thr Pro Pro Asn Val
        1130                1135                1140
Glu Asn Gly Ile Leu Val Ser Asp Asn Arg Ser Leu Phe Ser Leu
        1145                1150                1155
Asn Glu Val Val Glu Phe Arg Cys Gln Pro Gly Phe Val Met Lys
        1160                1165                1170
```

-continued

Gly Pro Arg Arg Val Lys Cys Gln Ala Leu Asn Lys Trp Glu Pro
1175                1180                    1185

Glu Leu Pro Ser Cys Ser Arg Val Cys Gln Pro Pro Asp Val
1190                1195                1200

Leu His Ala Glu Arg Thr Gln Arg Asp Lys Asp Asn Phe Ser Pro
1205                1210                    1215

Gly Gln Glu Val Phe Tyr Ser Cys Glu Pro Gly Tyr Asp Leu Arg
1220                1225                    1230

Gly Ala Ala Ser Met Arg Cys Thr Pro Gln Gly Asp Trp Ser Pro
1235                1240                    1245

Ala Ala Pro Thr Cys Glu Val Lys Ser Cys Asp Asp Phe Met Gly
1250                1255                    1260

Gln Leu Leu Asn Gly Arg Val Leu Phe Pro Val Asn Leu Gln Leu
1265                1270                    1275

Gly Ala Lys Val Asp Phe Val Cys Asp Glu Gly Phe Gln Leu Lys
1280                1285                    1290

Gly Ser Ser Ala Ser Tyr Cys Val Leu Ala Gly Met Glu Ser Leu
1295                1300                    1305

Trp Asn Ser Ser Val Pro Val Cys Glu Gln Ile Phe Cys Pro Ser
1310                1315                    1320

Pro Pro Val Ile Pro Asn Gly Arg His Thr Gly Lys Pro Leu Glu
1325                1330                    1335

Val Phe Pro Phe Gly Lys Ala Val Asn Tyr Thr Cys Asp Pro His
1340                1345                    1350

Pro Asp Arg Gly Thr Ser Phe Asp Leu Ile Gly Glu Ser Thr Ile
1355                1360                    1365

Arg Cys Thr Ser Asp Pro Gln Gly Asn Gly Val Trp Ser Ser Pro
1370                1375                    1380

Ala Pro Arg Cys Gly Ile Leu Gly His Cys Gln Ala Pro Asp His
1385                1390                    1395

Phe Leu Phe Ala Lys Leu Lys Thr Gln Thr Asn Ala Ser Asp Phe
1400                1405                    1410

Pro Ile Gly Thr Ser Leu Lys Tyr Glu Cys Arg Pro Glu Tyr Tyr
1415                1420                    1425

Gly Arg Pro Phe Ser Ile Thr Cys Leu Asp Asn Leu Val Trp Ser
1430                1435                    1440

Ser Pro Lys Asp Val Cys Lys Arg Lys Ser Cys Lys Thr Pro Pro
1445                1450                    1455

Asp Pro Val Asn Gly Met Val His Val Ile Thr Asp Ile Gln Val
1460                1465                    1470

Gly Ser Arg Ile Asn Tyr Ser Cys Thr Thr Gly His Arg Leu Ile
1475                1480                    1485

Gly His Ser Ser Ala Glu Cys Ile Leu Ser Gly Asn Thr Ala His
1490                1495                    1500

Trp Ser Thr Lys Pro Pro Ile Cys Gln Arg Ile Pro Cys Gly Leu
1505                1510                    1515

Pro Pro Thr Ile Ala Asn Gly Asp Phe Ile Ser Thr Asn Arg Glu
1520                1525                    1530

Asn Phe His Tyr Gly Ser Val Val Thr Tyr Arg Cys Asn Leu Gly
1535                1540                    1545

Ser Arg Gly Arg Lys Val Phe Glu Leu Val Gly Glu Pro Ser Ile
1550                1555                    1560

```
Tyr Cys Thr Ser Asn Asp Asp Gln Val Gly Ile Trp Ser Gly Pro
1565                1570                    1575

Ala Pro Gln Cys Ile Ile Pro Asn Lys Cys Thr Pro Pro Asn Val
1580                1585                    1590

Glu Asn Gly Ile Leu Val Ser Asp Asn Arg Ser Leu Phe Ser Leu
1595                1600                    1605

Asn Glu Val Val Glu Phe Arg Cys Gln Pro Gly Phe Val Met Lys
1610                1615                    1620

Gly Pro Arg Arg Val Lys Cys Gln Ala Leu Asn Lys Trp Glu Pro
1625                1630                    1635

Glu Leu Pro Ser Cys Ser Arg Val Cys Gln Pro Pro Pro Glu Ile
1640                1645                    1650

Leu His Gly Glu His Thr Pro Ser His Gln Asp Asn Phe Ser Pro
1655                1660                    1665

Gly Gln Glu Val Phe Tyr Ser Cys Glu Pro Gly Tyr Asp Leu Arg
1670                1675                    1680

Gly Ala Ala Ser Leu His Cys Thr Pro Gln Gly Asp Trp Ser Pro
1685                1690                    1695

Glu Ala Pro Arg Cys Ala Val Lys Ser Cys Asp Asp Phe Leu Gly
1700                1705                    1710

Gln Leu Pro His Gly Arg Val Leu Phe Pro Leu Asn Leu Gln Leu
1715                1720                    1725

Gly Ala Lys Val Ser Phe Val Cys Asp Glu Gly Phe Arg Leu Lys
1730                1735                    1740

Gly Ser Ser Val Ser His Cys Val Leu Val Gly Met Arg Ser Leu
1745                1750                    1755

Trp Asn Asn Ser Val Pro Val Cys Glu His Ile Phe Cys Pro Asn
1760                1765                    1770

Pro Pro Ala Ile Leu Asn Gly Arg His Thr Gly Thr Pro Ser Gly
1775                1780                    1785

Asp Ile Pro Tyr Gly Lys Glu Ile Ser Tyr Thr Cys Asp Pro His
1790                1795                    1800

Pro Asp Arg Gly Met Thr Phe Asn Leu Ile Gly Glu Ser Thr Ile
1805                1810                    1815

Arg Cys Thr Ser Asp Pro His Gly Asn Gly Val Trp Ser Ser Pro
1820                1825                    1830

Ala Pro Arg Cys Glu Leu Ser Val Arg Ala Gly His Cys Lys Thr
1835                1840                    1845

Pro Glu Gln Phe Pro Phe Ala Ser Pro Thr Ile Pro Ile Asn Asp
1850                1855                    1860

Phe Glu Phe Pro Val Gly Thr Ser Leu Asn Tyr Glu Cys Arg Pro
1865                1870                    1875

Gly Tyr Phe Gly Lys Met Phe Ser Ile Ser Cys Leu Glu Asn Leu
1880                1885                    1890

Val Trp Ser Ser Val Glu Asp Asn Cys Arg Arg Lys Ser Cys Gly
1895                1900                    1905

Pro Pro Pro Glu Pro Phe Asn Gly Met Val His Ile Asn Thr Asp
1910                1915                    1920

Thr Gln Phe Gly Ser Thr Val Asn Tyr Ser Cys Asn Glu Gly Phe
1925                1930                    1935

Arg Leu Ile Gly Ser Pro Ser Thr Thr Cys Leu Val Ser Gly Asn
1940                1945                    1950

Asn Val Thr Trp Asp Lys Lys Ala Pro Ile Cys Glu Ile Ile Ser
```

-continued

```
        1955                1960                1965

Cys Glu Pro Pro Thr Ile Ser Asn Gly Asp Phe Tyr Ser Asn
    1970            1975            1980

Asn Arg Thr Ser Phe His Asn Gly Thr Val Val Thr Tyr Gln Cys
    1985            1990            1995

His Thr Gly Pro Asp Gly Glu Gln Leu Phe Glu Leu Val Gly Glu
    2000            2005            2010

Arg Ser Ile Tyr Cys Thr Ser Lys Asp Asp Gln Val Gly Val Trp
    2015            2020            2025

Ser Ser Pro Pro Pro Arg Cys Ile Ser Thr Asn Lys Cys Thr Ala
    2030            2035            2040

Pro Glu Val Glu Asn Ala Ile Arg Val Pro Gly Asn Arg Ser Phe
    2045            2050            2055

Phe Ser Leu Thr Glu Ile Val Arg Phe Arg Cys Gln Pro Gly Phe
    2060            2065            2070

Val Met Val Gly Ser His Thr Val Gln Cys Gln Thr Asn Gly Arg
    2075            2080            2085

Trp Gly Pro Lys Leu Pro His Cys Ser Arg Val Cys Gln Pro Pro
    2090            2095            2100

Pro Glu Ile Leu His Gly Glu His Thr Leu Ser His Gln Asp Asn
    2105            2110            2115

Phe Ser Pro Gly Gln Glu Val Phe Tyr Ser Cys Glu Pro Ser Tyr
    2120            2125            2130

Asp Leu Arg Gly Ala Ala Ser Leu His Cys Thr Pro Gln Gly Asp
    2135            2140            2145

Trp Ser Pro Glu Ala Pro Arg Cys Thr Val Lys Ser Cys Asp Asp
    2150            2155            2160

Phe Leu Gly Gln Leu Pro His Gly Arg Val Leu Leu Pro Leu Asn
    2165            2170            2175

Leu Gln Leu Gly Ala Lys Val Ser Phe Val Cys Asp Glu Gly Phe
    2180            2185            2190

Arg Leu Lys Gly Arg Ser Ala Ser His Cys Val Leu Ala Gly Met
    2195            2200            2205

Lys Ala Leu Trp Asn Ser Ser Val Pro Val Cys Glu Gln Ile Phe
    2210            2215            2220

Cys Pro Asn Pro Pro Ala Ile Leu Asn Gly Arg His Thr Gly Thr
    2225            2230            2235

Pro Phe Gly Asp Ile Pro Tyr Gly Lys Glu Ile Ser Tyr Ala Cys
    2240            2245            2250

Asp Thr His Pro Asp Arg Gly Met Thr Phe Asn Leu Ile Gly Glu
    2255            2260            2265

Ser Ser Ile Arg Cys Thr Ser Asp Arg Gln Gly Asn Gly Val Trp
    2270            2275            2280

Ser Ser Pro Ala Pro Arg Cys Glu Leu Ser Val Pro Ala Ala Cys
    2285            2290            2295

Pro Asp Pro Pro Lys Ile Gln Asn Gly His Tyr Ile Gly Gly His
    2300            2305            2310

Val Ser Leu Tyr Leu Pro Gly Met Thr Ile Ser Tyr Ile Cys Asp
    2315            2320            2325

Pro Gly Tyr Leu Leu Val Gly Lys Gly Phe Ile Phe Cys Thr Asp
    2330            2335            2340

Gln Gly Ile Trp Ser Gln Leu Asp His Tyr Cys Lys Glu Val Asn
    2345            2350            2355
```

-continued

```
Cys Ser Phe Pro Leu Phe Met Asn Gly Ile Ser Lys Glu Leu Glu
    2360                2365                2370

Met Lys Lys Val Tyr His Tyr Gly Asp Tyr Val Thr Leu Lys Cys
    2375                2380                2385

Glu Asp Gly Tyr Thr Leu Glu Gly Ser Pro Trp Ser Gln Cys Gln
    2390                2395                2400

Ala Asp Asp Arg Trp Asp Pro Pro Leu Ala Lys Cys Thr Ser Arg
    2405                2410                2415

Ala His Asp Ala Leu Ile Val Gly Thr Leu Ser Gly Thr Ile Phe
    2420                2425                2430

Phe Ile Leu Leu Ile Ile Phe Leu Ser Trp Ile Ile Leu Lys His
    2435                2440                2445

Arg Lys Gly Asn Asn Ala His Glu Asn Pro Lys Glu Val Ala Ile
    2450                2455                2460

His Leu His Ser Gln Gly Gly Ser Ser Val His Pro Arg Thr Leu
    2465                2470                2475

Gln Thr Asn Glu Glu Asn Ser Arg Val Leu Pro
    2480                2485
```

<210> SEQ ID NO 6
<211> LENGTH: 11
<212> TYPE: PRT
<213> ORGANISM: Homo sapiens

<400> SEQUENCE: 6

```
Tyr Gly Arg Lys Lys Arg Arg Gln Arg Arg Arg
1               5                   10
```

<210> SEQ ID NO 7
<211> LENGTH: 15
<212> TYPE: PRT
<213> ORGANISM: Homo sapiens

<400> SEQUENCE: 7

```
Gly Gly Gly Gly Tyr Gly Arg Lys Lys Arg Arg Gln Arg Arg Arg
1               5                   10                  15
```